US006965023B2

(12) United States Patent
Reed et al.

(10) Patent No.: US 6,965,023 B2
(45) Date of Patent: Nov. 15, 2005

(54) DEATH DOMAIN PROTEINS

(75) Inventors: John C. Reed, Rancho Santa Fe, CA (US); Adam Godzik, San Diego, CA (US); Krzysztof Pawlowski, Malmo (SE); Loredana Fiorentino, San Diego, CA (US); Sug Hyung Lee, Seoul (KR); Wilfried Roth, La Jolla, CA (US); Frank Stenner-Liewen, Homburg/Saar (DE)

(73) Assignee: The Burnham Institute, La Jolla, CA (US)

(*) Notice: Subject to any disclaimer, the term of this patent is extended or adjusted under 35 U.S.C. 154(b) by 246 days.

(21) Appl. No.: 10/001,254

(22) Filed: Nov. 15, 2001

(65) Prior Publication Data

US 2003/0049702 A1 Mar. 13, 2003

Related U.S. Application Data

(60) Provisional application No. 60/301,889, filed on Jun. 29, 2001, and provisional application No. 60/367,360, filed on Nov. 17, 2000.

(51) Int. Cl.[7] .......................... C07H 21/02; C12P 21/06; C12N 15/00; C12N 5/00

(52) U.S. Cl. .................. 536/23.5; 435/69.1; 435/320.1; 435/325

(58) Field of Search .............................. 536/23.5, 23.1, 536/24.33; 435/69.1, 320.1, 325

(56) References Cited

U.S. PATENT DOCUMENTS 6,440,663 B1 * 8/2002 Scanlan et al. ................ 435/6

FOREIGN PATENT DOCUMENTS

| WO | WO 95/10630 | 4/1995 |
|---|---|---|
| WO | WO 97/00690 | 1/1997 |
| WO | WO 98/39429 | 9/1998 |
| WO | WO 99/27112 | 6/1999 |
| WO | WO00/20587 | 4/2000 |
| WO | WO 01/51641 | 7/2001 |

OTHER PUBLICATIONS

Watanabe et al. (GenEmbl/PRI Database, Accession No. AK000528, Feb. 22, 2000).*
EST Database, Accession No. AA114228, Nov. 13, 1996, IDS.*
Matthews et al. (Anal.Biochem., vol. 169, Feb. 1988, pp. 1–25).*
Berger et al., "The apoptosis mediator mDAP-3 is a novel member of a conserved family of mitochondrial proteins," *Journal of Cell Science*, 113:3603–3612 (2000).
Feinstein et al., "The death domain: a module shared by proteins with diverse Cellular functions," *Trends in Biochemical Sciences*, 20:342–344 (1995).
Han et al., "MRIT, a novel death–effector domain–containing protein, interacts with caspases and Bc1X$_L$ and initiates cell death," *Proc. Natl. Acad. Sci. USA*, 94:11333–11338 (1997).
Hofmann, K., "The modular nature of apoptic signaling proteins," *Cell. Mol. Life Sci.*, 55:1113–1123 (1999).
Kumar et al., "Identification of a Novel Tumor Necrosis Factor–α–inducible Gene, SCC–S2, Containing the Consensus Sequence of a Death Effector Domain of Fas–associated Death Domain–like Interleukin–1β–converting Enzyme–inhibitory Protein," *J. Biol. Chem.*, 275:2973–2978 (2000).
Liang and Fesik, "Three–dimensional Structures of Proteins Involved in Programmed Cell Death," *J. Mol. Biol.*, 274:291–302 (1997).
Park et al., "Establishment of a High–Throughput Screening System for Caspase–3 Inhibitors," *Arch. Pharm. Res.*, 23:246–251 (2000).
Reed and Tomaselli, "Drug discovery opportunities from apoptosis research," *Current Opin. Biotech.*, 11:586–592 (2000).
Altschul et al., "Basic local alignment search tool," *J. Mol. Biol.* 215:403–410 (1990).
Altschul et al., "Gapped BLAST and PSI–BLAST: a new generation of protein database search programs," *Nucleic Acids Res.* 25:3389–3402 (1997).
Ashkenazi and Dixit, "Death receptors: signaling and modulation," *Science* 281:1305–1308 (1998).
Boldin et al., "Involvement of MACH, a novel MORT1/FADD–interacting protease, in Fas/Apo–1– and TNF receptor–induced cell death," *Cell*, 85: 803–815 (1996).
Campbell et al., "The development of *Chlamydia trachomatis* inclusions within the host eukaryotic cell during interphase and mitosis," *J. Gen. Micro.* 135:1153–1165 (1989).
Deveraux et al., "X–linked IAP is a direct inhibitor of cell death proteases," *Nature* 388:300–304 (1997).
Eberstadt et al., "NMR structure and mutagenesis of the FADD (Mort1) death–effector domain," *Nature* 392:941–945 (1998).
Estojak et al., "Correlation of two–hybrid affinity data with in vitro measurements," *Mol. Cell Biol.* 15:5820 (1995).

(Continued)

*Primary Examiner*—Gary B. Nickol
(74) *Attorney, Agent, or Firm*—McDermott Will & Emery LLP

(57) ABSTRACT

In accordance with the present invention, there are provided novel Death Domain (DD), Death Effector Domain (DED) and NB-ARC domain proteins. The invention also provides nucleic acid molecules encoding DD, DED and NB-ARC domain proteins, vectors containing these nucleic acid molecules and host cells containing the vectors. The invention also provides antibodies that can specifically bind to invention DDs, DEDs or NB-ARC domains. Such DDs, DEDs and NB-ARC domains and/or anti-DD, anti-DED or anti-NB-ARC domain antibodies are useful for discovery of drugs that suppress infection, autoimmunity, inflammation, allergy, allograft rejection, sepsis, and other diseases.

11 Claims, 32 Drawing Sheets

OTHER PUBLICATIONS

Fan et al., "Inhibition of apoptosis in Chlamydia–infected cells: blockade of mitochondrial cytochrome c release and caspase activation," *J. Exp. Med.* 187:487–497 (1998).
Gibellini et al., "Inhibition of apoptosis by *Chlamydia psittaci* and *Chlamydia trachomatis* infection in tissue culture cells," *Zentralblatt fur Bakteriologie* 288:35–43 (1998).
Gish and States, "Identification of protein coding regions by database similarity search," *Nature Genet.* 3:266–272 (1993).
Grutter, "Caspases: key player in programmed cell death," *Curr. Opin. Struct. Biol.* 10:649–655 (2000).
Haraguchi et al., "Apoptotic protease activating factor 1 (Apfa–1)—independent cell death suppression by Bcl–2," *J. Exp. Med.* 191:1709–1720 (2000).
Hauser and Engel, "*Pseudomonas aeruginosa* induces type–III–secretion–mediated apoptosis of macrophages and epithelial cells," *Infect. Immun.* 67:5530–5537 (1999).
Hersh et al., "The Salmonella invasion SipB induces macrophage apoptosis by binding to caspase–1" *Proc. Natl. Acad. Sci. USA* 96:2396–2401 (1999).
Jaroszewski et al., "Fold prediction by a hierarchy of sequence threading and modeling methods," *Protein Sciences* 7:1431–1440 (1998).
Juo et al., "Essential requirement for caspase–8/FLICE in the initiation of the Fas–induced apoptotic cascade," *Curr. Biol.* 8:1001–1008 (1998).
Kischkel et al., "Apo2L/TRAIL–dependent recruitment of endogenous FADD and caspase–8 death receptors 4 and 5," *Immunity,* 12:611–620 (2000).
Kissil et al., "Isolation of DAP3, a novel mediator of interferon–Y–induced cell death," *J. Biol. Chem.* 270:27932–27936 (1995).
Kissil et al., "Structure–function analysis of an evolutionary conserved protein, DAP3, which mediates TNF–$\alpha$– and Fas–induced cell death," *EMBO J.* 18:353–362 (1999).
Leo et al., "Differential requirements for tumor necrosis factor receptor–associated factor family proteins in CD40–mediated induction of NF–kB and jun N–terminal activation," *J. Biol. Chem.* 274:22414–11422 (1999).
Li et al., "Saturated BLAST: an automated multiple intermediate sequence search used to detect distant homology," *Bioinformaticts* 16:1105–1110 (2000).
Madden et al., "Applications of Network BLAST server," *Meth. Enzymol.* 266: 131–141 (1996).
Matsuzawa et al., "p53–inducible human homologue of *Drosophila seven* in *absentia* (Siah) inhibits cell growth: suppression of BAG–1," *EMBO J.* 17:2736–2747 (1998).
Muzio et al. "An induced proximity model for caspase–8 activation," *J. Biol. Chem.* 273:2926–2930 (1998).
Muzio et al., "FLICE, a novel FADD–homologous ICE/CED–3–like protease, is recruited to the CD95 (Fas/APO–1) death–inducing signaling complex," *Cell* 85:817–827 (1996).
Nagata, S., "Fas–induced apoptosis, a disease caused by abnormality," *Genes Cells* 1:873–879 (1996).
Oddo et al., "Fas ligand–induced apoptosis of infected human macrophages reduces the viability of intracellular *Mycobacterium tuberculosis,*" *J. Immunol.* 160:5448–5454 (1998).
Ojcius et al., "Apoptosis of epithelial cells and macrophages due to infection with the obligate intracellular pathogen *Chlamydia psittaci,*" *J. Immunol.* 161:4220–4226 (1998).

Ojcius et al., "Enhancement of ATP levels and glucose metabolism during an infection by Chlamydia," *J. Biol. Chem.* 273:7052–7058 (1998).
Sali, A. and Blundell, T., "Comperative protein modelling by satisfaction of spatial restraints," *J. Mol. Biol.* 234:779–815 (1993).
Salvesen and Dixit, "Caspase activation: the induced–proximity model," *Proc. Natl. Acad. Sci. USA* 96:10964–10967 (1999).
Salvasen et al., "Caspase 8: igniting the death machine," *Structure Fold. Des.* 7:R225–229 (1999).
Sato et al., "A novel member of TRAF family of putative signal transducing proteins binds to the cytosolic domain of CD40," *FEBS Lett.* 358:113–118 (1995).
Sato et al., "FAP–1: A protein tyrosine phosphatase that associates with Fas," *Science* 268:411–415 (1995).
Sato et al., "Interactions among members of the Bcl–2 protein family analyzed with a yeast two–hybrid system," *Proc. Natl. Acad. Sci. USA* 91:9238–9242 (1994).
Scanlan et al., "Antigens recognized by autologous antibody in patients with renal–cell carcinoma," *Int. J. Cancer* 83: 456–464 (1999).
Schneider et al., "Characterization of two receptors for TRAIL," *FEBS Lett.* 416: 329–334 (1997).
Schneider et al. "TRAIL receptors 1 (DR4) and 2 (DR5) signal FADD–dependent apoptosis and activate NF-κB," *Immunity* 7:831–836 (1997).
Sprick et al., "FADD/MORT1 and caspase–8 recruited to TRAIL receptors 1 and 2 and are essential for apoptosis mediated by TRAIL receptor 2," *Immunity* 12:599–609 (2000).
Srinivasula et al., "Autoactivation of procaspase–9 by Apaf–1–mediated oligomerization," *Mol. Cell* 1:949–957 (1998).
Stegh, et al., "DEDD, a novel death effector domain–containing protein, targeted to the nucleolus," *EMBO J.* 17:5974–5986 (1998).
Takayama et al., "BAG–1 modulates the chaperone activity of Hsp70/Hsc70," *EMBO J.* 16:4887–4896 (1997).
Tatusova and Madden, "BLAST 2 sequences, a new tool for comparing protein and nucleotide sequences," *FEMS Microbiol. Lett.* 174:247–250 (1999).
Thornberry et al., "A combinatorial approach defines specificities of members of the caspase family and granzyme B," *J. Biol. Chem.* 272:17907–17911 (1997).
Torii et al., Human daxx regulates fas–induced apoptosis from nuclear PML oncogenic domains (PODs). *EMBO J.* 18:6037–6049 (1999).
Tyers and Jorgesen, "Proteolysis and the cell cycle: with this RING I do thee destroy," *Curr. Opin. Genet. Dev.* 10:54–64 (2000).
van der Biezen and Jones, "The NB–ARC domain: a novel signaling motif shared by plant resistance gene products and regulators of cell death in animals," *Curr. Biol.* 8:R226–R227 (1998).
Varfolomeev et al., "Targeted disruptions of the mouse caspase 8 gene ablates cell death induction by the TNF receptors, Fas/Apo1, and is lethal prenatally," *Immunity* 9:267–276 (1998).
Walczak et al., "TRAIL–R2: a novel apoptosis–mediating receptor for TRAIL," *EMBO J.* 16:5386–5397 (1997).
Wallach et al., "Tumor necrosis factor receptor and Fas signaling mechanisms," *Annu. Rev. Immunol.* 17:331–367 (1999).

Wang and Lenardo, "Molecules involved in cell death and peripheral tolerance," *Curr. Opin. Immunol.* 9:818–825 (1997).

Yang et al., "Essential role of CED–4 oligomerization in CED–3 activation and apoptosis," *Science* 281:1355–1357 (1998).

Zhang and Madden, "PowerBLAST: a new network BLAST application for interactive or automated sequence analysis and annotation," *Genome Res.* 7:649–656 (1997).

Zychlinsky et al., "*Shigella flexneri* induces apoptosis in infected macrophages," *Nature* 358:167–169 (1992).

GenBank Accession No. AA114228; GI No. 1668121.
GenBank Accession No. AA218681; GI No. 1832773.
GenBank Accession No. AAD42884; GI No. 5360131.
GenBank Accession No. AAF39693; GI No. 7190927.
GenBank Accession No. AC006486; GI No. 4210498.
GenBank Accession No. AE001331; GI No. 3329046.
GenBank Accession No. AF155118; GI No. 5360130.
GenBank Accession No. AI598730; GI No. 4607778.
GenBank Accession No. AV149215; GI No. 5353348.
GenBank Accession No. AW227145; GI No. 6556441.
GenBank Accession No. AW229739; GI No. 6559035.
GenBank Accession No. AW429324; GI No. 6960635.
GenBank Accession No. AW449244; GI No. 6990020.
GenBank Accession No. B72040; GI No. 7468151.
GenBank Accession No. BE242821; GI No. 9094541.
GenBank Accession No. BE797255; GI No. 10218453.
GenBank Accession No. NM016123; GI No. 7705840.
GenBank Accession No. NP004623; GI No. 4758118.
GenBank Accession No. NP057207; GI No. 7705841.
Genbank Accession No. X83544; GI No. 1089849.
Genbank Accession No. Q9Y589.
Genbank Accession No. AK000528.
Genbank Accession No. Q9NWZ3.

Kanakaraj et al., "Interleukin (IL)–1 receptor–associated kinase (IRAK) requirement for optimal induction of multiple IL–1 signaling pathways and IL–6 production," *J. Exp. Med.* 187:2073–2079 (1998).

Kissil et al., "Isolation of DAP3, a novel mediator of interferon–γ–induced cell death," *J. Biol. Chem.* 270:27932–27936 (1995).

Stegh et al., "DEDD, a novel death effector domain–containing protein, targeted to the nucleous," *EMBO J.* 17:5974–5986 (1998).

van der Biezen and Jones, "The NB–ARC domain: a novel signalling motif shared by plant resistance gene products and regulators of cell death in animals," *Current Biol.* 8:226–227 (1998).

Wesche et al., "IRAK–M is a novel member of the pelle/interleukin–1 receptor–associated kinase (IRAK) family," *J. Biol. Chem.* 274:19403–19410 (1999).

* cited by examiner

B  anti-Fas:     − − − + + +
   DAP3-Flag:    + − + + − +
   FADD-HA:      − + + − + +
FADD ► 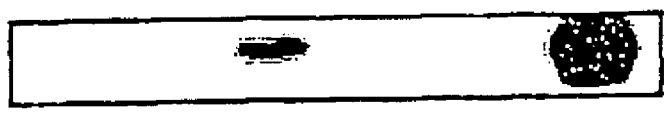
IP: anti-Flag     Blot: anti-HA
Lysates:
DAP3 ► 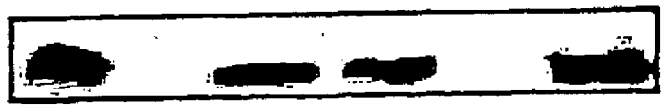
FADD ► 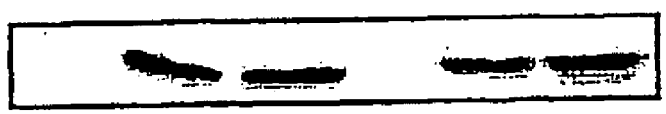
FIGURE 1B

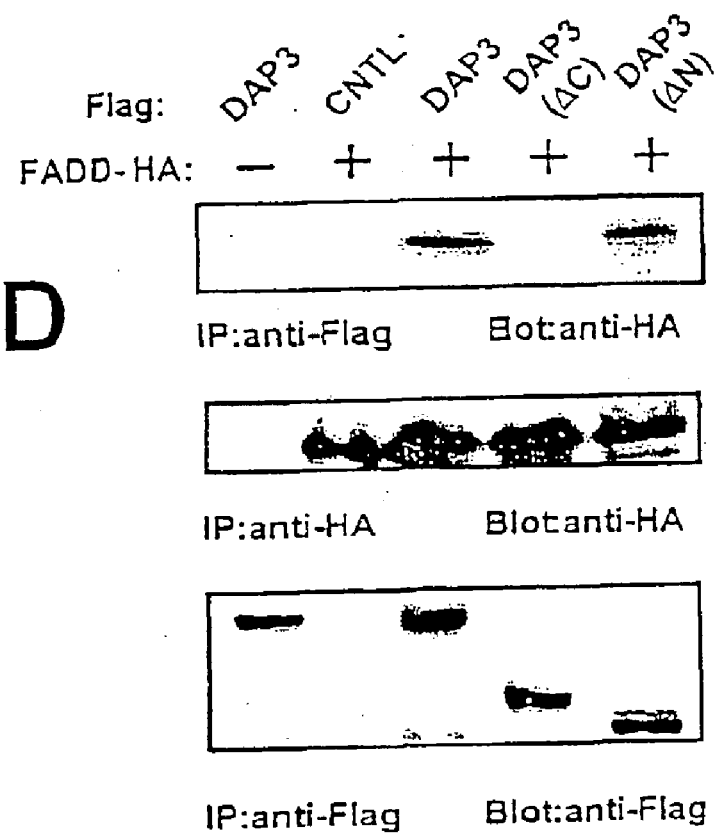
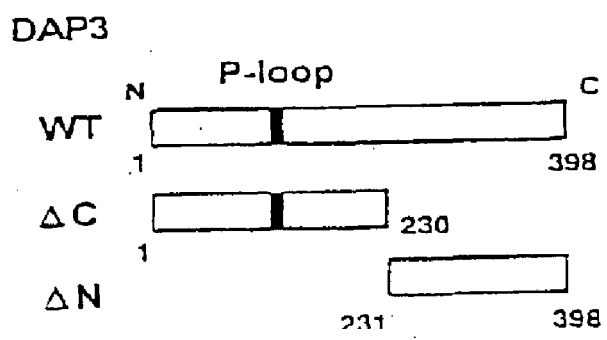
FIGURE 1D

```
a tgaacaaacc cataacacca tcaacatatg tgcgctgcct caatgttgga ctaattagga agctgtcaga
  ttttattgat cctcaagaag gatggaagaa gttagctgta gctattaaaa aaccatctgg
  tgatgataga tacaatcagt ttcacataag gagatttgaa gcattacttc aaactggaaa
  aagtcccact tctgaattac tgtttgactg gggcaccaca aattgcacag ttggtgatct
  tgtggatctt ttgatccaaa atgaattttt tgctcctgcg agtcttttgc tcccagatgc
  tgttcccaaa actgctaata cactaccttc taaagaagct ataacagttc agcaaaaaca
  gatgccttts tgtgacaaag acaggacatt gatgacacct gtgcagaatc ttgaacaaag
  ctatatgcca cctgactcct caagtccaga aaataaaagt ttagaagtta gtgatacacg
  ttttcacagt ttttcatttt atgaattgaa gaatgtcaca aataacttig atgaacgacc
  catttctgtt ggtggtaata aaatgggaga gggaggattt ggagttgtat ataaaggcta
  cgtaaataac acaactgtgg cagtgaagaa gcttgcagca atggttgaca ttactactga
  agaactgaaa cagcagtttg atcaagaaat aaaagtaatg gcaaagtgtc aacatgaaaa
  cttagtagaa ctacttggtt tctcaagtga tggagatgac ctctgcttag tatatgttta
  catgcctaat ggttcattgc tagacagact ctcttgcttg gatggtactc caccacttc
  ttggcacatg agatgcaaga ttgctcaggg tgcagctaat ggcatcaatt ttctacatga
  aaatcatcat attcatagag atattaaaag tgcaaatatc ttactggatg aagcttttac
  tgctaaaata tctgactttg gccttgcacg ggctictgag aagtttgccc agacagtcat
  gactagcaga attgtgggaa caacagctta tatggcacca gaagctttgc gtggagaaat
  aacacccaaa tctgatattt acagctttgg tgtggttta ctagaaataa taactggact
  tccagctgtg gatgaacacc gtgaacctca gttattgcta gatattaaag aagaaattga
  agatgaagaa aagacaattg aagattatat tgataaaaag atgaatgatg ctgattccac
  ttcagttgaa gctatgtact ctgttgctag tcaatgtctg catgaaaaga aaaataagag
  accagacatt aagaaggttc aacagctgct gcaagagatg acagcttctt aa
```

FIGURE 10A

```
MNKPITPSTYVRCLNVGLIRKLSDFIDPQEGWKKLAVAIKKPSG
DDRYNQFHIRRFEALLQTGKSPTSELLFDWGTTNCTVGDLVDLLIQNEFFAPASLLLP
DAVPKTANTLPSKEAITVQQKQMPFCDKDRTLMTPVQNLEQSYMPPDSSSPENKSLEV
SDTRFHSFSFYELKNVTNNFDERPISVGGNKMGEGGFGVVYKGYVNNTTVAVKKLAAM
VDITTEELKQQFDQEIKVMAKCQHENLVELLGFSSDGDDLCLVYVYMPNGSLLDRLSC
LDGTPPLSWHMRCKIAQGAANGINFLHENHHIHRDIKSANILLDEAFTAKISDFGLAR
ASEKFAQTVMTSRIVGTTAYMAPEALRGEITPKSDIYSFGVVLLEIITGLPAVDEHRE
PQLLLDIKEEIEDEEKTIEDYIDKKMNDADSTSVEAMYSVASQCLHEKKNKRPDIKKV
QQLLQEMTAS
```

FIGURE 10B

Death domains:
C. pneumoniae
DLWRQFALSLGVSEEELANHEFSQAAQDMVATFRRLCDMPQLAVGLGALYTYEIQIPQVCVEKIR
C. muridarum
DLWKQFVFALGVSSEELEAHEPSEAAKAKVATFMRWCTGDSLAAGVAALYSYESQIPCVAKEKIR
C. psittaci
DLWKNFAYALGVTEEELENHVPSAAAQKKVDTFLRWCTGDSLSAGVAALYTYESQIPTVAETKIS

FIGURE 11A

```
GI:7190927
ORGANISM  Chlamydia muridarum
ORIGIN
        1 mesrkgikev smnfldqlda iiqnkhmleh pfymkwskge ltkeqlqaya kdyylhikaf
       61 pkylsaihsr cddlearkll ldnlmdeeng ypnhidlwkq fvfalgvsse eleahepsea
      121 akakvatfmr wctgdslaag vaalysyesq ipcvakekir glieyfgfsn pedyayfteh
      181 eeadvrhare ekaliemlsr ddsdkvleas revtqslygf ldsflepatc chchka GI:7468151
ORGANISM  Chlamydophila pneumoniae [Chlamydia pneumoniae]
ORIGIN
        1 mtswielldk qiedqhmlkh efyqrwsegk lekqqlqaya kdyylhikaf pcylsalhar
       61 cddlqirrqi lenlmdeeag npnhidlwrq falslgvsee elanhefsqa aqdmvatfrr
      121 lcdmpqlavg lgalytyeiq ipqvcvekir glkeyfgvsa rgyayftvhq eadikhasee
      181 kemlqtlvgr enpdavlqgs qevldtlwnf lssfinstep csck
```

FIGURE 11B

```
                                                                ttaagc tttgtgacaa
6421 tgacaacatg ttgcaggctc taaaaatgaa tccaaaaagc cgtataaaga ttgtgtaact
6481 tctcgcgaag cttctaaaac tttgtcgcta tcatctctag acaacatctc aattaaggcc
6541 ttttcttccc tagcatgacg cacatcagct tcttcatgct ccgtgaaata agcataatct
6601 tcaggattag aaaagccaaa gtactcaatc aatccacgaa ttttttcttt agctacgcaa
6661 ggaatttgac tttcataaga atacaaagcc gctactcctg ctgctaaaga atccctgtg
6721 caccaccgca taaatgtcgc aaccttagct ttagctgctt cactgggttc atgagcttct
6781 agctcttctg aagacactcc aagagcaaac acaaattgtt tccataaatc aatatgatta
6841 ggataaccat tctcttcatc cattaagtta tctaataata acttgcgggc ttctaaatca
6901 tcacaacggc tatgaatagc agataaatat tttggaaaag ctttgatatg caaatagtaa
6961 tcttttgcgt atgcctgtaa ttgttctttt gtcagctctc cttttgacca cttcatgtaa
7021 aaagggtgtt ctaacatatg tttgttttga ataattgcat ctagctgatc taaaaaattc
7081 atgctcacct cttttattcc ttttcttgat tccac 7115
```

FIGURE 11C

| Myc-CTDD | + | − | + | − |
| Myc-XIAP | − | + | − | + |
| DR-5 | + | + | − | − |
| Flag-Casp 9 | − | − | + | + |

```
                           SEQUENCE LISTING

<160> NUMBER OF SEQ ID NOS: 62

<210> SEQ ID NO 1
<211> LENGTH: 210
<212> TYPE: DNA
<213> ORGANISM: Homo sapien
<220> FEATURE:
<221> NAME/KEY: CDS
<222> LOCATION: (1)...(210)

<400> SEQUENCE: 1 ctt tgg gga aga acc act ctg aaa aga gaa gat aaa agc ccg att gcc        48
Leu Trp Gly Arg Thr Thr Leu Lys Arg Glu Asp Lys Ser Pro Ile Ala
 1               5                  10                  15 ccc gag gaa tta gca ctt gtt cac aac ttg agg aaa atg atg aaa aat        96
Pro Glu Glu Leu Ala Leu Val His Asn Leu Arg Lys Met Met Lys Asn
            20                  25                  30 gat tgg cat gga ggc gcc att gtg tcg gct ttg agc cag act ggg tct       144
Asp Trp His Gly Gly Ala Ile Val Ser Ala Leu Ser Gln Thr Gly Ser
        35                  40                  45 ctc ttt aag ccc cgg aaa gcc tat ctg ccc cag gag ttg ctg gga aag       192
Leu Phe Lys Pro Arg Lys Ala Tyr Leu Pro Gln Glu Leu Leu Gly Lys
    50                  55                  60 gaa gga ttt gat gcc ctg                                               210
Glu Gly Phe Asp Ala Leu
 65                  70

<210> SEQ ID NO 2
<211> LENGTH: 70
<212> TYPE: PRT
<213> ORGANISM: Homo sapien

<400> SEQUENCE: 2

Leu Trp Gly Arg Thr Thr Leu Lys Arg Glu Asp Lys Ser Pro Ile Ala
 1               5                  10                  15

Pro Glu Glu Leu Ala Leu Val His Asn Leu Arg Lys Met Met Lys Asn
            20                  25                  30
```

-continued

```
Asp Trp His Gly Gly Ala Ile Val Ser Ala Leu Ser Gln Thr Gly Ser
         35                  40                  45

Leu Phe Lys Pro Arg Lys Ala Tyr Leu Pro Gln Glu Leu Leu Gly Lys
     50                  55                  60

Glu Gly Phe Asp Ala Leu
 65              70

<210> SEQ ID NO 3
<211> LENGTH: 297
<212> TYPE: DNA
<213> ORGANISM: Homo sapien
<220> FEATURE:
<221> NAME/KEY: CDS
<222> LOCATION: (1)...(297)

<400> SEQUENCE: 3 acc agt ttt gct tat cca gct ata cga tat ctt ctg tat gga gag aag      48
Thr Ser Phe Ala Tyr Pro Ala Ile Arg Tyr Leu Leu Tyr Gly Glu Lys
 1               5                  10                  15 gga aca gga aaa acc cta agt ctt tgc cat gtt att cat ttc tgt gca      96
Gly Thr Gly Lys Thr Leu Ser Leu Cys His Val Ile His Phe Cys Ala
             20                  25                  30 aaa cag gac tgg ctg ata cta cat att cca gat gct cat ctt tgg gtg     144
Lys Gln Asp Trp Leu Ile Leu His Ile Pro Asp Ala His Leu Trp Val
         35                  40                  45 aaa aat tgt cgg gat ctt ctg cag tcc agc tac aac aaa cag cgc ttt     192
Lys Asn Cys Arg Asp Leu Leu Gln Ser Ser Tyr Asn Lys Gln Arg Phe
     50                  55                  60 gat caa cct tta gag gct tca acc tgg ctg aag aat ttc aaa act aca     240
Asp Gln Pro Leu Glu Ala Ser Thr Trp Leu Lys Asn Phe Lys Thr Thr
 65              70                  75                  80 aat gag cgc ttc ctg aac cag ata aaa gtt caa gag aag tat gtc tgg     288
Asn Glu Arg Phe Leu Asn Gln Ile Lys Val Gln Glu Lys Tyr Val Trp
                 85                  90                  95 aat aag aga                                                          297
Asn Lys Arg <210> SEQ ID NO 4
<211> LENGTH: 99
<212> TYPE: PRT
<213> ORGANISM: Homo sapien

<400> SEQUENCE: 4

Thr Ser Phe Ala Tyr Pro Ala Ile Arg Tyr Leu Leu Tyr Gly Glu Lys
 1               5                  10                  15

Gly Thr Gly Lys Thr Leu Ser Leu Cys His Val Ile His Phe Cys Ala
             20                  25                  30

Lys Gln Asp Trp Leu Ile Leu His Ile Pro Asp Ala His Leu Trp Val
         35                  40                  45

Lys Asn Cys Arg Asp Leu Leu Gln Ser Ser Tyr Asn Lys Gln Arg Phe
     50                  55                  60

Asp Gln Pro Leu Glu Ala Ser Thr Trp Leu Lys Asn Phe Lys Thr Thr
 65              70                  75                  80

Asn Glu Arg Phe Leu Asn Gln Ile Lys Val Gln Glu Lys Tyr Val Trp
                 85                  90                  95

Asn Lys Arg
```

<210> SEQ ID NO 5
<211> LENGTH: 294
<212> TYPE: DNA
<213> ORGANISM: Homo sapien
<220> FEATURE:
<221> NAME/KEY: CDS
<222> LOCATION: (1)...(294)

<400> SEQUENCE: 5

```
aca tat gtg cgc tgc ctc aat gtt gga cta att agg aag ctg tca gat      48
Thr Tyr Val Arg Cys Leu Asn Val Gly Leu Ile Arg Lys Leu Ser Asp
 1               5                  10                  15 ttt att gat cct caa gaa gga tgg aag aag tta gct gta gct att aaa      96
Phe Ile Asp Pro Gln Glu Gly Trp Lys Lys Leu Ala Val Ala Ile Lys
             20                  25                  30 aaa cca tct ggt gat gat aga tac aat cag ttt cac ata agg aga ttt     144
Lys Pro Ser Gly Asp Asp Arg Tyr Asn Gln Phe His Ile Arg Arg Phe
         35                  40                  45 gaa gca tta ctt caa act gga aaa agt ccc act tct gaa tta ctg ttt     192
Glu Ala Leu Leu Gln Thr Gly Lys Ser Pro Thr Ser Glu Leu Leu Phe
     50                  55                  60 gac tgg ggc acc aca aat tgc aca gtt ggt gat ctt gtg gat ctt ttg     240
Asp Trp Gly Thr Thr Asn Cys Thr Val Gly Asp Leu Val Asp Leu Leu
 65                  70                  75                  80 atc caa aat gaa ttt ttt gct cct gcg agt ctt ttg ctc cca gat gct     288
Ile Gln Asn Glu Phe Phe Ala Pro Ala Ser Leu Leu Leu Pro Asp Ala
                 85                  90                  95 gtt ccc                                                              294
Val Pro
```

<210> SEQ ID NO 6
<211> LENGTH: 98
<212> TYPE: PRT
<213> ORGANISM: Homo sapien

<400> SEQUENCE: 6

```
Thr Tyr Val Arg Cys Leu Asn Val Gly Leu Ile Arg Lys Leu Ser Asp
 1               5                  10                  15

Phe Ile Asp Pro Gln Glu Gly Trp Lys Lys Leu Ala Val Ala Ile Lys
             20                  25                  30

Lys Pro Ser Gly Asp Asp Arg Tyr Asn Gln Phe His Ile Arg Arg Phe
         35                  40                  45

Glu Ala Leu Leu Gln Thr Gly Lys Ser Pro Thr Ser Glu Leu Leu Phe
     50                  55                  60

Asp Trp Gly Thr Thr Asn Cys Thr Val Gly Asp Leu Val Asp Leu Leu
 65                  70                  75                  80

Ile Gln Asn Glu Phe Phe Ala Pro Ala Ser Leu Leu Leu Pro Asp Ala
                 85                  90                  95

Val Pro
```

<210> SEQ ID NO 7
<211> LENGTH: 303
<212> TYPE: DNA
<213> ORGANISM: Homo sapien
<220> FEATURE:
<221> NAME/KEY: CDS
<222> LOCATION: (1)...(303)

<400> SEQUENCE: 7

```
tgg gag gag gat gag tgc ctg gac tac tac ggg atg ctg tcg ctt cac      48
Trp Glu Glu Asp Glu Cys Leu Asp Tyr Tyr Gly Met Leu Ser Leu His
 1               5                  10                  15
```

-continued

```
cgt atg ttc gag gtg gtg ggc ggg caa ctg acc gag tgc gag ctg gag      96
Arg Met Phe Glu Val Val Gly Gly Gln Leu Thr Glu Cys Glu Leu Glu
         20                  25                  30 ctc ctg gcc ttt ctg ctg gat gag gct cct ggc gcc gcc gga ggc tta     144
Leu Leu Ala Phe Leu Leu Asp Glu Ala Pro Gly Ala Ala Gly Gly Leu
     35                  40                  45 gcc cgg gcc cgc agc ggc cta gag ctc ctg ctg gag ctg gag cgc cgc     192
Ala Arg Ala Arg Ser Gly Leu Glu Leu Leu Leu Glu Leu Glu Arg Arg
 50                  55                  60 ggg cag tgc gac gag agc aac ctg cgg ctg ctg ggg caa ctc ctg cgc     240
Gly Gln Cys Asp Glu Ser Asn Leu Arg Leu Leu Gly Gln Leu Leu Arg
 65                  70                  75                  80 gtg ctg gcc cgc cac gac ctg ctg ccg cac ctg gcg cgc aag cgg cgc     288
Val Leu Ala Arg His Asp Leu Leu Pro His Leu Ala Arg Lys Arg Arg
             85                  90                  95 cgg cca gtg tct cca                                                 303
Arg Pro Val Ser Pro
            100
```

<210> SEQ ID NO 8
<211> LENGTH: 101
<212> TYPE: PRT
<213> ORGANISM: Homo sapien

<400> SEQUENCE: 8

```
Trp Glu Glu Asp Glu Cys Leu Asp Tyr Tyr Gly Met Leu Ser Leu His
 1               5                  10                  15

Arg Met Phe Glu Val Val Gly Gly Gln Leu Thr Glu Cys Glu Leu Glu
             20                  25                  30

Leu Leu Ala Phe Leu Leu Asp Glu Ala Pro Gly Ala Ala Gly Gly Leu
         35                  40                  45

Ala Arg Ala Arg Ser Gly Leu Glu Leu Leu Leu Glu Leu Glu Arg Arg
     50                  55                  60

Gly Gln Cys Asp Glu Ser Asn Leu Arg Leu Leu Gly Gln Leu Leu Arg
 65                  70                  75                  80

Val Leu Ala Arg His Asp Leu Leu Pro His Leu Ala Arg Lys Arg Arg
             85                  90                  95

Arg Pro Val Ser Pro
            100
```

<210> SEQ ID NO 9
<211> LENGTH: 195
<212> TYPE: DNA
<213> ORGANISM: Chlamydia trachomatis
<220> FEATURE:
<221> NAME/KEY: CDS
<222> LOCATION: (1)...(195)

<400> SEQUENCE: 9

```
gat ttg tgg aag cag ttt gtg ttt gct cta gga gtt act cca gaa gag      48
Asp Leu Trp Lys Gln Phe Val Phe Ala Leu Gly Val Thr Pro Glu Glu
 1               5                  10                  15 tta gag gct cat gag cct agt gaa gca gca aaa gcg aaa gta gct act      96
Leu Glu Ala His Glu Pro Ser Glu Ala Ala Lys Ala Lys Val Ala Thr
             20                  25                  30 ttc atg cgg tgg tgt aca gga gat tct tta gct gca gga gtg gct gct     144
Phe Met Arg Trp Cys Thr Gly Asp Ser Leu Ala Ala Gly Val Ala Ala
         35                  40                  45
```

```
ttg tat tct tat gag agt caa att cca cgt atc gct aga gag aaa att      192
Leu Tyr Ser Tyr Glu Ser Gln Ile Pro Arg Ile Ala Arg Glu Lys Ile
     50                  55                  60 cgt                                                                   195
Arg
 65

<210> SEQ ID NO 10
<211> LENGTH: 65
<212> TYPE: PRT
<213> ORGANISM: Chlamydia trachomatis

<400> SEQUENCE: 10

Asp Leu Trp Lys Gln Phe Val Phe Ala Leu Gly Val Thr Pro Glu Glu
 1               5                  10                  15

Leu Glu Ala His Glu Pro Ser Glu Ala Ala Lys Ala Lys Val Ala Thr
                20                  25                  30

Phe Met Arg Trp Cys Thr Gly Asp Ser Leu Ala Ala Gly Val Ala Ala
             35                  40                  45

Leu Tyr Ser Tyr Glu Ser Gln Ile Pro Arg Ile Ala Arg Glu Lys Ile
     50                  55                  60

Arg
 65

<210> SEQ ID NO 11
<211> LENGTH: 213
<212> TYPE: DNA
<213> ORGANISM: Mus musculus
<220> FEATURE:
<221> NAME/KEY: CDS
<222> LOCATION: (1)...(213)

<400> SEQUENCE: 11 cag cag cag gag gaa gtc cag cgg ctc ctg atg atg ggt gag cca gcc       48
Gln Gln Gln Glu Glu Val Gln Arg Leu Leu Met Met Gly Glu Pro Ala
 1               5                  10                  15 aag ggc tgg cag gag ctg gca ggc cac ctc ggc tac caa gct gag gct       96
Lys Gly Trp Gln Glu Leu Ala Gly His Leu Gly Tyr Gln Ala Glu Ala
                20                  25                  30 gtg gaa acc atg gcc tgt gac caa atg cca gcc tat acc ctg cta agg      144
Val Glu Thr Met Ala Cys Asp Gln Met Pro Ala Tyr Thr Leu Leu Arg
             35                  40                  45 aac tgg gct gcc caa gaa ggc aat aga gct acc ctc aga gtg ctg gag      192
Asn Trp Ala Ala Gln Glu Gly Asn Arg Ala Thr Leu Arg Val Leu Glu
     50                  55                  60 gat gct ctg gct gcc ata ggc                                          213
Asp Ala Leu Ala Ala Ile Gly
 65                  70

<210> SEQ ID NO 12
<211> LENGTH: 71
<212> TYPE: PRT
<213> ORGANISM: Mus musculus

<400> SEQUENCE: 12

Gln Gln Gln Glu Glu Val Gln Arg Leu Leu Met Met Gly Glu Pro Ala
 1               5                  10                  15

Lys Gly Trp Gln Glu Leu Ala Gly His Leu Gly Tyr Gln Ala Glu Ala
                20                  25                  30

Val Glu Thr Met Ala Cys Asp Gln Met Pro Ala Tyr Thr Leu Leu Arg
             35                  40                  45
```

```
Asn Trp Ala Ala Gln Glu Gly Asn Arg Ala Thr Leu Arg Val Leu Glu
 50                  55                  60

Asp Ala Leu Ala Ala Ile Gly
 65                  70

<210> SEQ ID NO 13
<211> LENGTH: 1605
<212> TYPE: DNA
<213> ORGANISM: Homo sapien
<220> FEATURE:
<221> NAME/KEY: CDS
<222> LOCATION: (74)...(1267)

<400> SEQUENCE: 13
gaattccgcc ggccccaggc agcgtgtgtc ggtcgcctag gctggagaac tagtcctcga      60
ctcacgtgca agg atg atg ctg aaa gga ata aca agg ctt atc tct agg       109
             Met Met Leu Lys Gly Ile Thr Arg Leu Ile Ser Arg
               1               5                  10 atc cat aag ttg gac cct ggg cgt ttt tta cac atg ggg acc cag gct      157
Ile His Lys Leu Asp Pro Gly Arg Phe Leu His Met Gly Thr Gln Ala
             15                  20                  25 cgc caa agc att gct gct cac cta gat aac cag gtt cca gtt gag agt      205
Arg Gln Ser Ile Ala Ala His Leu Asp Asn Gln Val Pro Val Glu Ser
 30                  35                  40 ccg aga gct att tcc cgc acc aat gag aat gac ccg gcc aag cat ggg      253
Pro Arg Ala Ile Ser Arg Thr Asn Glu Asn Asp Pro Ala Lys His Gly
 45                  50                  55                  60 gat cag cac gag ggt cag cac tac aac atc tcc ccc cag gat ttg gag      301
Asp Gln His Glu Gly Gln His Tyr Asn Ile Ser Pro Gln Asp Leu Glu
                 65                  70                  75 act gta ttt ccc cat ggc ctt cct cct cgc ttt gtg atg cag gtg aag      349
Thr Val Phe Pro His Gly Leu Pro Pro Arg Phe Val Met Gln Val Lys
             80                  85                  90 aca ttc agt gaa gct tgc ctg atg gta agg aaa cca gcc cta gaa ctt      397
Thr Phe Ser Glu Ala Cys Leu Met Val Arg Lys Pro Ala Leu Glu Leu
         95                 100                 105 ctg cat tac ctg aaa aac acc agt ttt gct tat cca gct ata cga tat      445
Leu His Tyr Leu Lys Asn Thr Ser Phe Ala Tyr Pro Ala Ile Arg Tyr
    110                 115                 120 ctt ctg tat gga gag aag gga aca gga aaa acc cta agt ctt tgc cat      493
Leu Leu Tyr Gly Glu Lys Gly Thr Gly Lys Thr Leu Ser Leu Cys His
125                 130                 135                 140 gtt att cat ttc tgt gca aaa cag gac tgg ctg ata cta cat att cca      541
Val Ile His Phe Cys Ala Lys Gln Asp Trp Leu Ile Leu His Ile Pro
                145                 150                 155 gat gct cat ctt tgg gtg aaa aat tgt cgg gat ctt ctg cag tcc agc      589
Asp Ala His Leu Trp Val Lys Asn Cys Arg Asp Leu Leu Gln Ser Ser
            160                 165                 170 tac aac aaa cag cgc ttt gat caa cct tta gag gct tca acc tgg ctg      637
Tyr Asn Lys Gln Arg Phe Asp Gln Pro Leu Glu Ala Ser Thr Trp Leu
        175                 180                 185 aag aat ttc aaa act aca aat gag cgc ttc ctg aac cag ata aaa gtt      685
Lys Asn Phe Lys Thr Thr Asn Glu Arg Phe Leu Asn Gln Ile Lys Val
    190                 195                 200 caa gag aag tat gtc tgg aat aag aga gaa agc act gag aaa ggg agt      733
Gln Glu Lys Tyr Val Trp Asn Lys Arg Glu Ser Thr Glu Lys Gly Ser
205                 210                 215                 220 cct ctg gga gaa gtg gtt gaa cag ggc ata aca cgg gtg agg aac gcc      781
Pro Leu Gly Glu Val Val Glu Gln Gly Ile Thr Arg Val Arg Asn Ala
                225                 230                 235
```

-continued

```
aca gat gca gtt gga att gtg ctg aaa gag cta aag agg caa agt tct      829
Thr Asp Ala Val Gly Ile Val Leu Lys Glu Leu Lys Arg Gln Ser Ser
        240                 245                 250 ttg ggt atg ttt cac ctc cta gtg gcc gtg gat gga atc aat gct ctt      877
Leu Gly Met Phe His Leu Leu Val Ala Val Asp Gly Ile Asn Ala Leu
    255                 260                 265 tgg gga aga acc act ctg aaa aga gaa gat aaa agc ccg att gcc ccc      925
Trp Gly Arg Thr Thr Leu Lys Arg Glu Asp Lys Ser Pro Ile Ala Pro
270                 275                 280 gag gaa tta gca ctt gtt cac aac ttg agg aaa atg atg aaa aat gat      973
Glu Glu Leu Ala Leu Val His Asn Leu Arg Lys Met Met Lys Asn Asp
285                 290                 295                 300 tgg cat gga ggc gcc att gtg tcg gct ttg agc cag act ggg tct ctc     1021
Trp His Gly Gly Ala Ile Val Ser Ala Leu Ser Gln Thr Gly Ser Leu
                305                 310                 315 ttt aag ccc cgg aaa gcc tat ctg ccc cag gag ttg ctg gga aag gaa     1069
Phe Lys Pro Arg Lys Ala Tyr Leu Pro Gln Glu Leu Leu Gly Lys Glu
            320                 325                 330 gga ttt gat gcc ctg gat ccc ttt att ccc atc ctg gtt tcc aac tat     1117
Gly Phe Asp Ala Leu Asp Pro Phe Ile Pro Ile Leu Val Ser Asn Tyr
        335                 340                 345 aac cca aag gaa ttt gaa agt tgt att cag tat tat ttg gaa aac aat     1165
Asn Pro Lys Glu Phe Glu Ser Cys Ile Gln Tyr Tyr Leu Glu Asn Asn
350                 355                 360 tgg ctt caa cat gag aaa gct cct aca gaa gaa ggg aaa aaa gag ctg     1213
Trp Leu Gln His Glu Lys Ala Pro Thr Glu Glu Gly Lys Lys Glu Leu
365                 370                 375                 380 ctg ttc cta agt aac gcg aac ccc tcg ctg ctg gag cgg cac tgt gcc     1261
Leu Phe Leu Ser Asn Ala Asn Pro Ser Leu Leu Glu Arg His Cys Ala
                385                 390                 395 tac ctc taagccaaga tcacagcatg tgaggaagac agtggacatc tgctttatgc     1317
Tyr Leu tggacccagt aagatgagga agtcgggcag tacacaggaa gaggagccag gcccttgtac     1377
ctatgggatt ggacaggact gcagttggct ctggacctgc attaaaatgg gtttcactgt     1437
gaatgcgtga caataagata ttcccttgtt cctaaaactt tatatcagtt tattggatgt     1497 ggttttttcac atttaagata attatggctc ttttcctaaa aaataaaata tctttctaaa     1557
aaaaaaaaaa aaaaaaaaaa aaaaaaaaaa aaaaaaaaaa aaaaaaaa                   1605
```

<210> SEQ ID NO 14
<211> LENGTH: 398
<212> TYPE: PRT
<213> ORGANISM: Homo sapien

<400> SEQUENCE: 14

```
Met Met Leu Lys Gly Ile Thr Arg Leu Ile Ser Arg Ile His Lys Leu
1               5                   10                  15

Asp Pro Gly Arg Phe Leu His Met Gly Thr Gln Ala Arg Gln Ser Ile
            20                  25                  30

Ala Ala His Leu Asp Asn Gln Val Pro Val Glu Ser Pro Arg Ala Ile
        35                  40                  45

Ser Arg Thr Asn Glu Asn Asp Pro Ala Lys His Gly Asp Gln His Glu
    50                  55                  60

Gly Gln His Tyr Asn Ile Ser Pro Gln Asp Leu Glu Thr Val Phe Pro
65                  70                  75                  80

His Gly Leu Pro Pro Arg Phe Val Met Gln Val Lys Thr Phe Ser Glu
                85                  90                  95
```

```
Ala Cys Leu Met Val Arg Lys Pro Ala Leu Glu Leu Leu His Tyr Leu
            100                 105                 110

Lys Asn Thr Ser Phe Ala Tyr Pro Ala Ile Arg Tyr Leu Leu Tyr Gly
            115                 120                 125

Glu Lys Gly Thr Gly Lys Thr Leu Ser Leu Cys His Val Ile His Phe
130                 135                 140

Cys Ala Lys Gln Asp Trp Leu Ile Leu His Ile Pro Asp Ala His Leu
145                 150                 155                 160

Trp Val Lys Asn Cys Arg Asp Leu Leu Gln Ser Ser Tyr Asn Lys Gln
                165                 170                 175

Arg Phe Asp Gln Pro Leu Glu Ala Ser Thr Trp Leu Lys Asn Phe Lys
            180                 185                 190

Thr Thr Asn Glu Arg Phe Leu Asn Gln Ile Lys Val Gln Glu Lys Tyr
            195                 200                 205

Val Trp Asn Lys Arg Glu Ser Thr Glu Lys Gly Ser Pro Leu Gly Glu
210                 215                 220

Val Val Glu Gln Gly Ile Thr Arg Val Arg Asn Ala Thr Asp Ala Val
225                 230                 235                 240

Gly Ile Val Leu Lys Glu Leu Lys Arg Gln Ser Ser Leu Gly Met Phe
                245                 250                 255

His Leu Leu Val Ala Val Asp Gly Ile Asn Ala Leu Trp Gly Arg Thr
            260                 265                 270

Thr Leu Lys Arg Glu Asp Lys Ser Pro Ile Ala Pro Glu Glu Leu Ala
        275                 280                 285

Leu Val His Asn Leu Arg Lys Met Met Lys Asn Asp Trp His Gly Gly
            290                 295                 300

Ala Ile Val Ser Ala Leu Ser Gln Thr Gly Ser Leu Phe Lys Pro Arg
305                 310                 315                 320

Lys Ala Tyr Leu Pro Gln Glu Leu Leu Gly Lys Glu Gly Phe Asp Ala
                325                 330                 335

Leu Asp Pro Phe Ile Pro Ile Leu Val Ser Asn Tyr Asn Pro Lys Glu
            340                 345                 350

Phe Glu Ser Cys Ile Gln Tyr Tyr Leu Glu Asn Asn Trp Leu Gln His
            355                 360                 365

Glu Lys Ala Pro Thr Glu Glu Gly Lys Lys Glu Leu Leu Phe Leu Ser
        370                 375                 380

Asn Ala Asn Pro Ser Leu Leu Glu Arg His Cys Ala Tyr Leu
385                 390                 395

<210> SEQ ID NO 15
<211> LENGTH: 1383
<212> TYPE: DNA
<213> ORGANISM: Homo sapien
<220> FEATURE:
<221> NAME/KEY: CDS
<222> LOCATION: (1)...(1380)

<400> SEQUENCE: 15 atg aac aaa ccc ata aca cca tca aca tat gtg cgc tgc ctc aat gtt     48
Met Asn Lys Pro Ile Thr Pro Ser Thr Tyr Val Arg Cys Leu Asn Val
  1               5                  10                  15 gga cta att agg aag ctg tca gat ttt att gat cct caa gaa gga tgg     96
Gly Leu Ile Arg Lys Leu Ser Asp Phe Ile Asp Pro Gln Glu Gly Trp
             20                  25                  30 aag aag tta gct gta gct att aaa aaa cca tct ggt gat gat aga tac    144
Lys Lys Leu Ala Val Ala Ile Lys Lys Pro Ser Gly Asp Asp Arg Tyr
         35                  40                  45
```

-continued

| | |
|---|---|
| aat cag ttt cac ata agg aga ttt gaa gca tta ctt caa act gga aaa<br>Asn Gln Phe His Ile Arg Arg Phe Glu Ala Leu Leu Gln Thr Gly Lys<br>50 55 60 | 192 |
| agt ccc act tct gaa tta ctg ttt gac tgg ggc acc aca aat tgc aca<br>Ser Pro Thr Ser Glu Leu Leu Phe Asp Trp Gly Thr Thr Asn Cys Thr<br>65 70 75 80 | 240 |
| gtt ggt gat ctt gtg gat ctt ttg atc caa aat gaa ttt ttt gct cct<br>Val Gly Asp Leu Val Asp Leu Leu Ile Gln Asn Glu Phe Phe Ala Pro<br>85 90 95 | 288 |
| gcg agt ctt ttg ctc cca gat gct gtt ccc aaa act gct aat aca cta<br>Ala Ser Leu Leu Leu Pro Asp Ala Val Pro Lys Thr Ala Asn Thr Leu<br>100 105 110 | 336 |
| cct tct aaa gaa gct ata aca gtt cag caa aaa cag atg cct ttc tgt<br>Pro Ser Lys Glu Ala Ile Thr Val Gln Gln Lys Gln Met Pro Phe Cys<br>115 120 125 | 384 |
| gac aaa gac agg aca ttg atg aca cct gtg cag aat ctt gaa caa agc<br>Asp Lys Asp Arg Thr Leu Met Thr Pro Val Gln Asn Leu Glu Gln Ser<br>130 135 140 | 432 |
| tat atg cca cct gac tcc tca agt cca gaa aat aaa agt tta gaa gtt<br>Tyr Met Pro Pro Asp Ser Ser Ser Pro Glu Asn Lys Ser Leu Glu Val<br>145 150 155 160 | 480 |
| agt gat aca cgt ttt cac agt ttt tca ttt tat gaa ttg aag aat gtc<br>Ser Asp Thr Arg Phe His Ser Phe Ser Phe Tyr Glu Leu Lys Asn Val<br>165 170 175 | 528 |
| aca aat aac ttt gat gaa cga ccc att tct gtt ggt ggt aat aaa atg<br>Thr Asn Asn Phe Asp Glu Arg Pro Ile Ser Val Gly Gly Asn Lys Met<br>180 185 190 | 576 |
| gga gag gga gga ttt gga gtt gta tat aaa ggc tac gta aat aac aca<br>Gly Glu Gly Gly Phe Gly Val Val Tyr Lys Gly Tyr Val Asn Asn Thr<br>195 200 205 | 624 |
| act gtg gca gtg aag aag ctt gca gca atg gtt gac att act act gaa<br>Thr Val Ala Val Lys Lys Leu Ala Ala Met Val Asp Ile Thr Thr Glu<br>210 215 220 | 672 |
| gaa ctg aaa cag cag ttt gat caa gaa ata aaa gta atg gca aag tgt<br>Glu Leu Lys Gln Gln Phe Asp Gln Glu Ile Lys Val Met Ala Lys Cys<br>225 230 235 240 | 720 |
| caa cat gaa aac tta gta gaa cta ctt ggt ttc tca agt gat gga gat<br>Gln His Glu Asn Leu Val Glu Leu Leu Gly Phe Ser Ser Asp Gly Asp<br>245 250 255 | 768 |
| gac ctc tgc tta gta tat gtt tac atg cct aat ggt tca ttg cta gac<br>Asp Leu Cys Leu Val Tyr Val Tyr Met Pro Asn Gly Ser Leu Leu Asp<br>260 265 270 | 816 |
| aga ctc tct tgc ttg gat ggt act cca cca ctt tct tgg cac atg aga<br>Arg Leu Ser Cys Leu Asp Gly Thr Pro Pro Leu Ser Trp His Met Arg<br>275 280 285 | 864 |
| tgc aag att gct cag ggt gca gct aat ggc atc aat ttt cta cat gaa<br>Cys Lys Ile Ala Gln Gly Ala Ala Asn Gly Ile Asn Phe Leu His Glu<br>290 295 300 | 912 |
| aat cat cat att cat aga gat att aaa agt gca aat atc tta ctg gat<br>Asn His His Ile His Arg Asp Ile Lys Ser Ala Asn Ile Leu Leu Asp<br>305 310 315 320 | 960 |
| gaa gct ttt act gct aaa ata tct gac ttt ggc ctt gca cgg gct tct<br>Glu Ala Phe Thr Ala Lys Ile Ser Asp Phe Gly Leu Ala Arg Ala Ser<br>325 330 335 | 1008 |
| gag aag ttt gcc cag aca gtc atg act agc aga att gtg gga aca aca<br>Glu Lys Phe Ala Gln Thr Val Met Thr Ser Arg Ile Val Gly Thr Thr<br>340 345 350 | 1056 |
| gct tat atg gca cca gaa gct ttg cgt gga gaa ata aca ccc aaa tct<br>Ala Tyr Met Ala Pro Glu Ala Leu Arg Gly Glu Ile Thr Pro Lys Ser<br>355 360 365 | 1104 |

-continued

```
gat att tac agc ttt ggt gtg gtt tta cta gaa ata ata act gga ctt    1152
Asp Ile Tyr Ser Phe Gly Val Val Leu Leu Glu Ile Ile Thr Gly Leu
    370                 375                 380 cca gct gtg gat gaa cac cgt gaa cct cag tta ttg cta gat att aaa    1200
Pro Ala Val Asp Glu His Arg Glu Pro Gln Leu Leu Leu Asp Ile Lys
385                 390                 395                 400 gaa att gaa gat gaa gaa aag aca att gaa gat tat att gat aaa        1248
Glu Glu Ile Glu Asp Glu Glu Lys Thr Ile Glu Asp Tyr Ile Asp Lys
                405                 410                 415 aag atg aat gat gct gat tcc act tca gtt gaa gct atg tac tct gtt    1296
Lys Met Asn Asp Ala Asp Ser Thr Ser Val Glu Ala Met Tyr Ser Val
                420                 425                 430 gct agt caa tgt ctg cat gaa aag aaa aat aag aga cca gac att aag    1344
Ala Ser Gln Cys Leu His Glu Lys Lys Asn Lys Arg Pro Asp Ile Lys
            435                 440                 445 aag gtt caa cag ctg ctg caa gag atg aca gct tct taa                1383
Lys Val Gln Gln Leu Leu Gln Glu Met Thr Ala Ser
450                 455                 460

<210> SEQ ID NO 16
<211> LENGTH: 460
<212> TYPE: PRT
<213> ORGANISM: Homo sapien

<400> SEQUENCE: 16

Met Asn Lys Pro Ile Thr Pro Ser Thr Tyr Val Arg Cys Leu Asn Val
 1               5                  10                  15

Gly Leu Ile Arg Lys Leu Ser Asp Phe Ile Asp Pro Gln Glu Gly Trp
            20                  25                  30

Lys Lys Leu Ala Val Ala Ile Lys Lys Pro Ser Gly Asp Asp Arg Tyr
        35                  40                  45

Asn Gln Phe His Ile Arg Arg Phe Glu Ala Leu Leu Gln Thr Gly Lys
    50                  55                  60

Ser Pro Thr Ser Glu Leu Leu Phe Asp Trp Gly Thr Thr Asn Cys Thr
65                  70                  75                  80

Val Gly Asp Leu Val Asp Leu Leu Ile Gln Asn Glu Phe Phe Ala Pro
                85                  90                  95

Ala Ser Leu Leu Leu Pro Asp Ala Val Pro Lys Thr Ala Asn Thr Leu
            100                 105                 110

Pro Ser Lys Glu Ala Ile Thr Val Gln Gln Lys Gln Met Pro Phe Cys
        115                 120                 125

Asp Lys Asp Arg Thr Leu Met Thr Pro Val Gln Asn Leu Glu Gln Ser
    130                 135                 140

Tyr Met Pro Pro Asp Ser Ser Pro Glu Asn Lys Ser Leu Glu Val
145                 150                 155                 160

Ser Asp Thr Arg Phe His Ser Phe Ser Phe Tyr Glu Leu Lys Asn Val
                165                 170                 175

Thr Asn Asn Phe Asp Glu Arg Pro Ile Ser Val Gly Gly Asn Lys Met
            180                 185                 190

Gly Glu Gly Gly Phe Gly Val Val Tyr Lys Gly Tyr Val Asn Asn Thr
        195                 200                 205

Thr Val Ala Val Lys Lys Leu Ala Ala Met Val Asp Ile Thr Thr Glu
    210                 215                 220

Glu Leu Lys Gln Gln Phe Asp Gln Glu Ile Lys Val Met Ala Lys Cys
225                 230                 235                 240

Gln His Glu Asn Leu Val Glu Leu Leu Gly Phe Ser Ser Asp Gly Asp
                245                 250                 255
```

-continued

```
Asp Leu Cys Leu Val Tyr Val Tyr Met Pro Asn Gly Ser Leu Leu Asp
            260                 265                 270

Arg Leu Ser Cys Leu Asp Gly Thr Pro Pro Leu Ser Trp His Met Arg
        275                 280                 285

Cys Lys Ile Ala Gln Gly Ala Ala Asn Gly Ile Asn Phe Leu His Glu
    290                 295                 300

Asn His His Ile His Arg Asp Ile Lys Ser Ala Asn Ile Leu Leu Asp
305                 310                 315                 320

Glu Ala Phe Thr Ala Lys Ile Ser Asp Phe Gly Leu Ala Arg Ala Ser
                325                 330                 335

Glu Lys Phe Ala Gln Thr Val Met Thr Ser Arg Ile Val Gly Thr Thr
            340                 345                 350

Ala Tyr Met Ala Pro Glu Ala Leu Arg Gly Glu Ile Thr Pro Lys Ser
        355                 360                 365

Asp Ile Tyr Ser Phe Gly Val Val Leu Leu Glu Ile Ile Thr Gly Leu
    370                 375                 380

Pro Ala Val Asp Glu His Arg Glu Pro Gln Leu Leu Asp Ile Lys
385                 390                 395                 400

Glu Glu Ile Glu Asp Glu Lys Thr Ile Glu Asp Tyr Ile Asp Lys
                405                 410                 415

Lys Met Asn Asp Ala Asp Ser Thr Ser Val Glu Ala Met Tyr Ser Val
            420                 425                 430

Ala Ser Gln Cys Leu His Glu Lys Lys Asn Lys Arg Pro Asp Ile Lys
        435                 440                 445

Lys Val Gln Gln Leu Leu Gln Glu Met Thr Ala Ser
    450                 455                 460

<210> SEQ ID NO 17
<211> LENGTH: 1924
<212> TYPE: DNA
<213> ORGANISM: Homo sapien
<220> FEATURE:
<221> NAME/KEY: CDS
<222> LOCATION: (91)...(1044)
<221> NAME/KEY: misc_feature
<222> LOCATION: (1)...(1900)
<223> OTHER INFORMATION: n = A,T,C or G

<400> SEQUENCE: 17
ccaaaacaag tggctgcggc gtcgcccagg agtcatcgga cgccagaatc tggccgggtt      60
ctgagcttgt tccgcctccc tccccgggga atg gcg cta tcc ggg tcg acc ccg     114
                                Met Ala Leu Ser Gly Ser Thr Pro
                                 1               5 gcc ccg tgc tgg gag gag gat gag tgc ctg gac tac tac ggg atg ctg      162
Ala Pro Cys Trp Glu Glu Asp Glu Cys Leu Asp Tyr Tyr Gly Met Leu
    10                  15                  20 tcg ctt cac cgt atg ttc gag gtg gtg ggc ggg caa ctg acc gag tgc      210
Ser Leu His Arg Met Phe Glu Val Val Gly Gly Gln Leu Thr Glu Cys
25                  30                  35                  40 gag ctg gag ctc ctg gcc ttt ctg ctg gat gag gct cct ggc gcc gcc      258
Glu Leu Glu Leu Leu Ala Phe Leu Leu Asp Glu Ala Pro Gly Ala Ala
                45                  50                  55 gga ggc tta gcc cgg gcc cgc agc ggc cta gag ctc ctg ctg gag ctg      306
Gly Gly Leu Ala Arg Ala Arg Ser Gly Leu Glu Leu Leu Leu Glu Leu
            60                  65                  70 gag cgc cgc ggg cag tgc gac gag agc aac ctg cgg ctg ctg ggg caa      354
Glu Arg Arg Gly Gln Cys Asp Glu Ser Asn Leu Arg Leu Leu Gly Gln
        75                  80                  85
```

-continued

| | |
|---|---|
| ctc ctg cgc gtg ctg gcc cgc cac gac ctg ctg ccg cac ctg gcg cgc<br>Leu Leu Arg Val Leu Ala Arg His Asp Leu Leu Pro His Leu Ala Arg<br>    90                            95                          100 | 402 |
| aag cgg cgc cgg cca gtg tct cca gaa cgc tat agc tat ggc acc tcc<br>Lys Arg Arg Arg Pro Val Ser Pro Glu Arg Tyr Ser Tyr Gly Thr Ser<br>105                        110                      115                      120 | 450 |
| agc tct tca aag agg aca gag ggt agc tgc cgt cgc cgt cgg cag tca<br>Ser Ser Ser Lys Arg Thr Glu Gly Ser Cys Arg Arg Arg Gln Ser<br>                          125                      130                      135 | 498 |
| agc agt tct gca aat tct cag cag ggt cag tgg gag aca ggc tcc ccc<br>Ser Ser Ser Ala Asn Ser Gln Gln Gly Gln Trp Glu Thr Gly Ser Pro<br>                140                      145                      150 | 546 |
| cca acc aag cgg cag cgg cgg agt cgg ggc cgg ccc agt ggt ggt gcc<br>Pro Thr Lys Arg Gln Arg Arg Ser Arg Gly Arg Pro Ser Gly Gly Ala<br>            155                      160                      165 | 594 |
| aga cgg cgg cgg aga ggg gcc cca gcc gca ccc cag cag cag tca gag<br>Arg Arg Arg Arg Arg Gly Ala Pro Ala Ala Pro Gln Gln Gln Ser Glu<br>    170                      175                      180 | 642 |
| ccc gcc aga cct tcc tct gaa ggc aaa gtg acc tgt gac atc cgg ctc<br>Pro Ala Arg Pro Ser Ser Glu Gly Lys Val Thr Cys Asp Ile Arg Leu<br>185                        190                      195                      200 | 690 |
| cgg gtt cga gca gag tac tgc gag cat ggg cca gcc ttg gag cag ggc<br>Arg Val Arg Ala Glu Tyr Cys Glu His Gly Pro Ala Leu Glu Gln Gly<br>                      205                      210                      215 | 738 |
| gtg gca tcc cgg cgg ccc cag gcg ctg gcg cgg cag ctg gac gtg ttt<br>Val Ala Ser Arg Arg Pro Gln Ala Leu Ala Arg Gln Leu Asp Val Phe<br>                220                      225                      230 | 786 |
| ggg cag gcc acc gca gtg ctg cgc tca agg gac ctg ggc tct gtg gtt<br>Gly Gln Ala Thr Ala Val Leu Arg Ser Arg Asp Leu Gly Ser Val Val<br>            235                      240                      245 | 834 |
| tgt gac atc aag ttc tca gag ctc tcc tat ctg gac gcc ttc tgg ggc<br>Cys Asp Ile Lys Phe Ser Glu Leu Ser Tyr Leu Asp Ala Phe Trp Gly<br>250                        255                      260 | 882 |
| gac tac ctg agt ggc gcc ctg ctg cag gcc ctg cgg ggc gtg ttc ctg<br>Asp Tyr Leu Ser Gly Ala Leu Leu Gln Ala Leu Arg Gly Val Phe Leu<br>265                        270                      275                      280 | 930 |
| act gag gcc ctg cga gag gct gtg ggc cgg gag gct gtt cgc ctg ctg<br>Thr Glu Ala Leu Arg Glu Ala Val Gly Arg Glu Ala Val Arg Leu Leu<br>                      285                      290                      295 | 978 |
| gtc agt gtg gat gag gct gac tat gag gct ggc cgg cgc cgc ctg ttg<br>Val Ser Val Asp Glu Ala Asp Tyr Glu Ala Gly Arg Arg Arg Leu Leu<br>            300                      305                      310 | 1026 |
| ctg atg gag gag gaa ggg gggcggcgcc cgacagaggc ctcctgatcc<br>Leu Met Glu Glu Glu Gly<br>            315 | 1074 |
| aggactggca ggattgatcc cacctccaag tctccgggcc accttctcct gggaggacga | 1134 |
| ccatctctac ccctagagga ctgtcactct agcatctttg aggactgcga caggaccggg | 1194 |
| acagcaggcc ccttgacagc ccctcccaca ggatgtgggc tctgaggcct aaaccatttc | 1254 |
| cagctgagtt tccttcccag actcctccta ccccaggtgt gccccattcg cctccggacg | 1314 |
| cggcggctgg gcctgtatct cagaagggag gggcacagct acacactcac caaaggcccc | 1374 |
| cctgcacatt gtatctctga tcttgggctg tttgcactgt cacaggtgca cacactcgct | 1434 |
| catgctcaca ctgcccctgc tgagatcttc ctggcctct gccctggcct gttcccagca | 1494 |
| cacactttt tggcctaagg gcttcttct caggacttt aatttgacca ccaacccaaa | 1554 |
| ctggggtttc agccaaaatc agtgggcact ggagctgggg tgcacatggg gcctgctcac | 1614 |
| cttgcccaca natttccagc cagccagggc cctgcccagc ttcaatttac agacctgact | 1674 |

```
ntcctcacct tccccctgc tgtccagagc tgaacataga cttgcacttg gatgtcacct    1734
ggagtgtcac atgggagtgt tatggcagca tcataccaag gcctactgtt gcacatgggg    1794
ccaaaaccag taaacagcca ccttnttgga agggaatgc aaaggctttg gggtgatgg     1854 aaaagacctt ttacaaatga taccaattaa actgccctgg aaagggcata ggtgggcaaa    1914
aaaaaaaaaa                                                          1924
```

<210> SEQ ID NO 18
<211> LENGTH: 318
<212> TYPE: PRT
<213> ORGANISM: Homo sapien

<400> SEQUENCE: 18

```
Met Ala Leu Ser Gly Ser Thr Pro Ala Pro Cys Trp Glu Glu Asp Glu
 1               5                  10                  15

Cys Leu Asp Tyr Tyr Gly Met Leu Ser Leu His Arg Met Phe Glu Val
            20                  25                  30

Val Gly Gly Gln Leu Thr Glu Cys Glu Leu Glu Leu Leu Ala Phe Leu
        35                  40                  45

Leu Asp Glu Ala Pro Gly Ala Ala Gly Gly Leu Ala Arg Ala Arg Ser
    50                  55                  60

Gly Leu Glu Leu Leu Glu Leu Glu Arg Arg Gly Gln Cys Asp Glu
65                  70                  75                  80

Ser Asn Leu Arg Leu Leu Gly Gln Leu Leu Arg Val Leu Ala Arg His
                85                  90                  95

Asp Leu Leu Pro His Leu Ala Arg Lys Arg Arg Pro Val Ser Pro
            100                 105                 110

Glu Arg Tyr Ser Tyr Gly Thr Ser Ser Ser Ser Lys Arg Thr Glu Gly
        115                 120                 125

Ser Cys Arg Arg Arg Gln Ser Ser Ser Ala Asn Ser Gln Gln
    130                 135                 140

Gly Gln Trp Glu Thr Gly Ser Pro Pro Thr Lys Arg Gln Arg Arg Ser
145                 150                 155                 160

Arg Gly Arg Pro Ser Gly Gly Ala Arg Arg Arg Arg Gly Ala Pro
                165                 170                 175

Ala Ala Pro Gln Gln Gln Ser Glu Pro Ala Arg Pro Ser Ser Glu Gly
            180                 185                 190

Lys Val Thr Cys Asp Ile Arg Leu Arg Val Arg Ala Glu Tyr Cys Glu
        195                 200                 205

His Gly Pro Ala Leu Glu Gln Gly Val Ala Ser Arg Arg Pro Gln Ala
    210                 215                 220

Leu Ala Arg Gln Leu Asp Val Phe Gly Gln Ala Thr Ala Val Leu Arg
225                 230                 235                 240

Ser Arg Asp Leu Gly Ser Val Val Cys Asp Ile Lys Phe Ser Glu Leu
                245                 250                 255

Ser Tyr Leu Asp Ala Phe Trp Gly Asp Tyr Leu Ser Gly Ala Leu Leu
            260                 265                 270

Gln Ala Leu Arg Gly Val Phe Leu Thr Glu Ala Leu Arg Glu Ala Val
        275                 280                 285

Gly Arg Glu Ala Val Arg Leu Leu Val Ser Val Asp Glu Ala Asp Tyr
    290                 295                 300

Glu Ala Gly Arg Arg Arg Leu Leu Leu Met Glu Glu Glu Gly
305                 310                 315
```

<210> SEQ ID NO 19
<211> LENGTH: 696
<212> TYPE: DNA
<213> ORGANISM: Chlamydia trachomatis
<220> FEATURE:
<221> NAME/KEY: CDS
<222> LOCATION: (1)...(693)

<400> SEQUENCE: 19

| | | | | | | | | | | | | | | | | |
|---|---|---|---|---|---|---|---|---|---|---|---|---|---|---|---|---|
| atg | atg | gag | gtg | ttt | atg | aat | ttt | tta | gat | cag | tta | gat | tta | att | att | 48 |
| Met | Met | Glu | Val | Phe | Met | Asn | Phe | Leu | Asp | Gln | Leu | Asp | Leu | Ile | Ile | |
| 1 | | | | 5 | | | | | 10 | | | | | 15 | | |
| caa | aat | aag | cat | atg | cta | gaa | cac | acg | ttt | tat | gtg | aaa | tgg | tcg | aag | 96 |
| Gln | Asn | Lys | His | Met | Leu | Glu | His | Thr | Phe | Tyr | Val | Lys | Trp | Ser | Lys | |
| | | | | 20 | | | | | 25 | | | | | 30 | | |
| ggg | gag | ctt | act | aaa | gag | caa | tta | cag | gcg | tat | gcc | aaa | gac | tat | tat | 144 |
| Gly | Glu | Leu | Thr | Lys | Glu | Gln | Leu | Gln | Ala | Tyr | Ala | Lys | Asp | Tyr | Tyr | |
| | | | 35 | | | | | 40 | | | | | 45 | | | |
| tta | cat | atc | aaa | gcc | ttt | cct | aaa | tat | tta | tct | gcg | att | cat | agt | cgt | 192 |
| Leu | His | Ile | Lys | Ala | Phe | Pro | Lys | Tyr | Leu | Ser | Ala | Ile | His | Ser | Arg | |
| | 50 | | | | | 55 | | | | | 60 | | | | | |
| tgc | gat | gat | tta | gag | gcg | cgt | aag | tta | ttg | tta | gat | aac | ttg | atg | gat | 240 |
| Cys | Asp | Asp | Leu | Glu | Ala | Arg | Lys | Leu | Leu | Leu | Asp | Asn | Leu | Met | Asp | |
| 65 | | | | | 70 | | | | | 75 | | | | | 80 | |
| gaa | gag | aac | ggt | tac | cct | aat | cat | att | gat | ttg | tgg | aag | cag | ttt | gtg | 288 |
| Glu | Glu | Asn | Gly | Tyr | Pro | Asn | His | Ile | Asp | Leu | Trp | Lys | Gln | Phe | Val | |
| | | | | 85 | | | | | 90 | | | | | 95 | | |
| ttt | gct | cta | gga | gtt | act | cca | gaa | gag | tta | gag | gct | cat | gag | cct | agt | 336 |
| Phe | Ala | Leu | Gly | Val | Thr | Pro | Glu | Glu | Leu | Glu | Ala | His | Glu | Pro | Ser | |
| | | | 100 | | | | | 105 | | | | | 110 | | | |
| gaa | gca | gca | aaa | gcg | aaa | gta | gct | act | ttc | atg | cgg | tgg | tgt | aca | gga | 384 |
| Glu | Ala | Ala | Lys | Ala | Lys | Val | Ala | Thr | Phe | Met | Arg | Trp | Cys | Thr | Gly | |
| | | 115 | | | | | 120 | | | | | 125 | | | | |
| gat | tct | tta | gct | gca | gga | gtg | gct | gct | ttg | tat | tct | tat | gag | agt | caa | 432 |
| Asp | Ser | Leu | Ala | Ala | Gly | Val | Ala | Ala | Leu | Tyr | Ser | Tyr | Glu | Ser | Gln | |
| | 130 | | | | | 135 | | | | | 140 | | | | | |
| att | cca | cgt | atc | gct | aga | gag | aaa | att | cgt | gga | ttg | act | gag | tac | ttt | 480 |
| Ile | Pro | Arg | Ile | Ala | Arg | Glu | Lys | Ile | Arg | Gly | Leu | Thr | Glu | Tyr | Phe | |
| 145 | | | | | 150 | | | | | 155 | | | | | 160 | |
| gga | ttt | tcc | aat | cct | gaa | gac | tat | gca | tat | ttc | aca | gaa | cat | gaa | gaa | 528 |
| Gly | Phe | Ser | Asn | Pro | Glu | Asp | Tyr | Ala | Tyr | Phe | Thr | Glu | His | Glu | Glu | |
| | | | | 165 | | | | | 170 | | | | | 175 | | |
| gcg | gat | gtg | cgg | cat | gct | aga | gaa | gaa | aaa | gcg | ctc | att | gag | atg | ctt | 576 |
| Ala | Asp | Val | Arg | His | Ala | Arg | Glu | Glu | Lys | Ala | Leu | Ile | Glu | Met | Leu | |
| | | | 180 | | | | | 185 | | | | | 190 | | | |
| ctc | aaa | gat | gac | gct | gat | aaa | gtg | tta | gag | gca | tcg | cag | gaa | gta | acg | 624 |
| Leu | Lys | Asp | Asp | Ala | Asp | Lys | Val | Leu | Glu | Ala | Ser | Gln | Glu | Val | Thr | |
| | | 195 | | | | | 200 | | | | | 205 | | | | |
| caa | tct | ttg | tat | ggc | ttt | tta | gat | tct | ttt | ttg | gat | cca | cga | act | tgt | 672 |
| Gln | Ser | Leu | Tyr | Gly | Phe | Leu | Asp | Ser | Phe | Leu | Asp | Pro | Arg | Thr | Cys | |
| | 210 | | | | | 215 | | | | | 220 | | | | | |
| tgt | agt | tgt | cat | caa | tct | tat | taa | | | | | | | | | 696 |
| Cys | Ser | Cys | His | Gln | Ser | Tyr | | | | | | | | | | |
| 225 | | | | 230 | | | | | | | | | | | | |

<210> SEQ ID NO 20
<211> LENGTH: 231
<212> TYPE: PRT
<213> ORGANISM: Chlamydia trachomatis

```
<400> SEQUENCE: 20

Met Met Glu Val Phe Met Asn Phe Leu Asp Gln Leu Asp Leu Ile Ile
 1               5                  10                  15

Gln Asn Lys His Met Leu Glu His Thr Phe Tyr Val Lys Trp Ser Lys
             20                  25                  30

Gly Glu Leu Thr Lys Glu Gln Leu Gln Ala Tyr Ala Lys Asp Tyr Tyr
         35                  40                  45

Leu His Ile Lys Ala Phe Pro Lys Tyr Leu Ser Ala Ile His Ser Arg
     50                  55                  60

Cys Asp Asp Leu Glu Ala Arg Lys Leu Leu Asp Asn Leu Met Asp
 65                  70                  75                  80

Glu Glu Asn Gly Tyr Pro Asn His Ile Asp Leu Trp Lys Gln Phe Val
                 85                  90                  95

Phe Ala Leu Gly Val Thr Pro Glu Glu Leu Glu Ala His Glu Pro Ser
            100                 105                 110

Glu Ala Ala Lys Ala Lys Val Ala Thr Phe Met Arg Trp Cys Thr Gly
            115                 120                 125

Asp Ser Leu Ala Ala Gly Val Ala Ala Leu Tyr Ser Tyr Glu Ser Gln
130                 135                 140

Ile Pro Arg Ile Ala Arg Glu Lys Ile Arg Gly Leu Thr Glu Tyr Phe
145                 150                 155                 160

Gly Phe Ser Asn Pro Glu Asp Tyr Ala Tyr Phe Thr Glu His Glu Glu
                165                 170                 175

Ala Asp Val Arg His Ala Arg Glu Glu Lys Ala Leu Ile Glu Met Leu
            180                 185                 190

Leu Lys Asp Asp Ala Asp Lys Val Leu Glu Ala Ser Gln Glu Val Thr
            195                 200                 205

Gln Ser Leu Tyr Gly Phe Leu Asp Ser Phe Leu Asp Pro Arg Thr Cys
        210                 215                 220

Cys Ser Cys His Gln Ser Tyr
225                 230

<210> SEQ ID NO 21
<211> LENGTH: 687
<212> TYPE: DNA
<213> ORGANISM: Mus musculus
<220> FEATURE:
<221> NAME/KEY: CDS
<222> LOCATION: (1)...(684)

<400> SEQUENCE: 21 atg ctt tat aac gtc agc aaa ggt gtg gtc tat tca gat aca gcc ctg    48
Met Leu Tyr Asn Val Ser Lys Gly Val Val Tyr Ser Asp Thr Ala Leu
 1               5                  10                  15 cag ggg cag gac ggg gac agg gaa gga atg tgg gta gga gct ggg gga    96
Gln Gly Gln Asp Gly Asp Arg Glu Gly Met Trp Val Gly Ala Gly Gly
             20                  25                  30 gcc cta gcc ccc aat acc tcc tcc cta ttt ccc cct gag cct cca ggg   144
Ala Leu Ala Pro Asn Thr Ser Ser Leu Phe Pro Pro Glu Pro Pro Gly
         35                  40                  45 gcc tcg agc aac atc att cct gtc tac tgt gct ctc cta gct aca gtg   192
Ala Ser Ser Asn Ile Ile Pro Val Tyr Cys Ala Leu Leu Ala Thr Val
     50                  55                  60 atc ctt ggt ctg ctg gcc tat gtg gcc ttc aaa tgc tgg cgc tca cat   240
Ile Leu Gly Leu Leu Ala Tyr Val Ala Phe Lys Cys Trp Arg Ser His
 65                  70                  75                  80
```

```
aag caa agg caa cag ttg gct aaa gct cgg act gta gag cta ggg gac        288
Lys Gln Arg Gln Gln Leu Ala Lys Ala Arg Thr Val Glu Leu Gly Asp
                 85                  90                  95 cct gac agg gac cag agg cgt ggt gac agc aac gtc ttc gtg gac tct        336
Pro Asp Arg Asp Gln Arg Arg Gly Asp Ser Asn Val Phe Val Asp Ser
            100                 105                 110 cct cct agt ctg gag ccc tgt att ccc agc cag gga cca cac ccg gac        384
Pro Pro Ser Leu Glu Pro Cys Ile Pro Ser Gln Gly Pro His Pro Asp
        115                 120                 125 ctt ggc tgc cag ctt tac ctg cat att cca cag cag cag gag gaa            432
Leu Gly Cys Gln Leu Tyr Leu His Ile Pro Gln Gln Gln Glu Glu
    130                 135                 140 gtc cag cgg ctc ctg atg atg ggt gag cca gcc aag ggc tgg cag gag        480
Val Gln Arg Leu Leu Met Met Gly Glu Pro Ala Lys Gly Trp Gln Glu
145                 150                 155                 160 ctg gca ggc cac ctc ggc tac caa gct gag gct gtg gaa acc atg gcc        528
Leu Ala Gly His Leu Gly Tyr Gln Ala Glu Ala Val Glu Thr Met Ala
                165                 170                 175 tgt gac caa atg cca gcc tat acc ctg cta agg aac tgg gct gcc caa        576
Cys Asp Gln Met Pro Ala Tyr Thr Leu Leu Arg Asn Trp Ala Ala Gln
            180                 185                 190 gaa ggc aat aga gct acc ctc aga gtg ctg gag gat gct ctg gct gcc        624
Glu Gly Asn Arg Ala Thr Leu Arg Val Leu Glu Asp Ala Leu Ala Ala
        195                 200                 205 ata ggc cga gaa gat gtg gtc cag gtt ttg agc tcg cca gct gag agc        672
Ile Gly Arg Glu Asp Val Val Gln Val Leu Ser Ser Pro Ala Glu Ser
    210                 215                 220 tcc tcg gtg gtg tga                                                    687
Ser Ser Val Val
225

<210> SEQ ID NO 22
<211> LENGTH: 228
<212> TYPE: PRT
<213> ORGANISM: Mus musculus

<400> SEQUENCE: 22

Met Leu Tyr Asn Val Ser Lys Gly Val Val Tyr Ser Asp Thr Ala Leu
  1               5                  10                  15

Gln Gly Gln Asp Gly Asp Arg Glu Gly Met Trp Val Gly Ala Gly Gly
                 20                  25                  30

Ala Leu Ala Pro Asn Thr Ser Ser Leu Phe Pro Pro Glu Pro Pro Gly
            35                  40                  45

Ala Ser Ser Asn Ile Ile Pro Val Tyr Cys Ala Leu Leu Ala Thr Val
        50                  55                  60

Ile Leu Gly Leu Leu Ala Tyr Val Ala Phe Lys Cys Trp Arg Ser His
 65                  70                  75                  80

Lys Gln Arg Gln Gln Leu Ala Lys Ala Arg Thr Val Glu Leu Gly Asp
                 85                  90                  95

Pro Asp Arg Asp Gln Arg Arg Gly Asp Ser Asn Val Phe Val Asp Ser
            100                 105                 110

Pro Pro Ser Leu Glu Pro Cys Ile Pro Ser Gln Gly Pro His Pro Asp
        115                 120                 125

Leu Gly Cys Gln Leu Tyr Leu His Ile Pro Gln Gln Gln Glu Glu
    130                 135                 140

Val Gln Arg Leu Leu Met Met Gly Glu Pro Ala Lys Gly Trp Gln Glu
145                 150                 155                 160
```

```
Leu Ala Gly His Leu Gly Tyr Gln Ala Glu Ala Val Glu Thr Met Ala
            165                 170                 175

Cys Asp Gln Met Pro Ala Tyr Thr Leu Leu Arg Asn Trp Ala Ala Gln
            180                 185                 190

Glu Gly Asn Arg Ala Thr Leu Arg Val Leu Glu Asp Ala Leu Ala Ala
            195                 200                 205

Ile Gly Arg Glu Asp Val Val Gln Val Leu Ser Ser Pro Ala Glu Ser
210                 215                 220

Ser Ser Val Val
225

<210> SEQ ID NO 23
<211> LENGTH: 696
<212> TYPE: DNA
<213> ORGANISM: Chlamydia trachomatis
<220> FEATURE:
<221> NAME/KEY: CDS
<222> LOCATION: (1)...(693)

<400> SEQUENCE: 23
```

| | | | | | | | | | | | | | | | | |
|---|---|---|---|---|---|---|---|---|---|---|---|---|---|---|---|---|
| atg atg gag gtg ttt atg aat ttt tta gat cag tta gat tta att att | | | | | | | | | | | | | | | | 48 |
| Met Met Glu Val Phe Met Asn Phe Leu Asp Gln Leu Asp Leu Ile Ile | | | | | | | | | | | | | | | | |
| 1 | | | | 5 | | | | | 10 | | | | | 15 | | |
| caa aat aag cat atg cta gaa cac aca ttt tat gtg aaa tgg tcg aag | | | | | | | | | | | | | | | | 96 |
| Gln Asn Lys His Met Leu Glu His Thr Phe Tyr Val Lys Trp Ser Lys | | | | | | | | | | | | | | | | |
| | | | 20 | | | | | 25 | | | | | 30 | | | |
| ggg gag ctt act aaa gag caa tta cag gcg tat gcc aaa gac tat tat | | | | | | | | | | | | | | | | 144 |
| Gly Glu Leu Thr Lys Glu Gln Leu Gln Ala Tyr Ala Lys Asp Tyr Tyr | | | | | | | | | | | | | | | | |
| | | 35 | | | | | 40 | | | | | 45 | | | | |
| tta cat atc aaa gcc ttt cct aaa tat tta tct gcg att cat agt cgt | | | | | | | | | | | | | | | | 192 |
| Leu His Ile Lys Ala Phe Pro Lys Tyr Leu Ser Ala Ile His Ser Arg | | | | | | | | | | | | | | | | |
| 50 | | | | | 55 | | | | | 60 | | | | | | |
| tgc gat gat tta gag gcg cgt aag tta ttg tta gat aac ttg atg gat | | | | | | | | | | | | | | | | 240 |
| Cys Asp Asp Leu Glu Ala Arg Lys Leu Leu Leu Asp Asn Leu Met Asp | | | | | | | | | | | | | | | | |
| 65 | | | | | 70 | | | | | 75 | | | | | 80 | |
| gaa gag aac ggt tac cct aat cat att gat ttg tgg aag cag ttt gtg | | | | | | | | | | | | | | | | 288 |
| Glu Glu Asn Gly Tyr Pro Asn His Ile Asp Leu Trp Lys Gln Phe Val | | | | | | | | | | | | | | | | |
| | | | | 85 | | | | | 90 | | | | | 95 | | |
| ttt gct cta gga gtt act cca gaa gag tta gag gct cat gag cct agt | | | | | | | | | | | | | | | | 336 |
| Phe Ala Leu Gly Val Thr Pro Glu Glu Leu Glu Ala His Glu Pro Ser | | | | | | | | | | | | | | | | |
| | | | 100 | | | | | 105 | | | | | 110 | | | |
| gaa gca gca aaa gcg aaa gta gct act ttc atg cgg tgg tgt aca gga | | | | | | | | | | | | | | | | 384 |
| Glu Ala Ala Lys Ala Lys Val Ala Thr Phe Met Arg Trp Cys Thr Gly | | | | | | | | | | | | | | | | |
| | | 115 | | | | | 120 | | | | | 125 | | | | |
| gat tct tta gct gca gga gtg gct gct ttg tat tct tat gag agt caa | | | | | | | | | | | | | | | | 432 |
| Asp Ser Leu Ala Ala Gly Val Ala Ala Leu Tyr Ser Tyr Glu Ser Gln | | | | | | | | | | | | | | | | |
| | 130 | | | | | 135 | | | | | 140 | | | | | |
| att cca cgt atc gct aga gag aaa att cgt gga ttg act gag tac ttt | | | | | | | | | | | | | | | | 480 |
| Ile Pro Arg Ile Ala Arg Glu Lys Ile Arg Gly Leu Thr Glu Tyr Phe | | | | | | | | | | | | | | | | |
| 145 | | | | | 150 | | | | | 155 | | | | | 160 | |
| gga ttt tcc aat cct gaa gac tat gca tat ttc aca gaa cat gaa gaa | | | | | | | | | | | | | | | | 528 |
| Gly Phe Ser Asn Pro Glu Asp Tyr Ala Tyr Phe Thr Glu His Glu Glu | | | | | | | | | | | | | | | | |
| | | | | 165 | | | | | 170 | | | | | 175 | | |
| gcg gat gtg cgg cat gct aga gaa gaa aaa gcg ctc att gag atg ctt | | | | | | | | | | | | | | | | 576 |
| Ala Asp Val Arg His Ala Arg Glu Glu Lys Ala Leu Ile Glu Met Leu | | | | | | | | | | | | | | | | |
| | | | 180 | | | | | 185 | | | | | 190 | | | |
| ctc aaa gat gac gct gat aaa gtg tta gag gca tcg caa gaa gta acg | | | | | | | | | | | | | | | | 624 |
| Leu Lys Asp Asp Ala Asp Lys Val Leu Glu Ala Ser Gln Glu Val Thr | | | | | | | | | | | | | | | | |
| | | 195 | | | | | 200 | | | | | 205 | | | | |

```
caa tct ttg tat ggc ttt tta gat tct ttt ttg gat cca gga act tgt      672
Gln Ser Leu Tyr Gly Phe Leu Asp Ser Phe Leu Asp Pro Gly Thr Cys
    210                 215                 220 tgt agt tgt cat caa tct tat taa                                       696
Cys Ser Cys His Gln Ser Tyr
225                 230
```

<210> SEQ ID NO 24
<211> LENGTH: 231
<212> TYPE: PRT
<213> ORGANISM: Chlamydia trachomatis

<400> SEQUENCE: 24

```
Met Met Glu Val Phe Met Asn Phe Leu Asp Gln Leu Asp Leu Ile Ile
1               5                   10                  15

Gln Asn Lys His Met Leu Glu His Thr Phe Tyr Val Lys Trp Ser Lys
                20                  25                  30

Gly Glu Leu Thr Lys Glu Gln Leu Gln Ala Tyr Ala Lys Asp Tyr Tyr
            35                  40                  45

Leu His Ile Lys Ala Phe Pro Lys Tyr Leu Ser Ala Ile His Ser Arg
    50                  55                  60

Cys Asp Asp Leu Glu Ala Arg Lys Leu Leu Leu Asp Asn Leu Met Asp
65                  70                  75                  80

Glu Glu Asn Gly Tyr Pro Asn His Ile Asp Leu Trp Lys Gln Phe Val
                85                  90                  95

Phe Ala Leu Gly Val Thr Pro Glu Glu Leu Glu Ala His Glu Pro Ser
            100                 105                 110

Glu Ala Ala Lys Ala Lys Val Ala Thr Phe Met Arg Trp Cys Thr Gly
        115                 120                 125

Asp Ser Leu Ala Ala Gly Val Ala Ala Leu Tyr Ser Tyr Glu Ser Gln
    130                 135                 140

Ile Pro Arg Ile Ala Arg Glu Lys Ile Arg Gly Leu Thr Glu Tyr Phe
145                 150                 155                 160

Gly Phe Ser Asn Pro Glu Asp Tyr Ala Tyr Phe Thr Glu His Glu Glu
                165                 170                 175

Ala Asp Val Arg His Ala Arg Glu Glu Lys Ala Leu Ile Glu Met Leu
            180                 185                 190

Leu Lys Asp Asp Ala Asp Lys Val Leu Glu Ala Ser Gln Glu Val Thr
        195                 200                 205

Gln Ser Leu Tyr Gly Phe Leu Asp Ser Phe Leu Asp Pro Gly Thr Cys
    210                 215                 220

Cys Ser Cys His Gln Ser Tyr
225                 230
```

<210> SEQ ID NO 25
<211> LENGTH: 211
<212> TYPE: DNA
<213> ORGANISM: Homo sapien
<220> FEATURE:
<221> NAME/KEY: CDS
<222> LOCATION: (1)...(177)

<400> SEQUENCE: 25

```
atg aac aaa ccc ata aca cca tca aca tat gtg cgc tgc ctc aat gtt       48
Met Asn Lys Pro Ile Thr Pro Ser Thr Tyr Val Arg Cys Leu Asn Val
1               5                   10                  15 gga cta att agg aag ctg tca gat ttt att gat cct caa gaa gga tgg       96
Gly Leu Ile Arg Lys Leu Ser Asp Phe Ile Asp Pro Gln Glu Gly Trp
                20                  25                  30
```

```
aag aag tta gct gta gct att aaa aaa cca tct ggt gat gat aga tac      144
Lys Lys Leu Ala Val Ala Ile Lys Lys Pro Ser Gly Asp Asp Arg Tyr
        35                  40                  45 aat cag ttt cac ata aga tgc tgt tcc caa aac taatacacta ccttctaaag    197
Asn Gln Phe His Ile Arg Cys Cys Ser Gln Asn
 50                  55 aagctataac agtt                                                       211

<210> SEQ ID NO 26
<211> LENGTH: 59
<212> TYPE: PRT
<213> ORGANISM: Homo sapien

<400> SEQUENCE: 26

Met Asn Lys Pro Ile Thr Pro Ser Thr Tyr Val Arg Cys Leu Asn Val
 1               5                  10                  15

Gly Leu Ile Arg Lys Leu Ser Asp Phe Ile Asp Pro Gln Glu Gly Trp
                20                  25                  30

Lys Lys Leu Ala Val Ala Ile Lys Lys Pro Ser Gly Asp Asp Arg Tyr
        35                  40                  45

Asn Gln Phe His Ile Arg Cys Cys Ser Gln Asn
 50                  55

<210> SEQ ID NO 27
<211> LENGTH: 2817
<212> TYPE: DNA
<213> ORGANISM: Homo sapien
<220> FEATURE:
<221> NAME/KEY: CDS
<222> LOCATION: (50)...(1429)

<400> SEQUENCE: 27
gttcttctgt cgccggcttc agcagcccgc gcccgggcag gaatagaag atg aac aaa     58
                                                    Met Asn Lys
                                                     1 ccc ata aca cca tca aca tat gtg cgc tgc ctc aat gtt gga cta att     106
Pro Ile Thr Pro Ser Thr Tyr Val Arg Cys Leu Asn Val Gly Leu Ile
      5                  10                  15 agg aag ctg tca gat ttt att gat cct caa gaa gga tgg aag aag tta    154
Arg Lys Leu Ser Asp Phe Ile Asp Pro Gln Glu Gly Trp Lys Lys Leu
 20                  25                  30                  35 gct gta gct att aaa aaa cca tct ggt gat gat aga tac aat cag ttt    202
Ala Val Ala Ile Lys Lys Pro Ser Gly Asp Asp Arg Tyr Asn Gln Phe
                 40                  45                  50 cac ata agg aga ttt gaa gca tta ctt caa act gga aaa agt ccc act    250
His Ile Arg Arg Phe Glu Ala Leu Leu Gln Thr Gly Lys Ser Pro Thr
         55                  60                  65 tct gaa tta ctg ttt gac tgg ggc acc aca aat tgc aca gtt ggt gat    298
Ser Glu Leu Leu Phe Asp Trp Gly Thr Thr Asn Cys Thr Val Gly Asp
     70                  75                  80 ctt gtg gat ctt ttg atc caa aat gaa ttt ttt gct cct gcg agt ctt    346
Leu Val Asp Leu Leu Ile Gln Asn Glu Phe Phe Ala Pro Ala Ser Leu
 85                  90                  95 ttg ctc cca gat gct gtt ccc aaa act gct aat aca cta cct tct aaa    394
Leu Leu Pro Asp Ala Val Pro Lys Thr Ala Asn Thr Leu Pro Ser Lys
100                 105                 110                 115 gaa gct ata aca gtt cag caa aaa cag atg cct ttc tgt gac aaa gac    442
Glu Ala Ile Thr Val Gln Gln Lys Gln Met Pro Phe Cys Asp Lys Asp
                120                 125                 130
```

-continued

| | |
|---|---|
| agg aca ttg atg aca cct gtg cag aat ctt gaa caa agc tat atg cca<br>Arg Thr Leu Met Thr Pro Val Gln Asn Leu Glu Gln Ser Tyr Met Pro<br>             135                        140                     145 | 490 |
| cct gac tcc tca agt cca gaa aat aaa agt tta gaa gtt agt gat aca<br>Pro Asp Ser Ser Ser Pro Glu Asn Lys Ser Leu Glu Val Ser Asp Thr<br>        150                     155                        160 | 538 |
| cgt ttt cac agt ttt tca ttt tat gaa ttg aag aat gtc aca aat aac<br>Arg Phe His Ser Phe Ser Phe Tyr Glu Leu Lys Asn Val Thr Asn Asn<br>     165                     170                     175 | 586 |
| ttt gat gaa cga ccc att tct gtt ggt ggt aat aaa atg gga gag gga<br>Phe Asp Glu Arg Pro Ile Ser Val Gly Gly Asn Lys Met Gly Glu Gly<br>180                     185                     190                 195 | 634 |
| gga ttt gga gtt gta tat aaa ggc tac gta aat aac aca act gtg gca<br>Gly Phe Gly Val Val Tyr Lys Gly Tyr Val Asn Asn Thr Thr Val Ala<br>                 200                     205                     210 | 682 |
| gtg aag aag ctt gca gca atg gtt gac att act act gaa gaa ctg aaa<br>Val Lys Lys Leu Ala Ala Met Val Asp Ile Thr Thr Glu Glu Leu Lys<br>             215                     220                     225 | 730 |
| cag cag ttt gat caa gaa ata aaa gta atg gca aag tgt caa cat gaa<br>Gln Gln Phe Asp Gln Glu Ile Lys Val Met Ala Lys Cys Gln His Glu<br>           230                     235                     240 | 778 |
| aac tta gta gaa cta ctt ggt ttc tca agt gat gga gat gac ctc tgc<br>Asn Leu Val Glu Leu Leu Gly Phe Ser Ser Asp Gly Asp Asp Leu Cys<br>     245                     250                     255 | 826 |
| tta gta tat gtt tac atg cct aat ggt tca ttg cta gac aga ctc tct<br>Leu Val Tyr Val Tyr Met Pro Asn Gly Ser Leu Leu Asp Arg Leu Ser<br>260                     265                     270                 275 | 874 |
| tgc ttg gat ggt act cca cca ctt tct tgg cac atg aga tgc aag att<br>Cys Leu Asp Gly Thr Pro Pro Leu Ser Trp His Met Arg Cys Lys Ile<br>                 280                     285                     290 | 922 |
| gct cag ggt gca gct aat ggc atc aat ttt cta cat gaa aat cat cat<br>Ala Gln Gly Ala Ala Asn Gly Ile Asn Phe Leu His Glu Asn His His<br>             295                     300                     305 | 970 |
| att cat aga gat att aaa agt gca aat atc tta ctg gat gaa gct ttt<br>Ile His Arg Asp Ile Lys Ser Ala Asn Ile Leu Leu Asp Glu Ala Phe<br>           310                     315                     320 | 1018 |
| act gct aaa ata tct gac ttt ggc ctt gca cgg gct tct gag aag ttt<br>Thr Ala Lys Ile Ser Asp Phe Gly Leu Ala Arg Ala Ser Glu Lys Phe<br>     325                     330                     335 | 1066 |
| gcc cag aca gtc atg act agc aga att gtg gga aca aca gct tat atg<br>Ala Gln Thr Val Met Thr Ser Arg Ile Val Gly Thr Thr Ala Tyr Met<br>340                     345                     350                 355 | 1114 |
| gca cca gaa gct ttg cgt gga gaa ata aca ccc aaa tct gat att tac<br>Ala Pro Glu Ala Leu Arg Gly Glu Ile Thr Pro Lys Ser Asp Ile Tyr<br>                 360                     365                     370 | 1162 |
| agc ttt ggt gtg gtt tta cta gaa ata ata act gga ctt cca gct gtg<br>Ser Phe Gly Val Val Leu Leu Glu Ile Ile Thr Gly Leu Pro Ala Val<br>             375                     380                     385 | 1210 |
| gat gaa cac cgt gaa cct cag tta ttg cta gat att aaa gaa gaa att<br>Asp Glu His Arg Glu Pro Gln Leu Leu Leu Asp Ile Lys Glu Glu Ile<br>           390                     395                     400 | 1258 |
| gaa gat gaa gaa aag aca att gaa gat tat att gat aaa aag atg aat<br>Glu Asp Glu Glu Lys Thr Ile Glu Asp Tyr Ile Asp Lys Lys Met Asn<br>     405                     410                     415 | 1306 |
| gat gct gat tcc act tca gtt gaa gct atg tac tct ggt gct agc caa<br>Asp Ala Asp Ser Thr Ser Val Glu Ala Met Tyr Ser Gly Ala Ser Gln<br>420                     425                     430                 435 | 1354 |
| tgt cgg cat gaa aag aaa aat aag agc cca gac att aag aag gtt cac<br>Cys Arg His Glu Lys Lys Asn Lys Ser Pro Asp Ile Lys Lys Val His<br>                 440                     445                     450 | 1402 |

```
cag ctg ctg caa gag atg aca gct tct taaaacttta ttgaaaaga      1449
Gln Leu Leu Gln Glu Met Thr Ala Ser
        455                 460 ctcttgactt tttatataca cctatctcaa ccatttttt aactgatttt tttcctaaat  1509
attcttcttt acctttaaca aggcataggc tgttgcagga cagtggttat taaagcatgg  1569
gttgaacttc caaatataa aaatagagcc accatatcaa cacttagccc tacccattag   1629
tatcaccccc agttcttaca gtaatccctg agaaatctcc ttcaagcatc accaaacaca  1689
gtttgaaaat tacagggtta gcaaaagag cctgggctgt atgtagggtg gaaacactct   1749
gatctgaagc ccagctgact ccactactaa tttgctgtaa agctttggac atacacttag   1809
ctgctgtgag ccactaataa cattgggcta atatctgctg tgcttctctg acaggtagtc   1869
atgaaaatca aatgatgcaa atatataca agcactttgt aaattgtaaa atgatacaaa    1929
atttaaagtt tatagagcca gttacaaaat cctattagtc atatattat agattgtgtt    1989
cacagcaatc atttaaccac aaataaaata tcccttgatg atactgccat aatgatatgt   2049
ccattattag attatgttac atgacaaagt tgaaggaatt tggcagatgc agttaaggtt   2109
cctaaacaac tcactttgag actgttgaaa gggcctgacc taatccaagt gaacccttg    2169
caagaagaat tctccttgta agccttgaag aagtatgtga gagggccaca ttggctaaaa   2229
cctaaaggtg gcctctagga gatgagacct accttccagt tgtcagcaag caggaaaaaa   2289
aaattgggac ctcagttgca accacaagga actgaattct gccaaaaatc tgagtcagct   2349
tagaagagta ctccaagctt cagatgataa ccacagcctg ggctgacacc tggatttcag   2409
ctttgcatga tcctcagtat gagaatctat ctgttctgtg ctggacttct aatatataga   2469
actgtgagat aatgggtcac attggctgga tgtggtggct catacctgta atcccagca    2529
ctttgggagg ccgaggcagg cagatcacct gaggtcaaga gttcaagacc ggcctggcca   2589
acatggtgaa accccgtctc tactaaaaat acaaaaatta gacgagcgtg gtggtggaca   2649
cctgtagtcc cagctgcttg ggaggctgag gcaggagact agctggaacc agggaggtag   2709
aggttgcagt gagctgagat cgtgccactg cactccagcc tgggtgacag agtgagactc   2769
catcataaat aaataaataa ataaatgggt cccattaagc ctttaaaa               2817
```

<210> SEQ ID NO 28
<211> LENGTH: 460
<212> TYPE: PRT
<213> ORGANISM: Homo sapien

<400> SEQUENCE: 28

```
Met Asn Lys Pro Ile Thr Pro Ser Thr Tyr Val Arg Cys Leu Asn Val
  1               5                  10                  15

Gly Leu Ile Arg Lys Leu Ser Asp Phe Ile Asp Pro Gln Glu Gly Trp
             20                  25                  30

Lys Lys Leu Ala Val Ala Ile Lys Lys Pro Ser Gly Asp Asp Arg Tyr
         35                  40                  45

Asn Gln Phe His Ile Arg Arg Phe Glu Ala Leu Leu Gln Thr Gly Lys
     50                  55                  60

Ser Pro Thr Ser Glu Leu Leu Phe Asp Trp Gly Thr Thr Asn Cys Thr
 65                  70                  75                  80

Val Gly Asp Leu Val Asp Leu Leu Ile Gln Asn Glu Phe Phe Ala Pro
                 85                  90                  95

Ala Ser Leu Leu Leu Pro Asp Ala Val Pro Lys Thr Ala Asn Thr Leu
            100                 105                 110
```

```
Pro Ser Lys Glu Ala Ile Thr Val Gln Gln Lys Gln Met Pro Phe Cys
        115                 120                 125

Asp Lys Asp Arg Thr Leu Met Thr Pro Val Gln Asn Leu Glu Gln Ser
        130                 135                 140

Tyr Met Pro Pro Asp Ser Ser Pro Glu Asn Lys Ser Leu Glu Val
145                 150                 155                 160

Ser Asp Thr Arg Phe His Ser Phe Ser Phe Tyr Glu Leu Lys Asn Val
                165                 170                 175

Thr Asn Asn Phe Asp Glu Arg Pro Ile Ser Val Gly Gly Asn Lys Met
                180                 185                 190

Gly Glu Gly Gly Phe Gly Val Val Tyr Lys Gly Tyr Val Asn Asn Thr
        195                 200                 205

Thr Val Ala Val Lys Lys Leu Ala Ala Met Val Asp Ile Thr Thr Glu
        210                 215                 220

Glu Leu Lys Gln Gln Phe Asp Gln Glu Ile Lys Val Met Ala Lys Cys
225                 230                 235                 240

Gln His Glu Asn Leu Val Glu Leu Leu Gly Phe Ser Ser Asp Gly Asp
                245                 250                 255

Asp Leu Cys Leu Val Tyr Val Tyr Met Pro Asn Gly Ser Leu Leu Asp
                260                 265                 270

Arg Leu Ser Cys Leu Asp Gly Thr Pro Pro Leu Ser Trp His Met Arg
        275                 280                 285

Cys Lys Ile Ala Gln Gly Ala Ala Asn Gly Ile Asn Phe Leu His Glu
        290                 295                 300

Asn His His Ile His Arg Asp Ile Lys Ser Ala Asn Ile Leu Leu Asp
305                 310                 315                 320

Glu Ala Phe Thr Ala Lys Ile Ser Asp Phe Gly Leu Ala Arg Ala Ser
                325                 330                 335

Glu Lys Phe Ala Gln Thr Val Met Thr Ser Arg Ile Val Gly Thr Thr
                340                 345                 350

Ala Tyr Met Ala Pro Glu Ala Leu Arg Gly Glu Ile Thr Pro Lys Ser
        355                 360                 365

Asp Ile Tyr Ser Phe Gly Val Val Leu Leu Glu Ile Ile Thr Gly Leu
        370                 375                 380

Pro Ala Val Asp Glu His Arg Glu Pro Gln Leu Leu Leu Asp Ile Lys
385                 390                 395                 400

Glu Glu Ile Glu Asp Glu Glu Lys Thr Ile Glu Asp Tyr Ile Asp Lys
                405                 410                 415

Lys Met Asn Asp Ala Asp Ser Thr Ser Val Glu Ala Met Tyr Ser Gly
                420                 425                 430

Ala Ser Gln Cys Arg His Glu Lys Lys Asn Lys Ser Pro Asp Ile Lys
        435                 440                 445

Lys Val His Gln Leu Leu Gln Glu Met Thr Ala Ser
        450                 455                 460

<210> SEQ ID NO 29
<211> LENGTH: 142
<212> TYPE: PRT
<213> ORGANISM: Homo sapien

<400> SEQUENCE: 29

Lys Leu Lys Gly Glu Pro Gly Trp Val Thr Ile His Gly Met Ala Gly
1               5                   10                  15

Cys Gly Lys Ser Val Leu Ala Ala Glu Ala Val Arg Asp His Ser Leu
            20                  25                  30
```

-continued

Leu Glu Gly Cys Phe Pro Gly Val His Trp Val Ser Val Gly Lys
        35                  40                  45

Gln Asp Lys Ser Gly Leu Leu Met Lys Leu Gln Asn Leu Cys Thr Arg
    50                  55                  60

Leu Asp Gln Asp Glu Ser Phe Ser Gln Arg Leu Pro Leu Asn Ile Glu
65                  70                  75                  80

Glu Ala Lys Asp Arg Leu Arg Ile Leu Met Leu Arg Lys His Pro Arg
                85                  90                  95

Ser Leu Leu Ile Leu Asp Asp Val Trp Asp Ser Trp Val Leu Lys Ala
            100                 105                 110

Phe Asp Ser Gln Cys Gln Ile Leu Leu Thr Thr Arg Asp Lys Ser Val
        115                 120                 125

Thr Asp Ser Val Met Gly Pro Lys Tyr Val Val Pro Val Glu
    130                 135                 140

<210> SEQ ID NO 30
<211> LENGTH: 145
<212> TYPE: PRT
<213> ORGANISM: C. elegans

<400> SEQUENCE: 30

Glu Met Cys Asp Leu Asp Ser Phe Phe Leu Phe Leu His Gly Arg Ala
1               5                   10                  15

Gly Ser Gly Lys Ser Val Ile Ala Ser Gln Ala Leu Ser Lys Ser Asp
            20                  25                  30

Gln Leu Ile Gly Ile Asn Tyr Asp Ser Ile Val Trp Leu Lys Asp Ser
        35                  40                  45

Gly Thr Ala Pro Lys Ser Thr Phe Asp Leu Phe Thr Asp Ile Leu Leu
    50                  55                  60

Met Leu Lys Ser Glu Asp Asp Leu Leu Asn Phe Pro Ser Val Glu His
65                  70                  75                  80

Val Thr Ser Val Val Leu Lys Arg Met Ile Cys Asn Ala Leu Ile Asp
                85                  90                  95

Arg Pro Asn Thr Leu Phe Val Phe Asp Asp Val Val Gln Glu Glu Thr
            100                 105                 110

Ile Arg Trp Ala Gln Glu Leu Arg Leu Arg Cys Leu Val Thr Thr Arg
        115                 120                 125

Asp Val Glu Ile Ser Asn Ala Ala Ser Gln Thr Cys Glu Phe Ile Glu
    130                 135                 140

Val
145

<210> SEQ ID NO 31
<211> LENGTH: 75
<212> TYPE: PRT
<213> ORGANISM: Homo sapien

<400> SEQUENCE: 31

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

```
Gln Glu Lys Arg Met Leu Glu Ser Asn Leu Ser Phe Leu Lys Glu
        50                  55                  60

Leu Leu Phe Arg Ile Asn Arg Leu Asp Leu Leu
 65                  70                  75

<210> SEQ ID NO 32
<211> LENGTH: 76
<212> TYPE: PRT
<213> ORGANISM: Homo sapien

<400> SEQUENCE: 32

His Leu Leu Ile Arg Val Met Leu Tyr Gln Ile Ser Glu Glu Val Ser
 1               5                  10                  15

Arg Ser Glu Leu Arg Ser Phe Lys Phe Leu Gln Glu Glu Ile Ser
                20                  25                  30

Lys Cys Lys Leu Asp Asp Asp Met Asn Leu Leu Asp Ile Phe Ile Glu
            35                  40                  45

Met Glu Lys Arg Val Ile Leu Gly Glu Gly Lys Leu Asp Ile Leu Lys
        50                  55                  60

Arg Val Cys Ala Gln Ile Asn Lys Ser Leu Leu Lys
 65                  70                  75

<210> SEQ ID NO 33
<211> LENGTH: 77
<212> TYPE: PRT
<213> ORGANISM: Homo sapien

<400> SEQUENCE: 33

Lys Val Ser Phe Arg Glu Lys Leu Leu Ile Ile Asp Ser Asn Leu Gly
 1               5                  10                  15

Val Gln Asp Val Glu Asn Leu Lys Phe Leu Cys Ile Gly Leu Val Pro
                20                  25                  30

Asn Lys Lys Leu Glu Lys Ser Ser Ala Ser Asp Val Phe Glu His
            35                  40                  45

Leu Leu Ala Glu Asp Leu Leu Ser Glu Glu Asp Pro Phe Phe Leu Ala
        50                  55                  60

Glu Leu Leu Tyr Ile Ile Arg Gln Lys Lys Leu Leu Gln
 65                  70                  75

<210> SEQ ID NO 34
<211> LENGTH: 72
<212> TYPE: PRT
<213> ORGANISM: Homo sapien

<400> SEQUENCE: 34

Val Ser Leu Phe Arg Asn Leu Leu Tyr Glu Leu Ser Glu Gly Ile Asp
 1               5                  10                  15

Ser Glu Asn Leu Lys Asp Met Ile Phe Leu Leu Lys Asp Ser Leu Pro
                20                  25                  30

Lys Thr Glu Met Thr Ser Leu Ser Phe Leu Ala Phe Leu Glu Lys Gln
            35                  40                  45

Gly Lys Ile Asp Glu Asp Asn Leu Thr Cys Leu Glu Asp Leu Cys Lys
        50                  55                  60

Thr Val Val Pro Lys Leu Leu Arg
 65                  70
```

```
-continued

<210> SEQ ID NO 35
<211> LENGTH: 77
<212> TYPE: PRT
<213> ORGANISM: Homo sapien

<400> SEQUENCE: 35

Met Asp Pro Phe Leu Val Leu Leu His Ser Val Ser Ser Leu Ser
1               5                   10                  15

Ser Ser Glu Leu Thr Glu Leu Lys Phe Leu Cys Leu Gly Arg Val Gly
            20                  25                  30

Lys Arg Lys Leu Glu Arg Val Gln Ser Gly Leu Asp Leu Phe Ser Met
        35                  40                  45

Leu Leu Glu Gln Asn Asp Leu Glu Pro Gly His Thr Glu Leu Leu Arg
50                  55                  60

Glu Leu Leu Ala Ser Leu Arg Arg His Asp Leu Leu Arg
65                  70                  75

<210> SEQ ID NO 36
<211> LENGTH: 99
<212> TYPE: PRT
<213> ORGANISM: Homo sapien

<400> SEQUENCE: 36

Trp Pro Glu Glu His Gly Glu Gln Glu His Gly Leu Tyr Ser Leu His
1               5                   10                  15

Arg Met Phe Asp Ile Val Gly Thr His Leu Thr His Arg Asp Val Arg
            20                  25                  30

Val Leu Ser Phe Leu Phe Val Asp Val Ile Asp His Glu Arg Gly Leu
        35                  40                  45

Ile Arg Asn Gly Arg Asp Phe Leu Leu Ala Leu Glu Arg Gln Gly Arg
    50                  55                  60

Cys Asp Glu Ser Asn Phe Arg Gln Val Leu Gln Leu Leu Arg Ile Ile
65                  70                  75                  80

Thr Arg His Asp Leu Leu Pro Tyr Val Thr Leu Lys Arg Arg Arg Ala
                85                  90                  95

Val Cys Pro

<210> SEQ ID NO 37
<211> LENGTH: 99
<212> TYPE: PRT
<213> ORGANISM: Mus musculus

<400> SEQUENCE: 37

Trp Pro Glu Glu Arg Gly Glu Gln Glu His Gly Leu Tyr Ser Leu His
1               5                   10                  15

Arg Met Phe Asp Ile Val Gly Thr His Leu Thr His Arg Asp Val Arg
            20                  25                  30

Val Leu Ser Phe Leu Phe Val Asp Val Ile Asp His Glu Arg Gly Leu
        35                  40                  45

Ile Arg Asn Gly Arg Asp Phe Leu Leu Ala Leu Glu Arg Gln Gly Arg
    50                  55                  60

Cys Asp Glu Ser Asn Phe Arg Gln Val Leu Gln Leu Leu Arg Ile Ile
65                  70                  75                  80

Thr Arg His Asp Leu Leu Pro Tyr Val Thr Leu Lys Lys Arg Arg Ala
                85                  90                  95

Val Cys Pro
```

```
<210> SEQ ID NO 38
<211> LENGTH: 146
<212> TYPE: PRT
<213> ORGANISM: Danio rerio

<400> SEQUENCE: 38

Trp Glu Thr Glu Cys Leu Ser Tyr Tyr Glu Thr Leu Ser Leu His
 1               5                  10                  15

Glu Ile Phe Glu Ile Val Gly Ser Gln Leu Thr Glu Thr Cys Gly Gly
            20                  25                  30

Glu Val Ala Phe Leu Leu Asp Glu Thr Tyr Pro Gly Lys His Pro Leu
        35                  40                  45

Asp Pro Glu Gly Trp Thr Glu Asp Leu Pro Pro Gly Pro Asp Gly Ser
    50                  55                  60

Pro Gln Ala Asn Thr Pro Cys Pro Arg Leu Leu Lys Ser Trp Gln Arg
65                  70                  75                  80

Met Gln Pro Gln Lys Glu Gly Cys Ser Ile Ala Ser Arg His Arg Pro
                85                  90                  95

Lys Ser Gly Val Glu Leu Leu Glu Leu Glu Arg Arg Gly Tyr Leu
            100                 105                 110

Ser Asp Ala Asn Leu Arg Pro Leu Gln Leu Leu Arg Ile Leu Thr
        115                 120                 125

Arg His Asp Val Leu Pro Phe Val Ser Gln Lys Lys Arg Arg Thr Val
    130                 135                 140

Ser Pro
145

<210> SEQ ID NO 39
<211> LENGTH: 82
<212> TYPE: PRT
<213> ORGANISM: Homo sapien

<400> SEQUENCE: 39

Met Asp Pro Phe Leu Val Leu Leu His Ser Val Ser Ser Ser Leu Ser
 1               5                  10                  15

Ser Ser Glu Leu Thr Glu Leu Lys Tyr Leu Cys Leu Gly Arg Lys Arg
            20                  25                  30

Lys Leu Glu Arg Val Gln Ser Gly Leu Asp Leu Phe Ser Met Leu Leu
        35                  40                  45

Glu Gln Asn Asp Leu Glu Pro Gly His Thr Glu Leu Leu Arg Glu Leu
    50                  55                  60

Leu Ala Ser Leu Arg Arg His Asp Leu Leu Arg Arg Val Asp Asp Phe
65                  70                  75                  80

Glu Leu

<210> SEQ ID NO 40
<211> LENGTH: 18
<212> TYPE: DNA
<213> ORGANISM: Artificial Sequence
<220> FEATURE:
<223> OTHER INFORMATION: oligonucleotide

<400> SEQUENCE: 40
atgatgctga aaggaata                                          18
```

<210> SEQ ID NO 41
<211> LENGTH: 40
<212> TYPE: DNA
<213> ORGANISM: Artificial Sequence
<220> FEATURE:
<223> OTHER INFORMATION: oligonucleotide

<400> SEQUENCE: 41
agtcctcgac tcacgtgcaa ggatgatgct gaaaggaata          40

<210> SEQ ID NO 42
<211> LENGTH: 35
<212> TYPE: DNA
<213> ORGANISM: Artificial Sequence
<220> FEATURE:
<223> OTHER INFORMATION: synthetic primer

<400> SEQUENCE: 42
gcgaattcat gaacaaaccc ataacaccat caaca              35

<210> SEQ ID NO 43
<211> LENGTH: 35
<212> TYPE: DNA
<213> ORGANISM: Artificial Sequence
<220> FEATURE:
<223> OTHER INFORMATION: synthetic primer

<400> SEQUENCE: 43
gcctcgagtt aagaagctgt catctcttgc agcag              35

<210> SEQ ID NO 44
<211> LENGTH: 18
<212> TYPE: DNA
<213> ORGANISM: Artificial Sequence
<220> FEATURE:
<223> OTHER INFORMATION: synthetic primer

<400> SEQUENCE: 44
atgatggagg tgtttatg                                 18

<210> SEQ ID NO 45
<211> LENGTH: 20
<212> TYPE: DNA
<213> ORGANISM: Artificial Sequence
<220> FEATURE:
<223> OTHER INFORMATION: synthetic primer

<400> SEQUENCE: 45
ataagattga tgacaactac                               20

<210> SEQ ID NO 46
<211> LENGTH: 16
<212> TYPE: DNA
<213> ORGANISM: Artificial Sequence
<220> FEATURE:
<223> OTHER INFORMATION: synthetic primer

<400> SEQUENCE: 46
ctccgccgcc gtctgg                                   16

<210> SEQ ID NO 47
<211> LENGTH: 21
<212> TYPE: DNA
<213> ORGANISM: Artificial Sequence
<220> FEATURE:
<223> OTHER INFORMATION: synthetic primer -continued

```
<400> SEQUENCE: 47
cgcccaggag tcatcggacg c                                              21

<210> SEQ ID NO 48
<211> LENGTH: 23
<212> TYPE: DNA
<213> ORGANISM: Artificial Sequence
<220> FEATURE:
<223> OTHER INFORMATION: synthetic primer

<400> SEQUENCE: 48
ccgaggtggc ctgccagctc ctg                                            23

<210> SEQ ID NO 49
<211> LENGTH: 28
<212> TYPE: DNA
<213> ORGANISM: Artificial Sequence
<220> FEATURE:
<223> OTHER INFORMATION: synthetic primer

<400> SEQUENCE: 49
acacccggac cttgcctgcc agctttac                                       28

<210> SEQ ID NO 50
<211> LENGTH: 18
<212> TYPE: DNA
<213> ORGANISM: Artificial Sequence
<220> FEATURE:
<223> OTHER INFORMATION: synthetic primer

<400> SEQUENCE: 50
atgctttata acgtcagc                                                  18

<210> SEQ ID NO 51
<211> LENGTH: 21
<212> TYPE: DNA
<213> ORGANISM: Artificial Sequence
<220> FEATURE:
<223> OTHER INFORMATION: synthetic primer

<400> SEQUENCE: 51
tcacaccacc gaggagctct c                                              21

<210> SEQ ID NO 52
<211> LENGTH: 195
<212> TYPE: DNA
<213> ORGANISM: C. muridarum
<220> FEATURE:
<221> NAME/KEY: CDS
<222> LOCATION: (1)...(195)

<400> SEQUENCE: 52 gat tta tgg aaa caa ttt gtg ttt gct ctt gga gtg tct tca gaa gag      48
Asp Leu Trp Lys Gln Phe Val Phe Ala Leu Gly Val Ser Ser Glu Glu
 1               5                  10                  15 cta gaa gct cat gaa ccc agt gaa gca gct aaa gct aag gtt gcg aca      96
Leu Glu Ala His Glu Pro Ser Glu Ala Ala Lys Ala Lys Val Ala Thr
             20                  25                  30 ttt atg cgg tgg tgc aca ggg gat tct tta gca gca gga gta gcg gct     144
Phe Met Arg Trp Cys Thr Gly Asp Ser Leu Ala Ala Gly Val Ala Ala
         35                  40                  45
```

```
ttg tat tct tat gaa agt caa att cct tgc gta gct aaa gaa aaa att     192
Leu Tyr Ser Tyr Glu Ser Gln Ile Pro Cys Val Ala Lys Glu Lys Ile
         50                  55                  60 cgt                                                                 195
Arg
 65

<210> SEQ ID NO 53
<211> LENGTH: 65
<212> TYPE: PRT
<213> ORGANISM: C. muridarum

<400> SEQUENCE: 53

Asp Leu Trp Lys Gln Phe Val Phe Ala Leu Gly Val Ser Ser Glu Glu
  1               5                  10                  15

Leu Glu Ala His Glu Pro Ser Glu Ala Ala Lys Ala Lys Val Ala Thr
             20                  25                  30

Phe Met Arg Trp Cys Thr Gly Asp Ser Leu Ala Ala Gly Val Ala Ala
         35                  40                  45

Leu Tyr Ser Tyr Glu Ser Gln Ile Pro Cys Val Ala Lys Glu Lys Ile
     50                  55                  60

Arg
 65

<210> SEQ ID NO 54
<211> LENGTH: 711
<212> TYPE: DNA
<213> ORGANISM: C. muridarum
<220> FEATURE:
<221> NAME/KEY: CDS
<222> LOCATION: (1)...(708)

<400> SEQUENCE: 54 atg gaa tca aga aaa gga ata aaa gag gtg agc atg aat ttt tta gat     48
Met Glu Ser Arg Lys Gly Ile Lys Glu Val Ser Met Asn Phe Leu Asp
  1               5                  10                  15 cag cta gat gca att att caa aac aaa cat atg tta gaa cac cct ttt    96
Gln Leu Asp Ala Ile Ile Gln Asn Lys His Met Leu Glu His Pro Phe
             20                  25                  30 tac atg aag tgg tca aaa gga gag ctg aca aaa gaa caa tta cag gca    144
Tyr Met Lys Trp Ser Lys Gly Glu Leu Thr Lys Glu Gln Leu Gln Ala
         35                  40                  45 tac gca aaa gat tac tat ttg cat atc aaa gct ttt cca aaa tat tta    192
Tyr Ala Lys Asp Tyr Tyr Leu His Ile Lys Ala Phe Pro Lys Tyr Leu
     50                  55                  60 tct gct att cat agc cgt tgt gat gat tta gaa gcc gcc aag tta tta   240
Ser Ala Ile His Ser Arg Cys Asp Asp Leu Glu Ala Arg Lys Leu Leu
 65                  70                  75                  80 tta gat aac tta atg gat gaa gag aat ggt tat cct aat cat att gat   288
Leu Asp Asn Leu Met Asp Glu Glu Asn Gly Tyr Pro Asn His Ile Asp
                 85                  90                  95 tta tgg aaa caa ttt gtg ttt gct ctt gga gtg tct tca gaa gag cta   336
Leu Trp Lys Gln Phe Val Phe Ala Leu Gly Val Ser Ser Glu Glu Leu
            100                 105                 110 gaa gct cat gaa ccc agt gaa gca gct aaa gct aag gtt gcg aca ttt   384
Glu Ala His Glu Pro Ser Glu Ala Ala Lys Ala Lys Val Ala Thr Phe
        115                 120                 125 atg cgg tgg tgc aca ggg gat tct tta gca gca gga gta gcg gct ttg   432
Met Arg Trp Cys Thr Gly Asp Ser Leu Ala Ala Gly Val Ala Ala Leu
    130                 135                 140
```

```
tat tct tat gaa agt caa att cct tgc gta gct aaa gaa aaa att cgt    480
Tyr Ser Tyr Glu Ser Gln Ile Pro Cys Val Ala Lys Glu Lys Ile Arg
145                 150                 155                 160 gga ttg att gag tac ttt ggc ttt tct aat cct gaa gat tat gct tat    528
Gly Leu Ile Glu Tyr Phe Gly Phe Ser Asn Pro Glu Asp Tyr Ala Tyr
                165                 170                 175 ttc acg gag cat gaa gaa gct gat gtg cgt cat gct agg gaa gaa aag    576
Phe Thr Glu His Glu Glu Ala Asp Val Arg His Ala Arg Glu Glu Lys
            180                 185                 190 gcc tta att gag atg ttg tct aga gat gat agc gac aaa gtt tta gaa    624
Ala Leu Ile Glu Met Leu Ser Arg Asp Asp Ser Asp Lys Val Leu Glu
        195                 200                 205 gct tcg cga gaa gtt aca caa tct tta tac ggc ttt ttg gat tca ttt    672
Ala Ser Arg Glu Val Thr Gln Ser Leu Tyr Gly Phe Leu Asp Ser Phe
    210                 215                 220 tta gag cct gca aca tgt tgt cat tgt cac aaa gct taa                711
Leu Glu Pro Ala Thr Cys Cys His Cys His Lys Ala
225                 230                 235
```

<210> SEQ ID NO 55
<211> LENGTH: 236
<212> TYPE: PRT
<213> ORGANISM: C. muridarum

<400> SEQUENCE: 55

```
Met Glu Ser Arg Lys Gly Ile Lys Glu Val Ser Met Asn Phe Leu Asp
1               5                   10                  15

Gln Leu Asp Ala Ile Ile Gln Asn Lys His Met Leu Glu His Pro Phe
            20                  25                  30

Tyr Met Lys Trp Ser Lys Gly Glu Leu Thr Lys Glu Gln Leu Gln Ala
        35                  40                  45

Tyr Ala Lys Asp Tyr Tyr Leu His Ile Lys Ala Phe Pro Lys Tyr Leu
    50                  55                  60

Ser Ala Ile His Ser Arg Cys Asp Asp Leu Glu Ala Arg Lys Leu Leu
65                  70                  75                  80

Leu Asp Asn Leu Met Asp Glu Glu Asn Gly Tyr Pro Asn His Ile Asp
                85                  90                  95

Leu Trp Lys Gln Phe Val Phe Ala Leu Gly Val Ser Ser Glu Glu Leu
            100                 105                 110

Glu Ala His Glu Pro Ser Glu Ala Ala Lys Ala Lys Val Ala Thr Phe
        115                 120                 125

Met Arg Trp Cys Thr Gly Asp Ser Leu Ala Ala Gly Val Ala Ala Leu
    130                 135                 140

Tyr Ser Tyr Glu Ser Gln Ile Pro Cys Val Ala Lys Glu Lys Ile Arg
145                 150                 155                 160

Gly Leu Ile Glu Tyr Phe Gly Phe Ser Asn Pro Glu Asp Tyr Ala Tyr
                165                 170                 175

Phe Thr Glu His Glu Glu Ala Asp Val Arg His Ala Arg Glu Glu Lys
            180                 185                 190

Ala Leu Ile Glu Met Leu Ser Arg Asp Asp Ser Asp Lys Val Leu Glu
        195                 200                 205

Ala Ser Arg Glu Val Thr Gln Ser Leu Tyr Gly Phe Leu Asp Ser Phe
    210                 215                 220

Leu Glu Pro Ala Thr Cys Cys His Cys His Lys Ala
225                 230                 235
```

<210> SEQ ID NO 56
<211> LENGTH: 65
<212> TYPE: PRT
<213> ORGANISM: C. pneumoniae

<400> SEQUENCE: 56

Asp Leu Trp Arg Gln Phe Ala Leu Ser Leu Gly Val Ser Glu Glu Glu
1               5                   10                  15

Leu Ala Asn His Glu Phe Ser Gln Ala Ala Gln Asp Met Val Ala Thr
            20                  25                  30

Phe Arg Arg Leu Cys Asp Met Pro Gln Leu Ala Val Gly Leu Gly Ala
        35                  40                  45

Leu Tyr Thr Tyr Glu Ile Gln Ile Pro Gln Val Cys Val Glu Lys Ile
    50                  55                  60

Arg
65

<210> SEQ ID NO 57
<211> LENGTH: 224
<212> TYPE: PRT
<213> ORGANISM: C. pneumoniae

<400> SEQUENCE: 57

Met Thr Ser Trp Ile Glu Leu Leu Asp Lys Gln Ile Glu Asp Gln His
1               5                   10                  15

Met Leu Lys His Glu Phe Tyr Gln Arg Trp Ser Glu Gly Lys Leu Glu
            20                  25                  30

Lys Gln Gln Leu Gln Ala Tyr Ala Lys Asp Tyr Tyr Leu His Ile Lys
        35                  40                  45

Ala Phe Pro Cys Tyr Leu Ser Ala Leu His Ala Arg Cys Asp Asp Leu
    50                  55                  60

Gln Ile Arg Arg Gln Ile Leu Glu Asn Leu Met Asp Glu Glu Ala Gly
65                  70                  75                  80

Asn Pro Asn His Ile Asp Leu Trp Arg Gln Phe Ala Leu Ser Leu Gly
                85                  90                  95

Val Ser Glu Glu Glu Leu Ala Asn His Glu Phe Ser Gln Ala Ala Gln
                100                 105                 110

Asp Met Val Ala Thr Phe Arg Arg Leu Cys Asp Met Pro Gln Leu Ala
            115                 120                 125

Val Gly Leu Gly Ala Leu Tyr Thr Tyr Glu Ile Gln Ile Pro Gln Val
        130                 135                 140

Cys Val Glu Lys Ile Arg Gly Leu Lys Glu Tyr Phe Gly Val Ser Ala
145                 150                 155                 160

Arg Gly Tyr Ala Tyr Phe Thr Val His Gln Glu Ala Asp Ile Lys His
                165                 170                 175

Ala Ser Glu Glu Lys Glu Met Leu Gln Thr Leu Val Gly Arg Glu Asn
            180                 185                 190

Pro Asp Ala Val Leu Gln Gly Ser Gln Glu Val Leu Asp Thr Leu Trp
        195                 200                 205

Asn Phe Leu Ser Ser Phe Ile Asn Ser Thr Glu Pro Cys Ser Cys Lys
    210                 215                 220

<210> SEQ ID NO 58
<211> LENGTH: 65
<212> TYPE: PRT
<213> ORGANISM: C. psittaci

```
-continued

<400> SEQUENCE: 58

Asp Leu Trp Lys Asn Phe Ala Tyr Ala Leu Gly Val Thr Glu Glu Glu
 1               5                  10                  15

Leu Glu Asn His Val Pro Ser Ala Ala Ala Gln Lys Lys Val Asp Thr
            20                  25                  30

Phe Leu Arg Trp Cys Thr Gly Asp Ser Leu Ser Ala Gly Val Ala Ala
        35                  40                  45

Leu Tyr Thr Tyr Glu Ser Gln Ile Pro Thr Val Ala Glu Thr Lys Ile
    50                  55                  60

Ser
65

<210> SEQ ID NO 59
<211> LENGTH: 18
<212> TYPE: DNA
<213> ORGANISM: Artificial Sequence
<220> FEATURE:
<223> OTHER INFORMATION: primer

<400> SEQUENCE: 59
gcagtcattc gcgttgga                                                      18

<210> SEQ ID NO 60
<211> LENGTH: 21
<212> TYPE: DNA
<213> ORGANISM: Artificial Sequence
<220> FEATURE:
<223> OTHER INFORMATION: primer

<400> SEQUENCE: 60
cgcagaacgg gacataactt g                                                  21

<210> SEQ ID NO 61
<211> LENGTH: 22
<212> TYPE: DNA
<213> ORGANISM: Artificial Sequence
<220> FEATURE:
<223> OTHER INFORMATION: primer

<400> SEQUENCE: 61
tgatatcgcc gcgctcgtcg tc                                                 22

<210> SEQ ID NO 62
<211> LENGTH: 22
<212> TYPE: DNA
<213> ORGANISM: Artificial Sequence
<220> FEATURE:
<223> OTHER INFORMATION: primer

<400> SEQUENCE: 62
ggatggcatg ggggagggca ta                                                 22
```

DEATH DOMAIN PROTEINS

This application claims benefit of U.S. Provisional Application No. 60/367,360, filed Nov. 17, 2000, which was converted from U.S. Ser.No. 09/715,893, and of U.S. Provisional Application No. 60/301,889, filed Jun. 29, 2001, both of which are incorporated herein by reference.

This invention was made with government support under grant numbers AG15393 and CA68390 awarded by the National Institutes of Health. The United States Government has certain rights in this invention.

BACKGROUND OF THE INVENTION

This invention relates generally to the fields of molecular biology and molecular medicine and more specifically to proteins involved in the regulation of immunological response and cell death.

Programmed cell death is a physiologic process that ensures homeostasis is maintained between cell production and cell turnover in essentially all self-renewing tissues. In many cases, characteristic morphological changes, termed "apoptosis," occur in a dying cell. Since similar changes occur in different types of dying cells, cell death appears to proceed through a common pathway in different cell types.

In addition to maintaining tissue homeostasis, apoptosis also occurs in response to a variety of external stimuli, including growth factor deprivation, alterations in calcium levels, free-radicals, cytotoxic lymphokines, infection by some viruses and bacteria, radiation and most chemotherapeutic agents. Thus, apoptosis is an inducible event that likely is subject to similar mechanisms of regulation as occur, for example, in a metabolic pathway. In this regard, dysregulation of apoptosis also can occur and is observed, for example, in some types of cancer cells, which survive for a longer time than corresponding normal cells, and in neurodegenerative diseases where neurons die prematurely. In viral and certain bacterial infections, induction of apoptosis can figure prominently in the pathophysiology of the disease process, because immune-based eradication of viral or bacterial infections depend on elimination of virus or bacteria-producing host cells by immune cell attack resulting in apoptosis.

It has long been recognized that viruses harbor genes that regulate apoptosis of host cells, making vital contributions to the virus life-cycle. Some types of bacteria, such as *Chlamiydiae* species, have also been found to regulate apoptosis in host cells. Previous studies have established that infection of mammalian cells with *Chlamydiae* species can either suppress or induce apoptosis, depending on whether examined early or late in the infection cycle of these obligate intracellular bacteria. However, the bacterial genes responsible for the regulation of host cell apoptosis are not known.

Tumor Necrosis Factor (TNF) family cytokines play an important role in a wide variety of immunological, allergic, and inflammatory responses. Several members of the TNF family have been identified, including TNFα, Lymphotoxin-α, Lymphotoxin-β, LIGHT, CD27 Ligand (CD27L), CD30L, CD40L, Fas-L, Trail, and others. These molecules are generally produced as Type-II integral membrane proteins on the surface of cells, undergoing subsequent release into the excellular milieu as a result of proteolytic cleavage. Many of the TNF-family cytokines however remain anchored in the plasma membrane, relying on interactions with receptor-bearing cells through cell-cell contact. The receptors for TNF-family cytokines are equally diverse. All members of the family have a conserved arrangement of cysteines in their extracellular domains, which is one of the criteria for membership in this family.

The intracellular cytosolic domain of TNF-family receptors are diverse in their amino acid sequences, but can be broadly classified into two types: (a) those that contain a protein-interaction module known as a Death-Domain (TNFR1, Fas, DR3, DR4, DR5, DR6, p75NTR) and those that do not (TNFR2, CD27, CD30, CD40, LTβR, 4B1 and others). Death Domains are responsible for interactions of a subgroup of the TNF-Receptor (TNFR) family with adapter proteins which bind in turn to caspase-family intracellular proteases involved in inducing apoptosis (programmed cell death). However, the Death Domains can also mediate binding to other types of adaptor molecules which bind kinases or other types of signaling molecules rather than proteases. For example, several death domain proteins participate in regulation of NFκB induction during an inflammatory response.

Although some of the proteins involved in programmed cell death have been identified and associations among some of these proteins have been described, additional apoptosis regulating proteins remain to be found. Furthermore, the mechanisms by which these proteins mediate their activity remains to be elucidated. The identification of the proteins involved in cell death and an understanding of the associations between these proteins can provide a means for manipulating the process of apoptosis in a cell and, therefore, selectively regulating the relative lifespan of a cell or its relative resistance to cell death stimuli.

The identification of new proteins or new domains within known proteins, and the elucidation of the proteins with which they interact, can form the basis for strategies designed to alter apoptosis, cytokine production, cytokine receptor signaling, and other cellular processes. Such new proteins can thus be used to develop therapeutic applications for controlling apoptosis.

Thus, a need exists to identify novel apoptosis-related domains within both novel and known proteins. The present invention satisfies this need and provides additional advantages as well.

SUMMARY OF THE INVENTION

In accordance with the present invention, there are provided novel death domain (DD) and death effector domain (DED) polypeptides. The invention also provides nucleic acid molecules encoding DDs and DEDs, vectors containing these nucleic acid molecules and host cells containing the vectors. The invention also provides antibodies that can specifically bind to invention DDs and DEDs. Such DDs and DEDs and/or anti-DD or DED antibodies are useful for discovery of drugs that suppress infection, autoimmunity, inflammation, allergy, allograft rejection, sepsis, and other diseases, and can be used in the treatment of inflammatory diseases.

The present invention provides a death domain-containing protein, CTDD, from *Chlamydia trachomatis* that can induce apoptosis. In addition, corresponding death domains from other *Chlamydia* species are provided. The invention also provides nucleic acid molecules encoding these polypeptides, vectors containing these nucleic acid molecules, host cells containing the vectors, and antibodies that can specifically bind to these polypeptides.

The present invention also provides a screening assay useful for identifying agents that can effectively alter the association of an invention DD or DED with itself or with other proteins. By altering the self-association of DDs or DEDs or by altering their interactions with other proteins, an effective agent can increase or decrease the activation of kinases, or modulate cellular pathways that effect apoptosis, cell proliferation, cell adhesion, cell stress responses, responses to microbial infection, B cell immunoglobulin class switching, and the like.

The invention also provides methods of altering the activity of a DD or DED in a cell, wherein such increased or decreased activity of a DD or DED can modulate the level of kinase activity or cellular pathways that effect apoptosis, cell proliferation, cell adhesion, cell stress responses, responses to microbial infection, B cell immunoglobulin class switching, and the like. For example, the activity of DD or DED in a cell can be increased by introducing into the cell and expressing a nucleic acid sequence encoding this polypeptide or proteins comprising such DD or DED. In addition, the activity of DD or DED, or DD/DED-comprising proteins in a cell can be decreased by introducing into the cell and expressing an antisense nucleotide sequence that is complementary to a portion of a nucleic acid molecule encoding the DD/DED or DD/DED-comprising proteins.

The invention also provides methods for using an agent that can specifically bind DD or DED or a nucleotide sequence that can bind to a nucleic acid molecule encoding DD or DED to diagnose a pathology that is characterized by an altered level of apoptosis, cell proliferation, cell adhesion, cell stress responses, responses to microbial infection, and B cell immunoglobulin class switching due to an increased or decreased level of DD or DED in a cell.

BRIEF DESCRIPTION OF THE FIGURES

FIG. 1 shows that DAP3, a DED-containing protein, associates with FADD and regulates FADD-induced apoptosis. binding activity, association with FADD, and regulation of FADD-induced apoptosis was tested (FIG. 1). FIG. 1B shows Fas-inducible association of DAP3 with FADD in transfected HEK293T cells. FIG. 1D shows mapping of FADD-binding region in DAP3 using transfected 293T cells.

FIG. 2 shows DAP3 binding to the prodomain of pro-Caspase8 and regulation of caspase-8 activation.

FIG. 3 shows that DAP3 directly binds the cytosolic domain of DR4 and modulates Trail Receptor-induced apoptosis.

FIG. 4 shows sequence analysis of DAP3. FIG. 4B shows an alignment of the amino acid sequence of NB-ARC domains of human Apaf-1 (SEQ ID NO:29) and *C. elegans* CED4 (SEQ ID NO:30) with residues 115–213 of DAP3 (SEQ ID NO:4). Asterisks indicate nucleotide-binding motifs. FIG. 4C shows a sequence alignment of DEDs of pro-Caspase 8 (SEQ ID NOS:31 and 32 for DED1 and DED2, respectively), pro-caspase 10 (SEQ ID NOS:33 and 34 for DED1 and DED2, respectively), and FADD (SEQ ID NO:35) with residues 268–337 of DAP3 (SEQ ID NO:2). Identical and similar residues are indicated in black and gray blocks, respectively.

Figure 9:
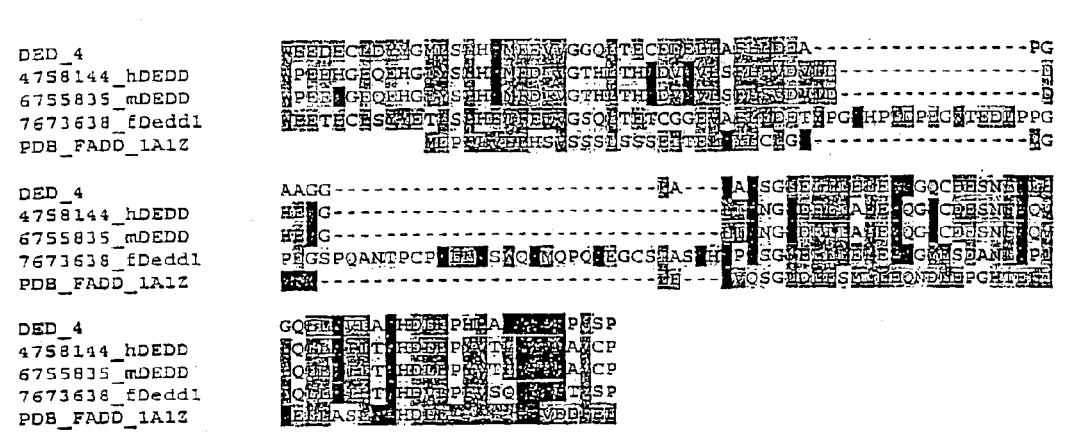

FIG. 9 shows an alignment of the DED domain of DED4 (SEQ ID NO:8) with other DED-containing proteins (hDEDD, SEQ ID NO:36; mDEDD, SEQ ID NO:37; fDEDD, SEQ ID NO:38; FADD, SEQ ID NO:39).

FIGS. 10A and 10B, respectively shows the nucleotide (SEQ ID NO:15)and amino acid (SEQ ID NO:16) sequences of a newly identified variant of IRAK4.

FIG. 11A shows the DD for *Chlamydia muridarum* (SEQ ID NO:53); DD for *Chlamydia pneamoniae* (SEQ ID NO:56); and the DD for *Chiamydophila psittaci* (SEQ ID NO:58); FIGS. 11B and 11C, respectively, show the nucleotide (SEQ ID NO:54) and amino acid (SEQ ID NO:55) sequences of *Chlamydia muridarum,* and the amino acid sequence of *Chlamydia pneumoniae* (SEQ ID NO:57).

DETAILED DESCRIPTION OF THE INVENTION

Figure 1A:
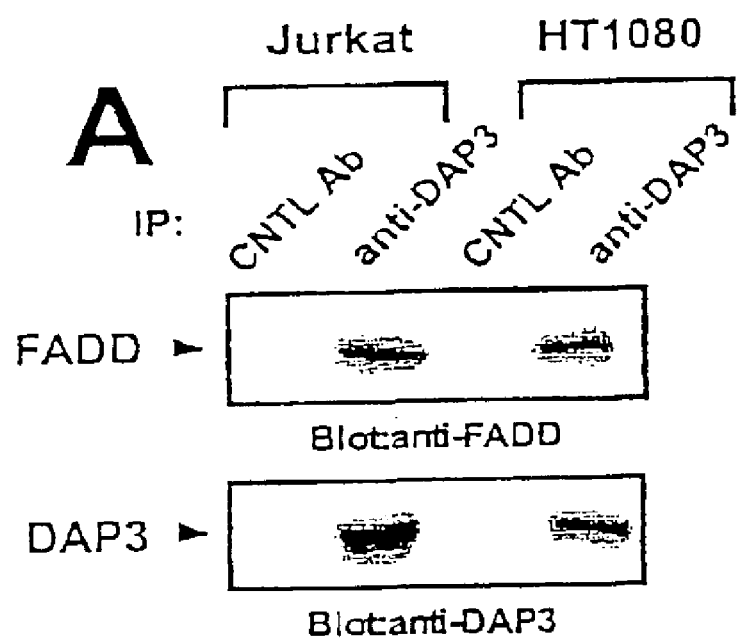
FIG. 1A shows association of endogenous DAP3 with endogenous FADD by immunoprecipitation.

In accordance with the present invention, there are provided novel Death Domains (DDs), Death Effector Domains (DEDs) and NB-ARC domains of newly identified DD and DED proteins, and fragments thereof, as well as novel DD- and DED-containing polypeptides. As used herein, an invention DD can refer to a peptide region that shares sequence homology with the DD domain of DD proteins such as TNFR1, Fas, DR3, DR4/TrailR1, DR5/TrailR2, DR6, FADD, MyD88, Raidd, IRAK, IRAK-2, IRAK-M, p75NTR, Tradd, DAP kinase, RIP, NMP84, and ankyrins, and have been found herein to have binding properties similar to those of other known DD proteins. As used herein, an invention DED can refer to a peptide region that shares sequence homology with the DED domain of DED proteins such as FADD, caspases such as caspases 8 and 10, Flip, PEA15, Flash, BAP31, BAR, DEDT/DEDD, and DAP3, and have been found herein to have binding properties similar to those of other known DED proteins.

Apoptosis-inducing members of the Tumor Necrosis Factor (TNF) receptor family recruit the proforms of caspase-family cell death proteases to liganded receptor complexes through interactions of their intracellular Death Domains (DDs) with adapter proteins (Ashkenazi and Dixit, *Science* 281:1305–1308 (1998); Wallach et al., *Annu. Rev. Immunol.* 17:331–367 (1999)). Several caspase family members are known, for example, caspase-1, caspase-2, caspase-3, caspase-4, caspase-5, caspase-6, caspase-7, caspase-8, caspase-9, caspase-10, caspase-11, caspase-12, caspase-13, and caspase-14 (Grutter, *Curr. Opin. Struct. Biol.* 10:649–655 (2000)). The present invention provides newly identified proteins containing DDs or DEDs. The death domain is a conserved protein interaction domain, which usually participates in signal transduction pathways governed by members of the TNF family of cytokine receptors, Toll-family receptors, and/or regulation of apoptosis.

Death receptors such as TNF-R1 and Fas oligomerize to signal via their intracellular DDs. The signal is transported by cytosolic adapters to caspases. The Death Inducing Signaling Complex (DISC) for Fas has been shown to encompass minimally a Fas trimer, Fadd, and Caspase-8. A similar DISC complex has been found for DR4 and DR5. In the case of the TRAIL receptors, mixed complexes, for example, two DR4s plus one DR5 to form a trimer, appear to be functional. Decoy receptors, for example, DcR1, DcR2 and DcR3, which have no or incomplete death domains, can inhibit apoptosis possibly by interfering with DISC formation. Other types of DED-containing proteins such as mammalian Flip and viral Flip proteins can compete for binding to DISC components, suppressing caspase activation. Caspase activation in the DISC occurs by the "induced proximity" mechanism (Salvesen, *Structure Fold Des.* 7:R225–229 (1999)), the first example of caspase activation by this mechanism.

*Caenorhabiditis elegans* cell death gene ced-4 encodes a protein that contains a CARD domain and a ATP-binding oligomerization domain called an NB-ARC domain (van der Biezen and Jones, *Curr. Biol.* 8:R226–R227). The CARD domain of the CED-4 protein interacts with the CARD domain of a pro-caspase called CED-3. The NB-ARC domain allows CED-4 to self-associate, thereby forming an oligomeric complex which brings associated pro-CED-3 molecules into close proximity to each other. Because most pro-caspases possess at least a small amount of protease activity even in their unprocessed form, the assembly of a complex that brings the proforms of caspase into juxtaposition can result in trans-processing of zymogens, producing the proteolytically processed and active caspase. Thus, CED-4 employs a CARD domain for binding a pro-caspase and an NB-ARC domain for self-oligomerization, resulting in caspase clustering, proteolytic processing and activation.

The nucleotide-binding protein DAP3 (Kissil et al., *J. Biol. Chem.* 270:27932–27936 (1995); Kissil et al., *EMBO J.* 18:353–362 (1999)) was identified as a component of death receptor complexes, during a two-hybrid screen for FADD-binding proteins (Kissil et al., *J. Biol. Chem.* 270:27932–27936 (1995)). As disclosed herein, DAP3 associates with the adapter protein FADD through a domain resembling Death Effector Domains (DEDs) and also binds directly to the DDs of the Trail Receptors DR4 and DR5 via its nucleotide-binding domain, which was determined to bind GTP but not ATP. DAP3 also binds and induces activation of pro-Caspase-8 in vitro in a GTP-dependent manner. Moreover, DAP3 is required in intact cells for efficient caspase activation and apoptosis induction by death receptors based on antisense ablation and experiments with trans-dominant inhibitory DAP3 mutants, including mutation of the nucleotide-binding site in DAP3. Thus, DAP3 represents a functionally important component of the caspase-activating, death-inducing signaling complex (DISC) of TNF-family death receptors, and serves as a molecular bridge that recruits FADD to the TRAIL receptors, DR4 and DR5. The presence of a nucleotide-binding site in DAP3 suggests novel opportunities for pharmacological suppression of death receptor signaling, which could have broad therapeutic applications.

The intracellular regions of several TNFR-family members (TNFR1; p75NTR, neurotrophin receptor, also called p75NGFR, nerve growth factor receptor; Fas; DR3; DR4/TrailR1; DR5/TrailR2; DR6) contain a structure known as the "Death Domain" (DD) and induce apoptosis when bound by ligand (Ashkenazi and Dixit, *Science* 281:1305–1308 (1998); Wallach et al., *Annu. Rev. Immunol.* 17:331–367 (1999)). The mechanism of apoptosis induction by such "death receptors" involves recruitment to the receptor complex of adapter proteins, which bind the prodomains of certain caspase-family cell death proteases. Caspases are present in living cells as zymogens, typically requiring proteolytic processing for their activation. Because the proforms of caspases possess weak protease activity, however, their receptor-mediated clustering results in trans-proteolysis through the "induced proximity" mechanism (Salvesen et al., *Proc. Natl. Acad. Sci. USA* 96:10964–10967 (1999)). It remains unclear what constellation of proteins is required for achieving the correct stoichiometry of receptor complex components, thereby properly positioning the active sites of pro-caspases relative to each other for efficient proteolytic activation of clustered caspase zymogens. Moreover, adapter proteins which recruit caspases to some TNF-family death receptors, such as the Trail receptors DR4 and DR5, are currently unknown (Schneider et al., *Immunity* 7:831–836 (1997); Walczak et al., *EMBO J.* 16:5386–5397 (1997); Kischkel et al., *Immunity* 12:611–620 (2000); Sprick et al., *Immunity* 12:599–609 (2000).

The functions of the DD, DED and NB-ARC domain containing proteins, generally, supports the role of invention DDs, DEDs and NB-ARC domains and invention DD, DED and NB-ARC domain proteins in cellular pathways that effect apoptosis, cell proliferation, cell adhesion, cell stress responses, responses to microbial infection, and B cell immunoglobulin class switching.

For example, invention DDs, DEDs and NB-ARC domains have been found to associate with other proteins, including proteins comprising DD and DED domains. Exemplary DD and DED proteins to which invention DDs, DEDs and NB-ARC domains bind include FADD, caspases such as caspase-8, DR4, DR5, MyD88 and Fas. An invention DD protein IRAK4 was also found to bind to Traf6 and hToll. As used herein, the term "bind" or "binding" refers to the association of an invention DD, DED or NB-ARC polyeptide with another protein relatively specifically and, therefore, can form a bound complex. In particular, the binding of a DD, DED or NB-ARC domain to a protein is sufficiently specific such that the bound complex can form in vivo in a cell or in vitro under suitable conditions.

In one embodiment, it has been found that the invention DAP3 DED (SEQ ID NO:2) binds the DED of FADD. An N-terminal domain of DAP3 containing an NB-ARC domain (SEQ ID NO:4) was also found to bind to caspase-8 and to stimulate pro-caspase-8 protease activity.

Additionally, an N-terminal domain of DAP3 containing an NB-ARC domain (SEQ ID NO:4) was found to bind the DD of DR4, and DAP3 was found to bind to DR5 as well. DAP3 was also found to bind GTP, and GTP binding was found to be critical for DAP3 interactions with FADD and caspase-8 but not for TRAIL receptors such as DR4 and DR5. Furthermore, it was found that DAP3 deletion mutants at the N-terminus and C-terminus (DAP3ΔN and DAP3ΔC, respectively) inhibited FADD-induced activation of pro-caspase-8. Therefore, DAP3 domains, including DED domain, can function as inhibitors of FADD-induced activation of pro-caspase-8.

In another embodiment, it has been found that IRAK4 can bind to TRAF6, hToll and MyD88. IRAK4 was also found to stimulate NFκB activation. Overexpression of a dominant-negative form of TRAF6 inhibited the IRAK4-mediated NFκB activation. The IRAK4 DD functions as a dominant negative of MyD88-induced NFκB activation and can bind the DD of MyD88. The invention provides an IRAK4 DD (SEQ ID NO:6).

In still another embodiment, a *Chlamydia trachomatis* DD protein (CTDD) (SEQ ID NO: 10) was found to bind to various DD containing proteins, including FasR, DR4 and DR5. The invention also provides a DD from *Chlamydia muridarum* (SEQ ID NO: 53), *Chlamydia pneumoniae* (SEQ ID NO:56), and *Chlamydophila psittaci* (SEQ ID NO: 58). In yet another embodiment, a new DED-containing protein, designated DED4, was identified. Thus, the invention provides a DED4 DED (SEQ ID NO:8).

In another embodiment, a mouse DD-containing protein, NIDD, was found to interact with itself and with p75NTR, also known as neurotrophin receptor or nerve growth factor (NGF) receptor. Thus, the invention provides a NIDD DD (SEQ ID NO:12).

It has also been found that invention DDs, DEDs and NB-ARC domains modulate a variety of cellular pathways. Proteins that bind to the invention DDs, DEDS, and NB-ARC domains, generally, are well known in the art as modulating the cellular pathways that effect apoptosis, cell proliferation, cell adhesion, cell stress responses, responses to microbial infection, and B cell immunoglobulin class switching, and NF-κB and JNK are further known to modulate these pathways. Thus, those of skill in the art will recognize that it is within the scope of the invention that DDs, DEDs and NB-ARCs, as well as other newly identified domains, modulate one or more cellular pathways that effect apoptosis, cell proliferation, cell adhesion, cell stress responses, responses to microbial infection, and B cell immunoglobulin class switching.

Presently preferred DDs, DEDs and NB-ARC domain of the invention include amino acid sequences that comprise the same or substantially the same protein sequence set forth in SEQ ID NOS:2, 4, 6, 8, 10, 12, 53, 56 and 58, as well as biologically active, modified forms thereof. The invention also provides DD, DED and NB-ARC domain polypeptides having the same or substantially the same sequence as SEQ ID NOS:18 or 22.

In another embodiment, invention DDs, DEDs and NB-ARC domains include proteins comprising fragments having the sequence SEQ ID NOS:2, 4, 6, 8, 10, 12, 53, 56 or 58, or polypeptides having the sequence SEQ ID NOS:16, 18, 20, 22 or 26, which retain at least one native biological DD, DED or NB-ARC activity, such as immunogenicity, the ability to bind to FADD, caspases such as caspase-8, DR4, DR5, TRAF6, hToll, MyD88, and Fas, or other polypeptides, as disclosed herein, the ability to modulate apoptosis, cell proliferation, cell adhesion, cell stress responses, responses to microbial infection, or B cell immunoglobulin class switching.

Use of the terms "isolated" and/or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment, and are substantially free of any other species of nucleic acid or protein. As a result of this human intervention, the recombinant DNAs, RNAs, polypeptides and proteins of the invention are useful in ways described herein that the DNAs, RNAs, polypeptides or proteins as they naturally occur are not.

As used herein, "eukaryotic" refers to the variety of species from which an invention DD, DED or NB-ARC is derived, e.g., yeast, slime mold, plant, insect, nematode, mammal, and the like. A preferred DD, DED or NB-ARC domain polypeptide herein is mammalian DAP3, IRAK4, DED4 and NIDD. The invention also provides a DD protein from *Chlamydia* and, therefore, an invention DD can be from bacteria. As used herein, "mammalian" refers to the variety of species from which a preferred invention DD, DED or NB-ARC is derived, e.g., human, rat, mouse, rabbit, monkey, baboon, bovine, porcine, ovine, canine, feline, and the like.

The term "biologically active" or "functional", when used herein as a modifier of invention DDs, DEDs or NB-ARC domain, or polypeptide fragment thereof, refers to a polypeptide that exhibits functional characteristics similar to an invention DD, DED or NB-ARC domain. For example, one biological activity of a DD, DED or NB-ARC domain is the ability to bind, preferably in vivo, to a molecule in apoptotic pathways such as FADD, caspases such as caspase-8, DR4, DR5, TRAF6, hToll, MyD88, and Fas proteins. Such DD, DED or NB-ARC binding activity can be assayed, for example, using the methods described in the Examples described herein.

Another biological activity of DD, DED or NB-ARC is the ability to act as an immunogen for the production of polyclonal and monoclonal antibodies that bind specifically to an invention DD, DED or NB-ARC domain. Thus, an invention DD, DED or NB-ARC will encode a polypeptide specifically recognized by an antibody that also specifically recognizes the DDs, DEDs or NB-ARC domains having the amino acid sequence SEQ ID NOS:2, 4, 6, 8, 10, 12, 53, 56 or 58. Such immunologic activity can be assayed by any method known to those of skill in the art. For example, a test DD, DED or NB-ARC polypeptide can be used to produce antibodies, which are then assayed for their ability to bind to an invention DD, DED or NB-ARC comprising SEQ ID NOS:2, 4, 6, 8, 10, 12, 53, 56 or 58. If the antibody binds to the test polypeptide and a protein including the sequence SEQ ID NOS:2, 4, 6, 8, 10, 12, 53, 56 or 58, with the same or substantially the same affinity, then the polypeptide possesses the requisite immunologic biological activity. Similarly, a biological activity of an invention DD or DED polypeptide, including those having SEQ ID NOS:16, 18, 20, 22 or 26, and more preferably SEQ ID NOS:18 or 22, can also have an immunologic biological activity.

The DED-containing protein DAP3 set forth in SEQ ID NO:14 was initially identified as and implicated in death receptor-mediated apoptosis through unknown mechanisms (Kissil et al., *EMBO J.* 18:353–362 (1999)). A NB-ARC domain was also identified in DAP3. The subject application represents the first identification of a portion of this protein as forming a DED and NB-ARC domain.

The DD-containing protein IRAK4 set forth in SEQ ID NO:16 was initially identified as a putative protein kinase (Scanlan et al., *Int. J. Cancer* 83:456–464 (1999); GenBank GI|15360131, putative protein kinase NY-REN-64 antigen). The subject application represents the first identification of a portion of this protein as forming a DD domain. In addition, the IRAK4 protein set forth in SEQ ID NO:16 contains four amino acid changes compared to the GenBank sequence.

The DD-containing protein CTDD set forth in SEQ ID NO:20 was found in the genome of *Chlamydia trachomatis*. The subject application represents the first identification of a portion of this protein as forming a DD domain. In addition, the CTDD protein set forth in SEQ ID NO:20 contains one amino acid change compared to the GenBank sequence of CT-610 from *Chlamydia trachomatis*. The invention further provides other DD-containing proteins and domains of other *Chlamydia* species, including *Chlamydia muridarum*, as disclosed herein.

The DED-containing protein DED4 set forth in SEQ ID NO:18 was identified as a relative of DEDD. DED4 was predicted from nucleotide sequences (chromosomal DNA and EST DNA) GI Nos. 4210498, 1832773, and 6990020. The subject application represents the first identification of a protein comprising the DED4 sequence or a portion of this protein as forming a DED domain.

The DD-containing protein NIDD (NGF receptor-interacting death domain) set forth in SEQ ID NO:22 was identified and found to bind to itself or NGF receptor. The NIDD protein was predicted from mouse nucleotide sequences (EST database at NCBI, GI 5353348), and rat and bovine homologues (GI 4607778 and GI 6960635, respectively) were also found. The subject application represents the first identification of a protein comprising the NIDD sequence or a portion of this protein as forming a DD domain.

In accordance with one embodiment of the invention, it has been found that the invention DAP3 DED (SEQ ID NO:2) binds the DED of FADD. An N-terminal domain of DAP3 containing a NB-ARC domain (SEQ ID NO:4) was also found to bind to caspase-8 and to stimulate pro-caspase-8 protease activity. Additionally, an N-terminal domain of DAP3 containing a NB-ARC domain (SEQ ID NO:4) was found to bind the DD of DR4, and DAP3 was found to bind to DR5 as well. DAP3 was also found to bind GTP, and GTP binding was found to be critical for DAP3 interactions with FADD and caspase-8 but not for TRAIL receptors such as DR4 and DR5. Furthermore, it was found that DAP3 deletion mutants at the N-terminus and C-terminus (DAP3ΔN and DAP3ΔC, respectively) inhibited FADD-induced activation of pro-caspase-8. Therefore, DAP3 domains, including DED domain, can function as inhibitors of FADD-induced activation of pro-caspase-8.

In another embodiment, the invention provides an IRAK4 DD (SEQ ID NO: 6) and that IRAK4 can bind to TRAF6, hToll and MyD88. IRAK4 was also found to stimulate NFκB activation. Overexpression of a dominant negative form of TRAF6 inhibited the IRAK4-mediated NFκB activation. The IRAK4 DD functions as a dominant negative of MyD88-induced NFκB activation.

In still another embodiment, a *Chlamydia trachomatis* DD protein (CTDD) (SEQ ID NO:10) was found to bind to various DD-containing proteins, including FasR, DR4 and DR5. In yet another embodiment, a new DED-containing protein, designated DED4, was identified. Thus, the invention provides a DED4 DED (SEQ ID NO:8). The invention also provides a new protein, NIDD, containing a DD (SEQ ID NO:12), that binds to NGF receptor.

Those of skill in the art will recognize that numerous residues of the above-described sequences can be substituted with other, chemically, sterically and/or electronically similar residues without substantially altering the biological activity of the resulting receptor species. In addition, larger polypeptide sequences containing the same or substantially the same sequence as amino acids set forth in SEQ ID NOS:2, 4, 6, 8, 10, 12, 53, 56 and 58, therein (e.g., splice variants) are contemplated, provided that the sequence is not SEQ ID NOS:14, 24, 28, 55 or 57.

As employed herein, the term "substantially the same amino acid sequence" refers to amino acid sequences having at least about 70% identity with respect to the reference amino acid sequence, and retaining comparable functional and biological activity characteristic of the protein defined by the reference amino acid sequence. Preferably, proteins having "substantially the same amino acid sequence" will have at least about 80%, more preferably 90% amino acid identity with respect to the reference amino acid sequence; with greater than about 95% amino acid sequence identity being especially preferred. It is recognized, however, that polypeptides (or nucleic acids referred to hereinbefore) containing less than the described levels of sequence identity arising as splice variants or that are modified by conservative amino acid substitutions, or by substitution of degenerate codons are also encompassed within the scope of the present invention. Identity of any two amino acid sequences can be determined by those skilled in the art based, for example, on a BLAST 2.0 computer alignment, using default parameters (Altschul et al., *J. Mol. Biol.* 215:403–410 (1990); Gish and States, *Nature Genet.* 3:266–272 (1993); Madden et al., *Meth. Enzymol.* 266:131–141 (1996); Altschul et al., *Nucleic Acids Res.* 25:3389–3402 (1997); Zhang and Madden, *Genome Res.* 7:649–656 (1997)).

The invention DDs, DEDs and NB-ARC domains can be isolated by a variety of methods well-known in the art, e.g., recombinant expression systems described herein, precipitation, gel filtration, ion-exchange, reverse-phase and affinity chromatography, and the like. Other well-known methods are described in Deutscher et al., *Guide to Protein Purification: Methods in Enzymology Vol.* 182, (Academic Press, (1990)), which is incorporated herein by reference. Alternatively, the isolated polypeptides of the present invention can be obtained using well-known recombinant methods as described, for example, in Sambrook et al., *Molecular Cloning, A Laboratory Manual,* 2nd ed., Cold Spring Harbor Laboratory Press, Plainview N.Y. (1989)).

An example of the means for preparing the invention DD(s), DED(s) or NB-ARC domain(s) is to express nucleic acids encoding the DD, DED or NB-ARC domain in a suitable host cell, such as a bacterial cell, a yeast cell, an amphibian cell (i.e., oocyte), or a mammalian cell, using methods well known in the art, and recovering the expressed polypeptide, again using well-known methods. Invention polypeptides can be isolated directly from cells that have been transformed with expression vectors as described below herein. The invention polypeptide, biologically functional fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

Also encompassed by the term DD, DED or NB-ARC domains are functional fragments or polypeptide analogs thereof. The term "functional fragment" refers to a peptide fragment that is a portion of a full length DD, DED, or NB-ARC domain provided that the portion has a biological activity, as defined above, that is characteristic of the corresponding full length protein. For example, a functional fragment of an invention DD, DED or NB-ARC domain can have an activity such as the ability, for example, to bind FADD, caspases such as caspase-8, DR4, DR5, TRAF6, hToll, MyD88, Fas, or p75NTR proteins, or to modulate NF-κB activity or JNK activity, or to modulate the level of cell proliferation, apoptosis, cell adhesion, cell stress responses, responses to microbial infection, class switching, and the like. In addition, the characteristic of a functional fragment of invention DDs, DEDs or NB-ARC domains to elicit an immune response is useful for obtaining an anti-DD, anti-DED or anti-NB-ARC antibodies. Thus, the invention also provides functional fragments of invention DDs, DEDs, or NB-ARCs which can be identified using the binding and routine methods, such as bioassays described herein.

The term "polypeptide analog" includes any polypeptide having an amino acid residue sequence substantially the same as a sequence specifically shown herein in which one or more residues have been conservatively substituted with a functionally similar residue and which displays the ability to functionally mimic a DD, DED or NB-ARC domain as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The amino acid length of a peptide, functional fragment, or polypeptide analog of the present invention can range from about 5 amino acids up to one residue less than a full-length protein sequence of an invention DD, DED or NB-ARC. In certain embodiments, the amino acid lengths include, for example, at least about 10 amino acids, at least about 20, at least about 30, at least about 40, at least about 50, at least about 75, at least about 100, at least about 150, at least about 200, at least 213, at least about 250, at least about 300, at least about 350 or more amino acids in length up to one residue less than a full-length DD-, DED, or NB-ARC domain-containing protein sequence.

Preferably, a fragment comprises a sequence selected from SEQ ID NOS:2, 4, 6, 8, 10, 12, 53, 56 or 58. Such a fragment can also include, in addition to invention DDs, DEDs, or NB-ARC domains, at least about 10 residues at its amino-terminus, carboxy-terminus, or both; at least about 20 residues at its amino-terminus, carboxy-terminus, or both; at least about 30 residues at its amino-terminus, carboxy-terminus, or both; at least about 40 residues at its amino-terminus, carboxy-terminus, or both; at least about 50 residues at its amino-terminus, carboxy-terminus, or both; at least about 60 residues at its amino-terminus, carboxy-terminus, or both; at least about 100 residues at its amino-terminus, carboxy-terminus, or both. A fragment can also include, in addition to invention DDs, DEDs, or NB-ARC domains, less than about 10 residues at its amino-terminus, carboxy-terminus, or both; less than about 20 residues at its amino-terminus, carboxy-terminus, or both; less than about 30 residues at its amino-terminus, carboxy-terminus, or both; less than about 40 residues at its amino-terminus, carboxy-terminus, or both; less than about 50 residues at its amino-terminus, carboxy-terminus, or both; less than about 60 residues at its amino-terminus, carboxy-terminus, or both; less than about 100 residues at its amino-terminus, carboxy-terminus, or both.

More preferably, a fragment comprises a sequence selected from SEQ ID NOS:2, 4, 6, 8, 10, 12, 53, 56 or 58, further comprising one or more domains selected from DAP3, IRAK4, CTDD, DED4 or NIDD. Most preferably, a fragment has at least one fewer domains than the domains in proteins from SEQ ID NOS:14, 16, 18, 20, or 22, wherein the domains are selected from those present in DAP3, IRAK4, CTDD, DED4 or NIDD, either domains previously identified or domains newly identified as disclosed herein. Identification of the domains in proteins from SEQ ID NOS:14, 16, 18, 20 or 22 can be carried out by reference to publications reporting such proteins (e.g., Kissil et al., *EMBO J*. 18:353–362 (1999) for DAP3). A fragment can also comprise a sequence selected from SEQ ID NOS:2, 4, 6, 8, 10, 12, 53, 56 or 58 having at least one fewer amino acids than in SEQ ID NOS:14, 16, 18, 20 or 22.

As used herein the phrase "conservative substitution" also includes the use of a chemically derivatized residue in place of a non-derivatized residue, provided that such polypeptide displays the required binding activity. The phrase "chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions of residues, relative to the sequence of a polypeptide whose sequence is shown herein, so long as the required activity is maintained.

In accordance with another embodiment, novel DD-, DED-, or NB-ARC-containing proteins are provided. Invention DD-, DED-, or NB-ARC-containing proteins refer to a protein comprising an invention DD, DED, or NB-ARC including SEQ ID NOS:2, 4, 6, 8, 10, 12, 53, 56 or 58, or a recombinantly produced invention DD-, DED-, or NB-ARC-containing protein, including naturally occurring allelic variants thereof encoded by mRNA generated by alternative splicing of a primary transcript, provided the DD-, DED-, or NB-ARC-containing proteins are not the sequence SEQ ID NOS:14, 24 or 28. An invention DD- or DED-containing protein can include SEQ ID NOS:16, 18, 20, or 22, or a protein containing a partial DD sequence such as SEQ ID NO:26. Preferably, a DD-, DED-, or NB-ARC-containing protein comprises an invention DD, DED or NB-ARC domain with a sequence the same or substantially the same as SEQ ID NOS:2, 4, 6, 8, 10, 12, 53, 56 or 58, and can be the same or substantially the same sequence as SEQ ID NOS:18 or 22. More preferably, a DD-, DED-, or NB-ARC-containing protein comprises an invention DD, DED or NB-ARC with the sequence of SEQ ID NOS:2, 4, 6, 8, 10, 12, 16, 18, 20, 22, 53, 56 or 58.

A DD-, DED-, NB-ARC-containing protein comprising an invention DD, DED or NB-ARC domain is further characterized as binding FADD, caspases such as caspase-8, DR4, DR5, TRAF6, hToll, MyD88, or Fas proteins, or to modulate NF-κB activity or JNK activity; or modulating apoptosis, cell proliferation, cell adhesion, cell stress responses, responses to microbial infection, or B cell immunoglobulin class switching; or any combination thereof.

In another embodiment of the invention, DD-, DED-, or NB-ARC-containing chimeric proteins are provided comprising an invention DD, DED, or NB-ARC domain or fragments thereof, having the sequence of SEQ ID NOS:2, 4, 6, 8, 10, 12, 53, 56 or 58, and further comprising one or more sequences from a heterologous protein. For example, an invention DD-DED- or NB-ARC domain can be fused to a RING finger domain, which has E3 activity. An F box protein can function to target Skp1-E3 complex for proteosome-dependent degradation (Tyers and Jorgensen, Curr. Opin. Genet. Dev. 10:54–64 (2000)). Invention DD-, DED-, or NB-ARC-containing chimeric proteins include, for example, polypeptides having the sequence SEQ ID NOS:2, 4, 6, 8, 10, 12, 53, 56 or 58. An invention chimeric protein can also comprise a portion of a polypeptide having the sequence SEQ ID NOS:18 or 22. Sequences from heterologous proteins with which the DD, DED, or NB-ARC domain, or a functional fragment thereof, are fused will include, for example, glutathione-S-transferase, an antibody, or other proteins or functional fragments thereof which facilitate recovery of the chimera. Further, proteins with which the DD, DED, or NB-ARC domain or functional fragment thereof, are fused will include, for example, luciferase, green fluorescent protein, an antibody, or other proteins or functional fragments thereof which facilitate identification of the chimera. Still further proteins with which the DD, DED, or NB-ARC domain or functional fragment thereof, are fused will include, for example, the LexA DNA binding domain, ricin, α-sarcin, an antibody, or other proteins which have therapeutic properties or other biological activity.

As such chimeric proteins include sequences from two different proteins, the resultant amino acid sequence of the chimeric protein will typically be a non-naturally occurring sequence. Thus, in accordance with this embodiment of the invention, there are provided chimeric proteins comprising an invention DD, DED, or NB-ARC domain, or fragments thereof, having the sequence of SEQ ID NOS:2, 4, 6, 8, 10, 12, 53, 56 or 58, provided the sequence of the chimeric protein is not naturally occurring.

Further invention chimeric proteins contemplated herein are chimeric proteins wherein an invention DD, DED or NB-ARC is combined with one or more domains selected from apoptotic proteins from a heterologous protein.

Another embodiment of the invention provides DD, DED, or NB-ARC, or a functional fragment thereof, fused with a moiety to form a conjugate. As used herein, a "moiety" can be a physical, chemical or biological entity which contributes functionality to DD, DED or NB-ARC, or a functional fragment thereof. Functionalities contributed by a moiety include therapeutic or other biological activity, or the ability to facilitate identification or recovery of DD, DED or NB-ARC. Therefore, a moiety will include molecules known in the art to be useful for detection of the conjugate by, for example, by fluorescence, magnetic imaging, detection of radioactive emission, and the like. A moiety may also be useful for recovery of the conjugate, for example a His tag or other known tags used for protein isolation/purification, or a physical substance such as a bead. A moiety can be a therapeutic compound, for example, a cytotoxic drug which can be useful to effect a biological change in cells to which the conjugate localizes.

In accordance with another embodiment of the invention there are provided oligomers comprising invention DDs, DEDs, or NB-ARC domains and fragments thereof, invention DD-, DED-, or NB-ARC-containing proteins, DD-, DED-, or NB-ARC-containing chimeric proteins, or combinations thereof. In one embodiment, the invention comprises homo-oligomers of invention DDs, DEDs or NB-ARC domains and fragments thereof, invention DD-, DED- or NB-ARC-containing proteins, DD-, DED- or NB-ARC-containing chimeric proteins, or combinations thereof.

In another embodiment of the invention, there are provided hetero-oligomers comprising invention DDs, DEDs, or NB-ARC domains and fragments thereof, invention DD-, DED- or NB-ARC-containing proteins, DD-, DED- or NB-ARC-containing chimeric proteins, or combinations thereof. Thus hetero-oligomers comprising invention DDs, DEDs or NB-ARC domains and fragments thereof, invention DD-, DED- or NB-ARC-containing proteins, DD-, DED- or NB-ARC-containing chimeric proteins, or combinations thereof, and further comprising FADD, caspases such as caspase-8, DR4, DR5, TRAF6, hToll, MyD88, and Fas, or combinations thereof. For example, the DAP3 DED (SEQ ID NO:2) can form a hetero-oligomer with FADD, caspase-8, DR4, DR5, or combinations thereof. In another example, the IRAK4 DD (SEQ ID NO:6) can form a hetero-oligomer with TRAF6, hToll, MyD88, or combinations thereof. In a further example, the CTDD (SEQ ID NO:10) can form a hetero-oligomer with caspase-8, DR4, DR5, Fas, or combinations thereof.

In accordance with another embodiment of the invention, there are provided isolated nucleic acids, which encode a novel DD, DED, or NB-ARC and fragments thereof, DD-, DED- or NB-ARC-containing proteins and DD-, DED- or NB-ARC-containing chimeric proteins. Nucleic acids that encode a invention DD, DED or NB-ARC are those that encode a protein with the ability to bind, preferably in vivo, to one or more of FADD, caspases such as caspase-8, DR4, DR5, TRAF6, hToll, MyD88, and Fas, or any combination thereof, or have the ability to modulate NF-κB activity, JNK activity, apoptosis, cell proliferation, cell adhesion, cell stress responses, responses to microbial infection, or B cell immunoglobulin class switching. An invention nucleic acid encodes a DD, DED or NB-ARC domain having the sequence SEQ ID NOS:2, 4, 6, 8, 10, 12, 53, 56 or 58, or a DD- or DED-containing polyepeptide encoding SEQ ID NOS:16, 18, 20 or 22, or a polypeptide having SEQ ID NO:26.

The nucleic acid molecules described herein are useful for producing invention proteins, when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of an invention DD, DED or NB-ARC domain gene or mRNA transcript in a given sample. The nucleic acid molecules described herein, and fragments thereof, are also useful as primers and/or templates in a Polymerase Chain Reacion (PCR) for amplifying genes encoding invention proteins described herein.

The term "nucleic acid" (also referred to as polynucleotides) encompasses ribonucleic acid (RNA) or deoxyribonucleic acid (DNA), probes, oligonucleotides, and primers. DNA can be either complementary DNA (cDNA) or genomic DNA, e.g. a gene encoding a DD, DED or NB-ARC domain. In addition, a nucleic acid can be single-stranded, double-stranded, a sense strand or an anti-sense strand. One means of isolating a nucleic acid encoding a DD, DED, or NB-ARC domain or polypeptide is to probe a mammalian genomic library with a natural or artificially designed DNA probe using methods well known in the art. DNA probes derived from the DD, DED or NB-ARC gene are particularly useful for this purpose. Oligonucleotides are useful, for example, as probes or as primers for amplification reactions such as the polymerase chain reaction (PCR). DNA and cDNA molecules that encode DDs, DEDs or NB-ARC domain can be used to obtain complementary genomic DNA, cDNA or RNA from bacterial, eukaryotic (e.g., human, primate, mammal, plant, nematode, insect, yeast, and the like), or mammalian sources, or to isolate related cDNA or genomic clones by the screening of cDNA or genomic libraries, by methods described in more detail below. Examples of nucleic acids are RNA, cDNA, or isolated genomic DNA encoding a DD, DED or NB-ARC domain, provided the nucleic acids do not comprise the nucleotide sequence set forth in SEQ ID NOS:13, 23, 27, or 54 or nucleic acid encoding SEQ ID NO:57. The invention also provides nucleic acids referenced as SEQ ID NOS:15, 17, 19, 21 and 25. Such nucleic acids can include, but are not limited to, nucleic acids comprising the same or substantially the same nucleotide sequence as set forth in SEQ ID NOS:1, 3, 5, 7, 9, 11 or 52.

In one embodiment of the present invention, cDNAs encoding the invention DD, DED or NB-ARC domain disclosed herein comprise the same or substantially the same nucleotide sequence as set forth in SEQ ID NOS:1, 3, 5, 7, 9, 11, or 52, provided they do not comprise the sequence set forth in SEQ ID NO:13, 15, 19, 23, 25, 27, or 54, or a nucleic acid encoding SEQ ID NO:57. Preferred cDNA molecules encoding the invention proteins comprise the same nucleotide sequence as set forth in SEQ ID NOS:1, 3, 5, 7, 9, 11 or 52.

In another embodiment of the present invention, cDNAs encoding the invention DDs, DEDs or NB-ARC domains disclosed herein comprise the same or substantially the same nucleotide sequence as set forth in SEQ ID NOS:1, 3, 5, 7, 9, 11 or 52. Preferred cDNA molecules encoding the invention proteins comprise the same nucleotide sequence as set forth in SEQ ID NOS:1, 3, 5, 7, 9, 11 or 52.

cDNA molecules SEQ ID NOS:1, 3, 5, 7, 9, 11 or 52 encoding the invention DD, DED or NB-ARC domains respectively represent the same nucleotide sequence as nucleotides 416–712 and 875–1084 set forth in SEQ ID NO:13; nucleotides 25–318 set forth in SEQ ID NO:15; nucleotides 268–462 set forth in SEQ ID NO:17; nucleotides 124–426 set forth in SEQ ID NO:19; nucleotides 418–630 set forth in SEQ ID NO:21.

As employed herein, the term "substantially the same nucleotide sequence" refers to DNA having sufficient identity to the reference polynucleotide, such that it will hybridize to the reference nucleotide under moderately stringent hybridization conditions. In one embodiment, DNA having substantially the same nucleotide sequence as the reference nucleotide sequence encodes substantially the same amino acid sequence as that set forth in any of SEQ ID NOS:2, 4, 6, 8, 10, 12, 18, 22, 53, 56 or 58, provided the DNA does not encode the sequence set forth in SEQ ID NOS:14, 24, 28, 55 or 57. In another embodiment, DNA having "substantially the same nucleotide sequence" as the reference nucleotide sequence has at least 60% identity with respect to the reference nucleotide sequence. DNA having at least 70%, more preferably at least 90%, yet more preferably at least 95%, identity to the reference nucleotide sequence is preferred. Identity of any two nucleic acid sequences can be determined by those skilled in the art based, for example, on a BLAST 2.0 computer alignment, using default parameters. BLAST 2.0 searching is available at http://www.ncbi.nlm.nih.gov/gorf/b12.html., as described by Tatiana et al., *FEMS Microbiol Lett.* 174:247–250 (1999).

This invention also encompasses nucleic acids which differ from the nucleic acids shown in SEQ ID NOS:1, 3, 5, 7, 9, 11 and 52, but which have the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same protein product(s) as the nucleic acids disclosed herein. In particular, functionally equivalent nucleic acids encode polypeptides that are the same as those encoded by the nucleic acids disclosed herein or that have conservative amino acid variations. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding DDs, DEDs or NB-ARC domains that, by virtue of the degeneracy of the genetic code, do not necessarily hybridize to the invention nucleic acids under specified hybridization conditions. Preferred nucleic acids encoding the invention DDs, DEDs or NB-ARC domain are comprised of nucleotides that encode substantially the same amino acid sequence as set forth in SEQ ID NOS:2, 4, 6, 8, 10, 12, 18, 22, 53, 56 or 58, provided they do not encode the sequence set forth in SEQ ID NOS:14, 24, 28, 55 or 57.

Thus, an exemplary nucleic acid encoding an invention DD, DED, or NB-ARC can be selected from:
(a) DNA encoding the amino acid sequence set forth in SEQ ID NOS:2, 4, 6, 8, 10, 12, 53, 56 or 58;
(b) DNA that hybridizes to the DNA of (a) under moderately stringent conditions, wherein said DNA encodes biologically active DD, DED, or NB-ARC, or
(c) DNA degenerate with (b), wherein said DNA encodes biologically active DD, DED, or NB-ARC domain.

Another exemplary nucleic acid encoding an invention DD, DED or NB-ARC domain can be selected from:
(a) DNA encoding the amino acid sequence set forth in SEQ ID NOS:2, 4, 6, 8, 10, 12, 53, 56 or 58;
(b) DNA that hybridizes to the DNA of (a) under moderately stringent conditions, wherein said DNA encodes biologically active DD, DED, or NB-ARC domain or
(c) DNA degenerate with (b), wherein said DNA encodes biologically active DD, DED, or NB-ARC domain, wherein the nucleic acid sequence does not encode the amino acid sequence set forth in SEQ ID NOS:14, 24, 28, 55 or 57.

The invention additionally provides an isolated nucleic acid encoding a Death Domain (DD), Death Effector Domain (DED) or NB-ARC domain polypeptide, or functional fragments thereof, the nucleic acid encoding the amino acid sequence set forth in SEQ ID NOS:2, 4, 6, 8, 10, 12, 16, 18, 20, 22, 26, 53, 56 or 58. The invention also provides a nucleic acid having the same or substantially the same sequence as set forth in any of SEQ ID NOS:1, 3, 5, 7, 9, 11, 17, 21 or 52. The invention also provides a nucleic acid having the same sequence as that set forth in any of SEQ ID NOS:1, 3, 5, 7, 9, 11, 15, 17, 19, 21, 25 or 52.

Hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature ($T_m$) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being especially preferred. Preferably, moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C.

The phrase "high stringency hybridization" refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5× Denhart's solution, 5×SSPE, 0.2% SDS at 42° C., followed by washing in 0.1×SSPE, and 0.1% SDS at 65° C.

The phrase "low stringency hybridization" refers to conditions equivalent to hybridization in 10% formamide, 5× Denhart's solution, 6×SSPE, 0.2% SDS at 42° C., followed by washing in 1×SSPE, 0.2% SDS, at 50° C. Denhart's solution and SSPE (see, e.g., Sambrook et al., supra, 1989) are well known to those of skill in the art as are other suitable hybridization buffers.

As used herein, the term "degenerate" refers to codons that differ in at least one nucleotide from a reference nucleic acid, e.g., SEQ ID NOS:1, 3, 5, 7, 9, 11 or 52, but encode the same amino acids as the reference nucleic acid. For example, codons specified by the triplets "UCU", "UCC", "UCA", and "UCG" are degenerate with respect to each other since all four of these codons encode the amino acid serine.

Preferred nucleic acids encoding the invention polypeptide(s) hybridize under moderately stringent, preferably high stringency, conditions to substantially the entire sequence, or substantial portions (i.e., typically at least 15–30 nucleotides) of the nucleic acid sequence set forth in SEQ ID NOS:1, 3, 5, 7, 9, 11, 52, provided they do not comprise the sequence set forth in SEQ ID NOS:13, 23, 27 or 54, or a nucleic acid encoding SEQ ID NO:57.

The invention nucleic acids can be produced by a variety of methods well-known in the art, e.g., the methods described herein, employing PCR amplification using oligonucleotide primers from various regions of SEQ ID NOS:1, 3, 5, 7, 9, 11 or 52, and the like.

In accordance with a further embodiment of the present invention, optionally labeled DD, DED or NB-ARC encoding cDNAs, or fragments thereof, can be employed to probe library(ies) (e.g., cDNA, genomic, and the like) for additional nucleic acid sequences encoding novel bacterial or eukaryotic DD, DED or NB-ARC domains. Construction of suitable bacterial libraries or eukaryotic cDNA libraries is well-known in the art. Screening of such a cDNA library is initially carried out under low-stringency conditions, which comprise a temperature of less than about 42° C., a formamide concentration of less than about 50%, and a moderate to low salt concentration.

Presently preferred probe-based screening conditions comprise a temperature of about 37° C., a formamide concentration of about 20%, and a salt concentration of about 5× standard saline citrate (SSC; 20×SSC contains 3M sodium chloride, 0.3M sodium citrate, pH 7.0). Such conditions will allow the identification of sequences which have a substantial degree of similarity with the probe sequence, without requiring perfect homology. The phrase "substantial similarity" refers to sequences which share at least 50% homology. Preferably, hybridization conditions will be selected which allow the identification of sequences having at least 70% homology, at least 80%, at least 90%, at least 95%, or at least 98% with the probe, while discriminating against sequences which have a lower degree of homology with the probe. As a result, nucleic acids having the same or substantially the same nucleotide sequence as SEQ ID NOS:13, 15, 17, 19, 21, 25, 27 or 54 are obtained.

As used herein, a nucleic acid "probe" or "oligonucleotide" is single-stranded or double-stranded DNA or RNA, or analogs thereof, that has a sequence of nucleotides that includes at least 15, at least 20, at least 50, at least 100, at least 200, at least 300, at least 400, or at least 500 contiguous bases that are the same as (or the complement of) any contiguous bases set forth in any of SEQ ID NOS:1, 3, 5, 7, 9, 11, 15, 17, 19, 21 or 52. Oligonucleotides are useful, for example, as probes or as primers for amplification reactions such as the polymerase chain reaction (PCR). In addition, oligonucleotides can bind to the sense or anti-sense strands of other nucleic acids. Preferred regions from which to construct probes include 5' and/or 3' coding regions of SEQ ID NOS:1, 3, 5, 7, 9, 11, 15, 17, 19, 21 or 52. In addition, the entire cDNA encoding region of an invention DD, DED, or NB-ARC domain or the entire sequence corresponding to SEQ ID NOS:1, 3, 5, 7, 9, 11, 15, 17, 19, 21 or 52 can be used as a probe. Probes can be labeled by methods well-known in the art, as described hereinafter, and used in various diagnostic kits.

It is understood that an invention nucleic acid molecule, as used herein, specifically excludes previously known nucleic acid molecules consisting of nucleotide sequences having identity with the DD, DED and NB-ARC nucleotide sequence, such as Expressed Sequence Tags (ESTs), Sequence Tagged Sites (STSs) and genomic fragments, deposited in public databases such as the nr, dbest, dbsts, gss and htgs databases, which are available for searching at http://www.ncbi.nlm.nih.gov/blast/blast.cgi?Jform=0, using the program BLASTN 2.0.9 described by Altschul et al., *Nucleic Acids Res.* 25:3389–3402 (1997).

In particular, a DD, DED or NB-ARC domain nucleic acid molecule specifically excludes nucleic acid molecules consisting of any of the nucleotide sequences having the Genbank (gb), EMBL (emb) or DDBJ (dbj) accession numbers described below. Similarly, a DD, DED or NB-ARC domain polypeptide fragment of DD, DED or NB-ARC domain containing-polypeptide specifically excludes the amino acid fragments encoded by the nucleotide sequences having the GenBank accession numbers described below. GenBank accession numbers specifically excluded include AW449244, AA218681, GI 4210498, GI 1832773, GI 6990020, GI 4758118 (accession No. NP_004623), X83544, GI 7705841, GI 7705840, GI 5360131 (locus AF155118, accession No. AAD42884), AA114228, BE797255, BE242821, AW229739, AW227145, AV149215, GI 7190927, GI 7468151, GI 5353348, GI 4607778, and GI 6960635.

As used herein, the terms "label" and "indicating means" in their various grammatical forms refer to single atoms and molecules that are either directly or indirectly involved in the production of a detectable signal. Any label or indicating means can be linked to invention nucleic acid probes, expressed proteins, polypeptide fragments, or antibody molecules. These atoms or molecules can be used alone or in conjunction with additional reagents. Such labels are themselves well-known in clinical diagnostic chemistry.

The labeling means can be a fluorescent labeling agent that chemically binds to antibodies or antigens without denaturation to form a fluorochrome (dye) that is a useful immunofluorescent tracer. A description of immunofluorescent analytic techniques is found in DeLuca, "Immunofluorescence Analysis", in *Antibody As a Tool,* Marchalonis et al., eds., John Wiley & Sons, Ltd., pp. 189–231 (1982), which is incorporated herein by reference.

In one embodiment, the indicating group is an enzyme, such as horseradish peroxidase (HRP), glucose oxidase, and the like. In another embodiment, radioactive elements are employed as labeling agents. The linking of a label to a substrate, i.e., labeling of nucleic acid probes, antibodies, polypeptides, and proteins, is well known in the art. Detectable labels can be incorporated by chemical synthesis, chemical modification, in vitro enzymatic incorporation, or in vivo metabolic labeling. For instance, an invention antibody can be labeled by metabolic incorporation of radiolabeled amino acids provided in the culture medium. See, for example, Galfre et al., *Meth. Enzymol.,* 73:3–46 (1981). Conventional means of protein conjugation or coupling by activated functional groups are particularly applicable. See, for example, Aurameas et al., *Scand. J. Immunol.,* Vol. 8, Suppl. 7:7–23 (1978), Rodwell et al., *Biotech.,* 3:889–894 (1984), and U.S. Pat. No. 4,493,795.

In another embodiment of the invention, nucleic acids are provided encoding chimeric proteins comprising an invention DD, DED, or NB-ARC domain or fragment thereof, having the sequence of SEQ ID NOS:2, 4, 6, 8, 10, 12, 53, 56 or 58, and further comprising one or more sequences from a heterologous protein. Functional fragments of DD, DED or NB-ARC include, for example, polypeptides having the sequence SEQ ID NO:2, 4, 6, 8, 10, 12, 53, 56 or 58. Nucleic acids encoding proteins with which the DD, DED or NB-ARC domain, or functional fragment thereof, are fused will also encode, for example, glutathione-S-transferase, an antibody, or other proteins or functional fragments thereof which facilitate recovery of the chimera. Nucleic acids of the invention can also encode proteins with which the DD, DED, or NB-ARC domain, or functional fragment thereof, are fused, for example, to luciferase, green fluorescent protein, an antibody, or other proteins or functional fragments thereof which facilitate identification of the chimera. Still further nucleic acids of the invention encode proteins with which the DD, DED or NB-ARC domain or functional fragment thereof are fused including, for example, the LexA DNA binding domain, ricin, α-sarcin, an antibody, or other proteins which have therapeutic properties or other biological activity.

The present invention also provides compositions containing an acceptable carrier and any of an isolated, purified DD-, DED- or NB-ARC-containing protein or functional polypeptide fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil/water or water/oil emulsion, and various types of wetting agents.

The DD, DED or NB-ARC compositions described herein can be used, for example, in methods for modulating the activity of members of the apoptotic pathway. Thus it is within the scope of the present invention that a protein comprising the sequence SEQ ID NOS:2, 4, 6, 8, 10, 12, 53, 56 or 58 or a nucleic acid encoding a protein comprising the sequence SEQ ID NOS:1, 3, 5, 7, 9, 11 or 52, modulates the activity of member of an apoptotic pathway.

In one embodiment, modulation of a member of FADD, caspases such as caspase-8 and caspase-10, DR4, DR5, Traf6, hToll, MyD88, Fas, Raidd, IRAK, IRAK-2, IRAK-M, p75NTR, Tradd, DAP kinase, RIP, NMP84, ankyrins, Flip, PEA15, Flash, BAP31, BAR, DEDT/DEDD, and DAP3 or a related polypeptide that binds an invention DD, DED or NB-ARC will comprise the step of contacting a member of FADD, caspases such as caspase-8 and caspase-10, DR4, DR5, Traf6, hToll, MyD88, Fas, Raidd, IRAK, IRAK-2, IRAK-M, p75NTR, Tradd, DAP kinase, RIP, NMP84, ankyrins, Flip, PEA15, Flash, BAP31, BAR, DEDT/DEDD, and DAP3 with a protein comprising the sequence SEQ ID NOS:2, 4, 6, 8, 10, 12, 16, 18, 20, 22, 26, 53, 56 or 58. Preferably, the method comprises contacting a cell with a protein comprising the sequence of SEQ ID NOS:2, 4, 6, 8, 10, 12, 53, 56 or 58.

In another embodiment, modulation of a member of FADD, caspases such as caspase-8 and caspase-10, DR4, DR5, Traf6, hToll, MyD88, Fas, Raidd, IRAK, IRAK-2, IRAK-M, p75NTR, Tradd, DAP kinase, RIP, NMP84, ankyrins, Flip, PEA15, Flash, BAP31, BAR, DEDT/DEDD, and DAP3, or a related polypeptide that binds an invention DD, DED, or NB-ARC will comprise the step of contacting a member of FADD, caspases such as caspase-8 and caspase-10, DR4, DR5, Traf6, hToll, MyD88, Fas, Raidd, IRAK, IRAK-2, IRAK-M, p75NTR, Tradd, DAP kinase, RIP, NMP84, ankyrins, Flip, PEA15, Flash, BAP31, BAR, DEDT/DEDD, and DAP3 or a related polypeptide that binds an invention DD, DED or NB-ARC domain, with a nucleic acid encoding a protein comprising the sequence SEQ ID NOS:2, 4, 6, 8, 10, 12, 16, 18, 20, 22, 26, 53, 56 or 58. Preferably, the method comprises contacting a cell with a nucleic acid encoding a protein comprising the sequence of SEQ ID NOS:2, 4, 6, 8, 10, 12, 16, 18, 20, 22, 26, 53, 56 or 58.

In another embodiment, the DD, DED or NB-ARC domain compositions described herein can be used, for example, in methods for modulating the activity of proteins containing domains that bind invention DDs, DEDs or NB-ARC domains. Thus, it is within the scope of the present invention that a protein comprising the sequence SEQ ID NOS:2, 4, 6, 8, 10, 12, 16, 18, 20, 22, 26, 53, 56 or 58, or a nucleic acid encoding a protein comprising the sequence SEQ ID NOS:2, 4, 6, 8, 10, 12, 16, 18, 20, 22, 26, 53, 56 or 58, modulates the activity of one or more proteins containing domains that bind invention DDs, DEDs or NB-ARC domains.

In one embodiment, modulation of a protein containing a domain that interacts with an invention DD, DED or NB-ARC domain will comprise the step of contacting a protein containing a domain that interacts with an invention DD, DED or NB-ARC domain with a protein comprising the sequence SEQ ID NOS:2, 4, 6, 8, 10, 12, 16, 18, 20, 22, 26, 53, 56 or 58. Preferably, the method comprises contacting a cell with a protein comprising the sequence of SEQ ID NOS:2, 4, 6, 8, 10, 12, 16, 18, 20, 22, 26, 53, 56 or 58.

In another embodiment, modulation of a protein containing a domain that interacts with an invention DD, DED or NB-ARC will comprise the step of contacting a protein containing a domain that interacts with an invention DD, DED or NB-ARC with a nucleic acid encoding a protein comprising the sequence SEQ ID NOS:2, 4, 6, 8, 10, 12, 16, 18, 20, 22, 26, 53, 56 or 58. Preferably, the method comprises contacting a cell with a nucleic acid encoding a protein comprising the sequence of SEQ ID NOS:2, 4, 6, 8, 10, 12, 16, 18, 20, 22, 26, 53, 56 or 58.

In another embodiment, a DD, DED or NB-ARC domain comprising the sequence SEQ ID NOS:2, 4, 6, 8, 10, 12, 16, 18, 20, 22, 26, 53, 56 or 58, or a nucleic acid encoding a protein comprising the sequence SEQ ID NOS:2, 4, 6, 8, 10, 12, 16, 18, 20, 22, 26, 53, 56 or 58, modulates the activity of one or more associated proteins. Thus it is within the scope of the invention that an invention DD, DED or NB-ARC domain protein can modulate the activity of any protein with which the DD, DED or NB-ARC domain proteins are known to interact.

In one embodiment, modulation of a protein that binds an invention DD, DED or NB-ARC domain will comprise the step of contacting a with a protein comprising the sequence SEQ ID NOS:2, 4, 6, 8, 10, 12, 16, 18, 20, 22, 26, 53, 56 or 58. Preferably, the method comprises contacting a cell with a protein comprising the sequence of SEQ ID NOS:2, 4, 6, 8 10, 12, 16, 18, 20, 22, 26, 53, 56 or 58.

In another embodiment, modulation of a protein that interacts with an invention DD, DED or NB-ARC will comprise the step of contacting a protein that interacts with an invention DD, DED or NB-ARC with a nucleic acid encoding a protein comprising the sequence SEQ ID NOS:2, 4, 6, 8, 10, 12, 16, 18, 20, 22, 26, 53, 56 or 58. Preferably, the method comprises contacting a cell with a nucleic acid encoding a protein comprising the sequence of SEQ ID NOS:2, 4, 6, 8, 10, 12, 16, 18, 20, 22, 26, 53, 56 or 58.

DD or NB-ARC domain compositions can also be used, for example, in methods for modulating the activity of NF-κB or JNK. Proteins homologous to invention DD or NB-ARC domain, for example, the DD of IRAK4 (SEQ ID NO:6) is shown herein to modulate NF-κB activity. An invention NB-ARC domain, for example, the NB-ARC domain of DAP3, is expected to modulated NFκB activity based on previously known regulation of NFκB by the NB-ARC protein Nod1/CARD4. Thus, in accordance with another embodiment of the invention, a protein comprising the sequence SEQ ID NOS:2, 4, 6, 10, 12, 53, 56 or 58, or a nucleic acid encoding a protein comprising the sequence SEQ ID NOS:2, 4, 6, 10, 12, 53, 56 or 58, modulates the activity of NF-κB or JNK.

In one embodiment, modulation of NF-κB or JNK activity activity will comprise the step of contacting a cell containing NF-κB activity with a protein comprising the sequence SEQ ID NO:2, 4, 6, 10, 12, 53, 56 or 58. Preferably, the method comprises contacting a cell with a protein comprising the sequence of SEQ ID NO:2, 4, 6, 10, 12, 53, 56 or 58.

In another embodiment, modulation of NF-κB or JNK activity will comprise the step of contacting a cell containing NF-κB activity or JNK activity with a nucleic acid encoding a protein comprising the sequence SEQ ID NO:2, 4, 6, 10, 12, 53, 56 or 58. Preferably, the method comprises contacting a cell with a nucleic acid encoding a protein comprising the sequence of SEQ ID NO:2, 4, 6, 10, 12, 53, 56 or 58.

As disclosed herein, the N-terminal domain of DAP3 binds caspase-8, and DAP3 increases caspase-8 protease activity. Therefore, in another embodiment, modulation of caspase-8 activity comprises the step of contacting a cell containing caspase-8 activity with a nucleic acid encoding a protein comprising the NB-ARC domain (SEQ ID NO:4) of DAP3, or an invention DD- or DED-containing polypeptide.

The functions of the invention DDs, DEDs and NB-ARC domains support the role of DD, DED and NB-ARC domain containing polypeptides in modulating cellular pathways that effect apoptosis, cell proliferation, cell adhesion, cell stress responses, responses to microbial infection, and B cell immunoglobulin class switching. Thus, in accordance with another embodiment of the invention, a protein comprising the sequence SEQ ID NOS:2, 4, 6, 8, 10, 12, 53, 56 or 58, or SEQ ID NOS:16, 18, 20, 22 or 26, or a nucleic acid encoding a protein comprising the sequence SEQ ID NOS:2, 4, 6, 8, 10, 12, 53, 56 or 58, or SEQ ID NOS:16, 18, 20, 22 or 26, modulates apoptosis, cell proliferation, cell adhesion, cell stress responses, responses to microbial infection, or B cell immunoglobulin class switching.

In one embodiment, modulation of apoptosis, cell proliferation, cell adhesion, cell stress responses, responses to microbial infection, or B cell immunoglobulin class switching will comprise the step of contacting a cell with a protein comprising the sequence SEQ ID NOS:2, 4, 6, 8, 10, 12, 53, 56 or 58, or SEQ ID NOS:16, 18, 20, 22 or 26, whereby apoptosis, cell proliferation, cell adhesion, cell stress responses, responses to microbial infection, or B cell immunoglobulin class switching is modulated. Preferably, the method comprises contacting a cell with a protein comprising the sequence of SEQ ID NOS:2, 4, 6, 8, 10, 12, 53, 56 or 58, or SEQ ID NOS:16, 18, 20, 22 or 26.

In another embodiment, modulation of apoptosis, cell proliferation, cell adhesion, cell stress responses, responses to microbial infection, or B cell immunoglobulin class switching will comprise the step of contacting a cell with a nucleic acid encoding a protein comprising the sequence SEQ ID NOS:2, 4, 6, 8, 10, 12, 53, 56 or 58, or SEQ ID NOS:16, 18, 20, 22 or 26, whereby apoptosis, cell proliferation, cell adhesion, cell stress responses, responses to microbial infection, or B cell immunoglobulin class switching is modulated. Preferably, the method comprises contacting a cell with a nucleic acid encoding a protein comprising the sequence of SEQ ID NO:2, 4, 6, 8, 10, 12, 53, 56 or 58, or SEQ ID NOS:16, 18, 20, 22 or 26.

Also provided are antisense-nucleic acids having a sequence capable of binding specifically with full-length or any portion of an mRNA that encodes DD, DED or NB-ARC domain polypeptides so as to prevent translation of the mRNA. The antisense-nucleic acid can have a sequence capable of binding specifically with any portion of the sequence of the cDNA encoding DD, DED or NB-ARC domain polypeptides. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense-nucleic acid is an antisense-nucleic acid comprising chemical analogs of nucleotides. Exemplary antisense molecules for the DED containing polypeptide DAP3 are described herein.

Compositions comprising an amount of the antisense-nucleic acid, described above, effective to reduce expression of DD, DED or NB-ARC domain polypeptides by passing through a cell membrane and binding specifically with mRNA encoding DD, DED or NB-ARC domain polypeptides so as to prevent translation and an acceptable hydrophobic carrier capable of passing through a cell membrane are also provided herein. Suitable hydrophobic carriers are described, for example, in U.S. Pat. Nos. 5,334,761; 4,889,953; 4,897,355, and the like. The acceptable hydrophobic carrier capable of passing through cell membranes may also comprise a structure which binds to a receptor specific for a selected cell type and is thereby taken up by cells of the selected cell type. The structure may be part of a protein known to bind to a cell-type specific receptor.

Antisense-nucleic acid compositions are useful to inhibit translation of mRNA encoding invention polypeptides. Synthetic oligonucleotides, or other antisense chemical structures are designed to bind to mRNA encoding DD, DED or NB-ARC domain polypeptides and inhibit translation of mRNA and are useful as compositions to inhibit expression of DD, DED or NB-ARC domain associated genes in a tissue sample or in a subject.

In accordance with another embodiment of the invention, kits for detecting mutations, duplications, deletions, rearrangements and aneuploidies in DD, DED or NB-ARC genes comprising at least one invention probe or antisense nucleotide.

The present invention provides means to modulate levels of expression of DD, DED or NB-ARC polypeptides by employing synthetic antisense-nucleic acid compositions (hereinafter SANC) which inhibit translation of mRNA encoding these polypeptides. Synthetic oligonucleotides, or other antisense-nucleic acid chemical structures designed to recognize and selectively bind to mRNA, are constructed to be complementary to full-length or portions of a DD, DED or NB-ARC domain coding strand, including nucleotide sequences set forth in SEQ ID NOS:1, 3, 5, 7, 9, 11, 17, 21 or 52. The SANC is designed to be stable in the blood stream for administration to a subject by injection, or in laboratory cell culture conditions. The SANC is designed to be capable of passing through the cell membrane in order to enter the cytoplasm of the cell by virtue of physical and chemical properties of the SANC which render it capable of passing through cell membranes, for example, by designing small, hydrophobic SANC chemical structures, or by virtue of specific transport systems in the cell which recognize and transport the SANC into the cell. In addition, the SANC can be designed for administration only to certain selected cell populations by targeting the SANC to be recognized by specific cellular uptake mechanisms which bind and take up the SANC only within select cell populations. In a particular embodiment the SANC is an antisense oligonucleotide.

For example, the SANC may be designed to bind to a receptor found only in a certain cell type, as discussed supra. The SANC is also designed to recognize and selectively bind to target mRNA sequence, which may correspond to a sequence contained within the sequences shown in SEQ ID NOS:1, 3, 5, 7, 9, 11, 17, 21 or 52. The SANC is designed to inactivate target mRNA sequence by either binding thereto and inducing degradation of the mRNA by, for example, RNase I digestion, or inhibiting translation of mRNA target sequence by interfering with the binding of translation-regulating factors or ribosomes, or inclusion of other chemical structures, such as ribozyme sequences or reactive chemical groups which either degrade or chemically modify the target mRNA. SANCs have been shown to be capable of such properties when directed against mRNA targets (see Cohen et al., *TIPS*, 10:435 (1989) and Weintraub, *Sci. American*, January (1990), pp.40; both incorporated herein by reference).

In accordance with yet another embodiment of the present invention, there is provided a method for the recombinant production of invention DDs, DEDs or NB-ARC domains by expressing the above-described nucleic acid sequences in suitable host cells. Recombinant DNA expression systems that are suitable to produce DDs, DEDs or NB-ARC domains described herein are well-known in the art. For example, the above-described nucleotide sequences can be incorporated into vectors for further manipulation. As used herein, vector (or plasmid) refers to discrete elements that are used to introduce heterologous DNA into cells for either expression or replication thereof.

Suitable expression vectors are well-known in the art, and include vectors capable of expressing DNA operatively linked to a regulatory sequence, such as a promoter region that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors are well known to those of skill in the art and include those that are replicable in eukaryotic cells and/or prokaryotic cells and those that remain episomal or those which integrate into the host cell genome.

As used herein, a promoter region refers to a segment of DNA that controls transcription of DNA to which it is operatively linked. The promoter region includes specific sequences that are sufficient for RNA polymerase recognition, binding and transcription initiation. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector nucleotide sequences, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA.

As used herein, expression refers to the process by which polynucleic acids are transcribed into mRNA and translated into peptides, polypeptides, or proteins. If the polynucleic acid is derived from genomic DNA, expression can, if an appropriate eukaryotic host cell or organism is selected, include splicing of the mRNA.

Prokaryotic transformation vectors are well-known in the art and include pBlueskript and phage Lambda ZAP vectors (Stratagene, La Jolla, Calif.), and the like. Other suitable vectors and promoters are disclosed in detail in U.S. Pat. No. 4,798,885, issued Jan. 17, 1989, the disclosure of which is incorporated herein by reference in its entirety.

Other suitable vectors for transformation of E. coli cells include the pET expression vectors (Novagen, see U.S Pat. No. 4,952,496), e.g., pET11a, which contains the T7 promoter, T7 terminator, the inducible E. coli lac operator, and the lac repressor gene; and pET 12a–c, which contain the T7 promoter, T7 terminator, and the E. coli ompT secretion signal. Another suitable vector is the pIN-IIIompA2 (see Duffaud et al., *Meth. in Enzymology*, 153:492–507, 1987), which contains the lpp promoter, the lacUV5 promoter operator, the ompA secretion signal, and the lac repressor gene.

Exemplary, eukaryotic transformation vectors, include the cloned bovine papilloma virus genome, the cloned genomes of the murine retroviruses, and eukaryotic cassettes, such as the pSV-2 gpt system (described by Mulligan and Berg, *Nature Vol.* 277:108–114 (1979)] the Okayama-Berg cloning system (*Mol. Cell Biol.* 2:161–170 (1982)), and the expression cloning vector described by Genetics Institute (Wong et al., *Science* 228:810–815 (1985)), are available which provide substantial assurance of at least some expression of the protein of interest in the transformed eukaryotic cell line.

Particularly preferred base vectors which contain regulatory elements that can be linked to the invention DD-, DED- or NB-ARC domain-encoding DNAs for transfection of mammalian cells are cytomegalovirus (CMV) promoter-based vectors such as pcDNA1 (Invitrogen, San Diego, Calif.), MMTV promoter-based vectors such as pMAMNeo (Clontech, Palo Alto, Calif.) and pMSG (Pharmacia, Piscataway, N.J.), and SV40 promoter-based vectors such as pSVβ (Clontech, Palo Alto, Calif.).

In accordance with another embodiment of the present invention, there are provided "recombinant cells" containing the nucleic acid molecules (i.e., DNA or mRNA) of the present invention. Methods of transforming suitable host cells, preferably bacterial cells, and more preferably E. coli cells, as well as methods applicable for culturing said cells containing a gene encoding a heterologous protein, are generally known in the art. See, for example, Sambrook et al., *Molecular Cloning: A Laboratory Manual* (2 ed.), Cold Spring Harbor Laboratory Press, Cold Spring Harbor, N.Y., USA (1989).

Exemplary methods of transformation include, e.g., transformation employing plasmids, viral, or bacterial phage vectors, transfection, electroporation, lipofection, and the like. The heterologous DNA can optionally include sequences which allow for its extrachromosomal maintenance, or said heterologous DNA can be caused to integrate into the genome of the host (as an alternative means to ensure stable maintenance in the host).

Host organisms contemplated for use in the practice of the present invention include those organisms in which recombinant production of heterologous proteins has been carried out. Examples of such host organisms include bacteria (e.g., E. coli), yeast (e.g., *Saccharomyces cerevisiae, Candida tropicalis, Hansenula polymorpha* and *P. pastoris;* see, e.g., U.S. Pat. Nos. 4,882,279, 4,837,148, 4,929,555 and 4,855,231), mammalian cells (e.g., HEK293, CHO and Ltk$^-$ cells), insect cells, and the like. Presently preferred host organisms are bacteria. The most preferred bacteria is E. coli.

In one embodiment, nucleic acids encoding the invention DDs, DEDs or NB-ARC domains can be delivered into mammalian cells, either in vivo or in vitro using suitable viral vectors well-known in the art. Suitable retroviral vectors, designed specifically for "gene therapy" methods, are described, for example, in WIPO publications WO 9205266 and WO 9214829, which provide a description of methods for efficiently introducing nucleic acids into human cells. In addition, where it is desirable to limit or reduce the in vivo expression of the invention DD-, DED- or NB-ARC domain-containing, the introduction of the antisense strand of the invention nucleic acid is contemplated.

Viral based systems provide the advantage of being able to introduce relatively high levels of the heterologous nucleic acid into a variety of cells. Suitable viral vectors for introducing invention nucleic acid encoding an DD, DED or NB-ARC domain into mammalian cells (e.g., vascular tissue segments) are well known in the art. These viral vectors include, for example, Herpes simplex virus vectors (e.g., Geller et al., *Science,* 241:1667–1669 (1988)), Vaccinia virus vectors (e.g., Piccini et al., *Meth. in Enzymology,* 153:545–563 (1987); Cytomegalovirus vectors (Mocarski et al., in *Viral Vectors,* Y. Gluzman and S. H. Hughes, Eds., Cold Spring Harbor Laboratory, Cold Spring Harbor, N.Y., 1988, pp. 78–84), Moloney murine leukemia virus vectors (Danos et al., *PNAS, USA,* 85:6469 (1980)), adenovirus vectors (e.g., Logan et al., *PNAS, USA,* 81:3655–3659 (1984); Jones et al., *Cell,* 17:683–689 (1979); Berkner, *Biotechniques,* 6:616–626 (1988); Cotten et al., *PNAS, USA,* 89:6094–6098 (1992); Graham et al., *Meth. Mol. Biol.,* 7:109–127 (1991)), adeno-associated virus vectors, retrovirus vectors (see, e.g., U.S. Pat. Nos. 4,405,712 and 4,650,764), and the like. Especially preferred viral vectors are the adenovirus and retroviral vectors.

For example, in one embodiment of the present invention, adenovirus-transferrin/polylysine-DNA (TfAdpl-DNA) vector complexes (Wagner et al., *PNAS, USA,* 89:6099–6103 (1992); Curiel et al., *Hum. Gene Ther.,* 3:147–154 (1992); Gao et al., *Hum. Gene Ther.,* 4:14–24 (1993)) are employed to transduce mammalian cells with heterologous DD, DED or NB-ARC domain nucleic acid. Any of the plasmid expression vectors described herein may be employed in a TfAdpl-DNA complex.

As used herein, "retroviral vector" refers to the well-known gene transfer plasmids that have an expression cassette encoding an heterologous gene residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764).

Suitable retroviral vectors for use herein are described, for example, in U.S. Pat. No. 5,252,479, and in WIPO publications WO 92/07573, WO 90/06997, WO 89/05345, WO 92/05266 and WO 92/14829, incorporated herein by reference, which provide a description of methods for efficiently introducing nucleic acids into human cells using such retroviral vectors. Other retroviral vectors include, for example, the mouse mammary tumor virus vectors (e.g., Shackleford et al., *PNAS, USA,* 85:9655–9659 (1988)), and the like.

In accordance with yet another embodiment of the present invention, there are provided anti-DD, anti-DED or anti-NB-ARC domain antibodies having specific reactivity with one or more DD, DED or NB-ARC polypeptides of the present invention. Active fragments of antibodies are encompassed within the definition of "antibody". Invention antibodies can be produced by methods known in the art using invention polypeptides, proteins or portions thereof as antigens. For example, polyclonal and monoclonal antibodies can be produced by methods well known in the art, as described, for example, in Harlow and Lane, *Antibodies: A Laboratory Manual* (Cold Spring Harbor Laboratory (1988)), which is incorporated herein by reference. Invention polypeptides can be used as immunogens in generating such antibodies. Alternatively, synthetic peptides can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (see, for example, Bahouth et al., *Trends Pharmacol. Sci.* 12:338 (1991); Ausubel et al., *Current Protocols in Molecular Biology* (Supplement 47), John Wiley & Sons, New York (1999), which are incorporated herein by reference).

The invention provides isolated anti-DD, anti-DED, or anti-NB-ARC antibodies having specific reactivity with a polypeptide of SEQ ID NOS: 2, 4, 6, 8, 10, 12, 53, 56, or 58. In addition, isolated anti-DD, anti-DED, or anti-NB-ARC antibodies are provided having specific reactivity with a polypeptide of SEQ ID NOS: 18 or 22. Furthermore, isolated anti-DD, anti-DED, or anti-NB-ARC antibodies are provided having specific reactivity with amino acids or peptides within the polypeptides of SEQ ID NOS: 16, 20, and 26 that differ from SEQ ID NOS: 24 and 28. Invention polypeptides, or fragments thereof, and synthetic peptides can be used as immunogens in generating the antibodies provided herein.

Antibody so produced can be used, inter alia, in diagnostic methods and systems to detect the level of DD, DED or NB-ARC polypeptides present in a mammalian, preferably human, body sample, such as tissue or vascular fluid. Such antibodies can also be used for the immunoaffinity or affinity chromatography purification of the invention DD, DED or NB-ARC domain. In addition, methods are contemplated herein for detecting the presence of an invention DD, DED or NB-ARC domain either within a cell, or on the surface of a cell, comprising contacting the cell with an antibody that specifically binds to DD, DED or NB-ARC domain polypeptides, under conditions permitting binding of the antibody to the DD, DED or NB-ARC domain polypeptides, detecting the presence of the antibody bound to the DD, DED or NB-ARC domain polypeptide, and thereby detecting the presence of invention polypeptides on the surface of the cell. With respect to the detection of such polypeptides, the antibodies can be used for in vitro diagnostic or in vivo imaging methods.

Immunological procedures useful for in vitro detection of target DD, DED or NB-ARC domain polypeptides in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionucleotides, enzymes, fluorogens, chromogens and chemiluminescent labels.

Invention anti-DD, anti-DED or anti-NB-ARC domain antibodies are contemplated for use herein to modulate the activity of the DD, DED or NB-ARC domain polypeptide in living animals, in humans, or in biological tissues or fluids isolated therefrom. The term "modulate" refers to a compound's ability to increase (e.g., via an agonist), decrease (e.g., via an antagonist), or otherwise modify (e.g., increasing a first DD, DED or NB-ARC domain activity while decreasing a second DD, DED or NB-ARC domain activity) the biological activity of an invention DD, DED or NB-ARC domain protein, such as binding to FADD, caspases such as caspase-8, DR4, DR5, Traf6, hToll, MyD88 and Fas, NF-κB or JNK modulating activity, or caspase such as caspase-8 modulating activity, apoptosis modulating activity, cell proliferation modulating activity, cell adhesion modulating activity, cell stress responses modulating activity, microbial infection response modulating activity, or B cell immunoglobulin class switching modulating activity, and the like. Accordingly, compositions comprising a carrier and an amount of an antibody having specificity for DD, DED or NB-ARC domain polypeptides effective to block naturally occurring ligands or other DD-, DED- or NB-ARC domain-associated proteins, and the like, from binding to invention DD, DED or NB-ARC domain polypeptides are contemplated herein. For example, a monoclonal antibody directed to an epitope of an invention DD, DED or NB-ARC domain polypeptide including an amino acid sequence set forth in SEQ ID NOS:2, 4, 6, 8, 10, 12, 53, 56 or 58, or SEQ ID NOS:16, 18, 20, 22 or 26, can be useful for this purpose.

The present invention further provides transgenic non-human mammals that are capable of expressing exogenous nucleic acids encoding DDs, DEDs or NB-ARC domains. As employed herein, the phrase "exogenous nucleic acid" refers to nucleic acid sequence which is not native to the host, or which is present in the host in other than its native environment (e.g., as part of a genetically engineered DNA construct). In addition to naturally occurring levels of DD-, DED- or NB-ARC domain-containing proteins, invention DDs, DEDs or NB-ARC domain can either be overexpressed or underexpressed (such as in the well-known knock-out transgenics) in transgenic mammals.

Also provided are transgenic non-human mammals capable of expressing nucleic acids encoding DD, DED or NB-ARC domain polypeptides so mutated as to be incapable of normal activity, i.e., do not express native DD, DED or NB-ARC domain polypeptides. The present invention also provides transgenic non-human mammals having a genome comprising antisense nucleic acids complementary to nucleic acids encoding DD, DED or NB-ARC domain polypeptides, placed so as to be transcribed into antisense mRNA complementary to mRNA encoding DD, DED or NB-ARC domain polypeptides, which hybridizes to the mRNA and, thereby, reduces the translation thereof. The nucleic acid can additionally comprise an inducible promoter and/or tissue specific regulatory elements, so that expression can be induced, or restricted to specific cell types. Examples of nucleic acids are DNA or cDNA having a coding sequence the same or substantially the same as the coding sequence of SEQ ID NOS:13, 15, 17, 19, 21 or 54, and preferably 1, 3, 5, 7, 9, 11 or 52. An example of a non-human transgenic mammal is a transgenic mouse. Examples of tissue specificity-determining elements are the metallothionein promoter and the L7 promoter.

Animal model systems which elucidate the physiological and behavioral roles of DD, DED or NB-ARC domain polypeptides are also provided, and are produced by creating transgenic animals in which the expression of the DD, DED or NB-ARC domain polypeptide is altered using a variety of techniques. Examples of such techniques include the insertion of normal or mutant versions of nucleic acids encoding a DD, DED or NB-ARC domain polypeptide by microinjection, retroviral infection or other means well known to those skilled in the art, into appropriate fertilized embryos to produce a transgenic animal. (See, for example, Hogan et al., *Manipulating the Mouse Embryo: A Laboratory Manual* (Cold Spring Harbor Laboratory, (1986)).

Also contemplated herein, is the use of homologous recombination of mutant or normal versions of DD, DED or NB-ARC domain genes with the native gene locus in transgenic animals, to alter the regulation of expression or the structure of DD, DED or NB-ARC domain polypeptides (see, Capecchi et al., *Science* 244:1288 (1989); Zimmer et al., *Nature* 338:150 (1989); which are incorporated herein by reference). Homologous recombination techniques are well known in the art. Homologous recombination replaces the native (endogenous) gene with a recombinant or mutated gene to produce an animal that cannot express native (endogenous) protein but can express, for example, a mutated protein which results in altered expression of DD, DED or NB-ARC domain polypeptides.

In contrast to homologous recombination, microinjection adds genes to the host genome, without removing host genes. Microinjection can produce a transgenic animal that is capable of expressing both endogenous and exogenous DDs, DEDs or NB-ARC domains. Inducible promoters can be linked to the coding region of nucleic acids to provide a means to regulate expression of the transgene. Tissue specific regulatory elements can be linked to the coding region to permit tissue-specific expression of the transgene. Transgenic animal model systems are useful for in vivo screening of compounds for identification of specific ligands, i.e., agonists and antagonists, which activate or inhibit protein responses.

Invention nucleic acids, oligonucleotides (including antisense), vectors containing same, transformed host cells, polypeptides and combinations thereof, as well as antibodies of the present invention, can be used to screen compounds in vitro to determine whether a compound functions as a potential agonist or antagonist to invention DDs, DEDs or NB-ARC domains. These in vitro screening assays provide information regarding the function and activity of invention DDs, DEDs, or NB-ARC domains which can lead to the identification and design of compounds that are capable of specific interaction with one or more types of polypeptides, peptides or proteins.

By the known homology of invention DDs, DEDs and NB-ARC domains to known proteins containing these domains, it is within the scope of the invention that invention DD, DED or NB-ARC domain also have a role in cellular pathways that effect apoptosis, cell proliferation, cell adhesion, cell stress responses, responses to microbial infection, and B cell immunoglobulin class switching. Thus, invention DDs, DEDs or NB-ARC domains also provide drug discovery targets for a broad variety of pathologies including infection, autoimmunity, inflammation, allergy, allograph-rejection and sepsis, and for a broad variety of cancer pathologies, such as, gliomas, carcinomas, sarcomas, melanomas, hamartomas and the like. In certain aspects of the invention, invention DD, DED or NB-ARC domain proteins, agonist or antagonists thereto, are used to treat infection, autoimmunity, inflammation, allergy, allograph-rejection, sepsis, keratinocyte hyperplasia, neoplasia, keloid, benign prostatic hypertrophy, inflammatory hyperplasia, fibrosis, smooth muscle cell proliferation in arteries following balloon angioplasty (restenosis), and the like. Exemplary cancer pathologies contemplated herein for treatment include, gliomas, carcinomas, adenocarcinomas, sarcomas, melanomas, hamartomas, leukemias, lymphomas, and the like. Exemplary infections contemplated herein for treatment include bacterial infections such as infections caused by *Chlamydia* (Ojcius et al., *J. Immunol.* 161:4220–6 (1998)), *Pseudomonas* (Hauser and Engel, *Infect. Immun.* 67: 5530–7 (1999)), *Salmonella* (Hersh et al., *Proc. Natl. Acad. Sci, USA,* 96:2396–401 (1999)), *Shigella* (Zychlinsky, et al., *Nature* 358:167–9 (1992)), and *Mycobacterium* (Oddo, et al., *J. Immunol.* 160:5448–54 (1998)), which are incorporated herein by reference.

*Chlamydia trachomatis* is a eubacterial pathogen accounting for the major cause of blindness in Asia and Africa and is the most common sexually transmitted disease in the United States. *Chlamydia* infections have been linked to pelvic inflammatory disease, urethritis, and infertility. Different strains of *Chlamydia* have also been linked to arthritis, pneumonia, upper respiratory and ear infections, asthma, vasculitis, atherosclerosis, and other vascular diseases. In addition, chronic *Chlamydia* infections have also been linked to cancer. A recent longitudinal study provided evidence that patients infected with *Chlamydia trachomatis* serotype G carry a 6.6-fold increased risk of developing cervical cancer.

Also provided herein are methods of treating pathologies, said method comprising administering an effective amount of an invention therapeutic composition. Such compositions are typically administered in a physiologically compatible composition.

Methods of treating pathologies of abnormal cell proliferation include methods of modulating the activity of one or more oncogenic proteins, wherein the oncogenic proteins specifically interact with a DD, DED or NB-ARC domain. Methods of modulating the activity of such oncogenic proteins include contacting the oncogenic protein with a substantially pure DD, DED or NB-ARC domain or an active fragment (i.e., oncogenic protein-binding fragment) thereof. This contacting can modulate the activity of the oncogenic protein, thereby providing a method of treating a pathology caused by the oncogenic protein. Further methods of modulating the activity of oncogenic proteins include contacting the oncogenic protein with an agent, wherein the agent modulates the interactions between the DD, DED or NB-ARC domain and the oncogenic protein.

Methods of treating bacterial infections include methods of modulating the activity of one or more bacterial proteins that contain or specifically interact with a DD, DED or NB-ARC domain. Methods of modulating the activity of such a bacterial protein include contacting the bacterial protein with a substantially pure DD, DED or NB-ARC domain or an active fragment thereof. This contacting can modulate the activity of the bacterial protein, thereby providing a method of treating a pathology caused by the bacteria. Further methods of modulating the activity of bacterial proteins include contacting the bacterial protein with an agent, including, for example, a nucleic acid, a drug, a peptide, or a protein, including a secreted protein or an antibody, wherein the agent modulates a DD, DED or NB-ARC domain of a bacterial protein or the agent modulates the interactions between a DD, DED or NB-ARC domain and a bacterial protein.

Methods of treating bacterial infections can further include methods of modulating the activity of one or more host cell proteins that specifically interact with a bacterial protein that contains or specifically interacts with a DD, DED or NB-ARC domain. Methods of modulating the activity of such a host cell protein include contacting the host cell protein with a substantially pure DD, DED or NB-ARC domain or an active fragment thereof. This contacting can modulate the activity of the host cell protein, thereby providing a method of treating a pathology caused by the interaction of the host cell and bacterial proteins. Further methods of modulating the activity of host cell proteins include contacting the host cell protein with an agent, wherein the agent modulates the interactions between a host cell protein and a bacterial protein that contains or specifically interacts with a DD, DED or NB-ARC domain. All of the above methods for treating bacterial infections can be used alone or in combination with other methods of treating bacterial infections.

Methods of treating immune-based pathologies such as infection, autoimmunity, inflammation, allergy, allograft-rejection, and sepsis will include modulating the activity of one or more proteins that modulate immune response, wherein the protein that modulates immune response specifically interact with a DD, DED or NB-ARC domain. Methods of modulating the activity of such protein that modulates immune response will include contacting the protein that modulates immune response with a substantially pure DD, DED or NB-ARC domain or an active fragment (i.e., protein-binding fragment) thereof. This contacting will modulate the activity of the protein that modulates immune response, thereby providing a method of treating a pathology caused by the protein that modulates immune response. Further methods of modulating the activity of a protein that modulates immune response will include contacting the protein that modulates immune response with an agent, wherein the agent modulates the interactions between the DD, DED or NB-ARC domain and the protein that modulates immune response.

Also contemplated herein, are therapeutic methods using invention pharmaceutical compositions for the treatment of pathological disorders in which there is too little cell division, such as, for example, bone marrow aplasias, immunodeficiencies due to a decreased number of lymphocytes, and the like. Methods of treating a variety of inflammatory diseases with invention therapeutic compositions are also contemplated herein, such as treatment of sepsis, fibrosis (e.g., scarring), arthritis, graft versus host disease, and the like. Therapeutic methods using invention polypeptides or nucleic acids are also contemplated for treating infectious diseases.

The present invention also provides therapeutic compositions useful for practicing the therapeutic methods described herein. Therapeutic compositions of the present invention, such as pharmaceutical compositions, contain a physiologically compatible carrier together with an invention DD, DED or NB-ARC domain (or functional fragment thereof), a DD, DED or NB-ARC domain modulating agent, such as a compound (agonist or antagonist) identified by the methods described herein, or an anti-DD, anti-DED or anti-NB-ARC domain antibody, as described herein, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically compatible" and grammatical variations thereof, as they refer to compositions, carriers, diluents and reagents, are used interchangeably and represent that the materials are capable of administration to a mammal without the production of undesirable physiological effects such as nausea, dizziness, gastric upset, and the like.

The preparation of a pharmacological composition that contains active ingredients dissolved or dispersed therein is well known in the art. Typically such compositions are prepared as injectables either as liquid solutions or suspensions; however, solid forms suitable for solution, or suspension, in liquid prior to use can also be prepared. The preparation can also be emulsified.

The active ingredient can be mixed with excipients which are pharmaceutically acceptable and compatible with the active ingredient in amounts suitable for use in the therapeutic methods described herein. Suitable excipients are, for example, water, saline, dextrose, glycerol, ethanol, or the like, as well as combinations of any two or more thereof. In addition, if desired, the composition can contain minor amounts of auxiliary substances such as wetting or emulsifying agents, pH buffering agents, and the like, which enhance the effectiveness of the active ingredient.

The therapeutic composition of the present invention can include pharmaceutically acceptable salts of the components therein. Pharmaceutically acceptable nontoxic salts include the acid addition salts (formed with the free amino groups of the polypeptide) that are formed with inorganic acids such as, for example, hydrochloric acid, hydrobromic acid, perchloric acid, nitric acid, thiocyanic acid, sulfuric acid, phosphoric acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, and the like.

Salts formed with the free carboxyl groups can also be derived from inorganic bases such as, for example, sodium hydroxide, ammonium hydroxide, potassium hydroxide, and the like; and organic bases such as mono-, di-, and tri-alkyl and -aryl amines (e.g., triethylamine, diisopropyl amine, methyl amine, dimethyl amine, and the like) and optionally substituted ethanolamines (e.g., ethanolamine, diethanolamine, and the like).

Physiologically tolerable carriers are well known in the art. Exemplary liquid carriers are sterile aqueous solutions that contain no materials in addition to the active ingredients and water, or contain a buffer such as sodium phosphate at physiological pH, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary additional liquid phases include glycerin, vegetable oils such as cottonseed oil, and water-oil emulsions.

As described herein, an "effective amount" is a predetermined amount calculated to achieve the desired therapeutic effect, e.g., to modulate activity of an invention DD, DED or NB-ARC domain. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such compounds in depot or long-lasting form as discussed hereinafter. A therapeutically effective amount is typically an amount of an DD-, DED- or NB-ARC domain-modulating agent or compound identified herein that, when administered in a physiologically acceptable composition, is sufficient to achieve a plasma concentration of from about 0.1 $\mu$g/ml to about 100 $\mu$g/ml, preferably from about 1.0 $\mu$g/ml to about 50 $\mu$g/ml, more preferably at least about 2 $\mu$g/ml and usually 5 to 10 $\mu$g/ml. Therapeutic invention anti-DD, anti-DED or anti-NB-ARC domain antibodies can be administered in proportionately appropriate amounts in accordance with known practices in this art.

In accordance with still another embodiment of the present invention, there are provided methods for identifying compounds which bind to DD, DED or NB-ARC domain polypeptides. The invention proteins may be employed in a competitive binding assay. Such an assay can accommodate the rapid screening of a large number of compounds to determine which compounds, if any, are capable of binding to DDs, DEDs or NB-ARC domains. Subsequently, more detailed assays can be carried out with those compounds found to bind, to further determine whether such compounds act as modulators, agonists or antagonists of invention DDs, DEDs or NB-ARC domains. Compounds that bind to and/or modulate invention DDs, DEDs or NB-ARC domains can be used to treat a variety of pathologies mediated by invention DDs, DEDs or NB-ARC domains.

In another embodiment of the invention, there is provided a bioassay for identifying compounds which modulate the activity of invention DD, DED or NB-ARC domain polypeptides. Invention DD, DED or NB-ARC domain polypeptides are known to influence the activities of, for example, NF-κB, JNK, and caspase-8. Thus a reporter gene construct to assay for NF-κB activity can be used to test invention DED activity (see Examples). According to this method, invention DD, DED or NB-ARC domain polypeptides are contacted with an "unknown" or test substance, the activity of the invention DD, DED or NB-ARC domain polypeptide is monitored subsequent to the contact with the "unknown" or test substance, and those substances which effect a resultant modulation of, for example, NF-κB or JNK activity or caspase, such as caspase-8, activity are identified as functional ligands for DD, DED or NB-ARC domain polypeptides.

Alternative bioassays for identifying compounds which modulate the activity of invention DD, DED or NB-ARC domain polypeptides can be used which routinely are used to test for protein:protein interactions. Such bioassays include yeast two-hybrid assays, glutathione-S-transferase fusion protein binding assays, co-immmunoprecipitation assays, and the like. Such assays are well known in the art and can be found in standard reference texts such as Sambrook et al., supra, and Ausubel et al., supra, 1999.

In accordance with another embodiment of the present invention, transformed host cells that recombinantly express invention polypeptides can be contacted with a test compound, and the modulating effect(s) thereof can then be evaluated by comparing the DD-, DED-, or NB-ARC domain-medicated response (e.g., via reporter gene expression) in the presence and absence of test compound, or by comparing the response of test cells or control cells (i.e., cells that do not express DD, DED or NB-ARC domain polypeptides), to the presence of the compound.

As used herein, a compound or a signal that "modulates the activity" of invention DD, DED or NB-ARC domain polypeptides refers to a compound or a signal that alters the activity of DD, DED or NB-ARC domain polypeptides so that the activity of the invention polypeptide is different in the presence of the compound or signal than in the absence of the compound or signal. In particular, such compounds or signals include agonists and antagonists. An agonist encompasses a compound or a signal that activates DD, DED or NB-ARC domain protein expression. Alternatively, an antagonist includes a compound or signal that interferes with DD, DED or NB-ARC domain expression. Typically, the effect of an antagonist is observed as a blocking of agonist-induced protein activation. Antagonists include competitive and non-competitive antagonists. A competitive antagonist (or competitive blocker) interacts with or near the site specific for agonist binding. A non-competitive antagonist or blocker inactivates the function of the polypeptide by interacting with a site other than the agonist interaction site.

As understood by those of skill in the art, assay methods for identifying compounds that modulate DD, DED or NB-ARC domain activity generally require comparison to a control. One type of a "control" is a cell or culture that is treated substantially the same as the test cell or test culture exposed to the compound, with the distinction that the "control" cell or culture is not exposed to the compound. For example, in methods that use voltage clamp electrophysiological procedures, the same cell can be tested in the presence or absence of compound, by merely changing the external solution bathing the cell. Another type of "control" cell or culture may be a cell or culture that is identical to the transfected cells, with the exception that the "control" cell or culture do not express native proteins. Accordingly, the response of the transfected cell to compound is compared to the response (or lack thereof) of the "control" cell or culture to the same compound under the same reaction conditions.

In yet another embodiment of the present invention, the activation of DD, DED or NB-ARC domain polypeptides can be modulated by contacting the polypeptides with an effective amount of at least one compound identified by the above-described bioassays.

In accordance with another embodiment of the present invention, there are provided methods for identifying a binding agent that binds a DD, DED or NB-ARC domain, where a DD, DED, or NB-ARC domain from DAP3, IRAK4, CTDD, DED4 or NIDD is contacted with a candidate binding agent and then the association of the domain and candidiate binding agent are detected. An association between the candidate binding agent and the domain identifies the candidate binding agent as a binding agent that binds a DD, DED, or NB-ARC domain from DAP3, IRAK4, CTDD, DED4 or NIDD. The association between the candidate binding agent and the domain can be detected using a variety of methods well known in the art, for example, co-immunoprecipitation assays and transcription based assays such as reporter assays and two-hybrid assays. Such assays are well known in the art and can be found in standard reference texts such as Sambrook et al., supra, and Ausubel et al., supra, 1999. Additional methods include, for example, scintillation proximity assay (SPA) (Alouani, *Methods Mol. Biol.* 138:135–41 (2000)), UV or chemical cross-linking (Fancy, *Curr. Olpin. Chem. Biol.* 4:28–33 (2000)), competition binding assays (Yamamura et al., *Methods in Neurotransmitter Receptor Analysis,* Raven Press, New York, 1990), biomolecular interaction analysis (BIA) (Weinberger et al., *Pharmacogenomics* 1:395–416 (2000)), mass spectrometry (MS) (McLafferty et al., *Science* 284:1289–1290 (1999) and Degterev, et al., *Nature Cell Bioloqy* 3:173–182 (2001)), nuclear magnetic resonance (NMR) (Shuker etal., *Science* 274:1531–1534 (1996), Hajduk et al., *J. Med. Chem.* 42:2315–2317 (1999), and Chen and Shapiro, *Anal. Chem.* 71:669A–675A (1999)), and fluorescence polarization assays (FPA) (Degterev et al., supra, 2001) which are incorporated herein by reference. The identified binding agent can be, for example, another protein, including an antibody or fragment thereof, or a drug or other agent.

In accordance with another embodiment of the present invention, there are provided methods for identifying an effective agent that modulates the association of a DD, DED or NB-ARC domain from DAP3, IRAK4, CTDD, DED4 or NIDD with a protein that binds the DD, DED or NB-ARC domain where the proteins are contacted under conditions that allow the domain and a protein that binds the domain to associate with an agent suspected of being able to modulate the association of the domain and protein that binds the domain. Detection of a modulated association of the domain and protein that binds the domain identifies the agent as an effective agent. An altered association can be detected, for example, by measuring the activity of NF-κB or caspases or by using other methods well known in the art and described herein. The effective agent can be, for example, another protein, including an antibody, or a drug.

In accordance with another embodiment of the present invention, there are provided methods of modulating a cell process such as apoptosis, cell proliferation, cell adhesion, cell stress responses, responses to microbial infection, and B cell immunoglobulin class switching, by contacting a cell with an effective agent that modulates the activity of a DD-, DED-, or NB-ARC domain. For example, a nucleic acid molecule encoding a DD, DED or NB-ARC domain from DAP3, IRAK4, CTDD, DED4 or NIDD, can be introduced into a cell and expression of the DD, DED or NB-ARC domain can modulate a cell process within the cell. In addition, an antisense nucleotide sequence that specifically hybridizes to a nucleic acid molecule encoding a DD, DED or NB-ARC domain from DAP3, IRAK4, CTDD, DED4 or NIDD, can be introduced into a cell where hybridization can reduce or inhibit the expression of the DD, DED or NB-ARC domain in the cell which modulates a cell process within the cell. Furthermore, a cell process can be modulated by contacting a cell with a DD, DED or NB-ARC domain or functional fragment thereof, an effective agent as described above, or an anti-DD, anti-DED or anti-NB-ARC domain antibody where the DD, DED, or NB-ARC domain is from DAP3, IRAK4, DED4 or NIDD.

Methods are also provided for modulating an activity mediated by a DD, DED or NB-ARC domain, by contacting the DD, DED or NB-ARC domain with an effective agent identified as described above. The modulated activity can be, for example, binding of a DD, DED or NB-ARC domain protein to a protein that binds a DD, DED or NB-ARC domain, NF-κB activity, caspase such as caspase-8 activity, apoptosis activity, cell proliferation activity, cell adhesion, cell stress response activity, responses to microbial infection activity, and B cell immunoglobulin class switching activity. For example, the activity of NF-κB or caspases can be modulated by a cell with an effective agent that modulates the activity of a DD-, DED-, or NB-ARC domain.

In accordance with another embodiment of the present invention, there are provided methods of diagnosing a pathology characterized by an increased or decreased level of a DD, DED or NB-ARC domain from DAP3, IRAK4, CTDD, DED4 or NIDD in a subject. For example, a test sample from a subject can be contacted with an agent that can bind the DD, DED or NB-ARC domain under suitable conditions, which allow specific binding of the agent to the DD, DED or NB-ARC domain, and then the amount of specific binding in the test sample can be compared with the amount of specific binding in a control sample, where an increased or decreased amount of specific binding in said test sample as compared to a control sample is diagnostic of a pathology. The agent that can bind the DD, DED or NB-ARC domain can be, for example, an anti-DD, anti-DED, or anti-NB-ARC domain antibody, FADD, caspases such as caspase-8 and caspase-10, DR4, DR5, Traf6, hToll, MyD88 Fas, Raidd, IRAK, IRAK-2, IRAK-M, p75NTR, Tradd, DAP kinase, RIP, NMP84, ankyrins, Flip, PEA15, Flash, BAP31, BAR, DEDT/DEDD, CTDD, or DAP3. In addition, a test sample containing nucleic acid molecules from a subject can be contacted under high stringency hybridization conditions with an oligonucleotide specific for one of the above DD, DED, or NB-ARC domain containing proteins, and the amount of specific binding in the test sample can be compared with the amount of specific binding in a control sample, where an increased or decreased amount of specific binding in the test sample as compared to said control sample is diagnostic of a pathology.

In accordance with another embodiment of the present invention, there are provided methods for diagnosing cancer, said method comprising detecting, in said subject, a defective sequence or mutant of SEQ ID NOS:1, 3, 5, 7, 9, 11, or 52.

In accordance with another embodiment of the present invention, there are provided methods for diagnosing a bacterial infection or monitoring the progression of a bacterial infection by detecting in a subject either nucleic acid molecules or proteins specific to a bacterial pathogen. For example, a *Chlamydia* infection can be detected by contacting a test sample from a subject with an antibody specifically reactive with a peptide or polypeptide consisting of any of SEQ ID NOS: 10, 20, 53, 56, or 58. In addition, a test sample from a subject can be contacted under high stringency conditions with a nucleic acid molecule encoding any of SEQ ID NOS: 10, 20, 53, 56, or 58.

In accordance with another embodiment of the present invention, there are provided diagnostic systems, preferably in kit form, comprising at least one invention nucleic acid in a suitable packaging material. The diagnostic nucleic acids are derived from the DD-, DED- or NB-ARC domain-encoding nucleic acids described herein. In one embodiment, for example, the diagnostic nucleic acids are derived from any of SEQ ID NOS:1, 3, 5, 7, 9, 11 or 52. Invention diagnostic systems are useful for assaying for the presence or absence of nucleic acid encoding DD, DED or NB-ARC domain polypeptides in either genomic DNA or in transcribed nucleic acid (such as mRNA or cDNA) encoding DD, DED or NB-ARC domain polypeptides.

A suitable diagnostic system includes at least one invention nucleic acid, preferably two or more invention nucleic acids, as a separately packaged chemical reagent(s) in an amount sufficient for at least one assay. Instructions for use of the packaged reagent are also typically included. Those of skill in the art can readily incorporate invention nucleic probes and/or primers into kit form in combination with appropriate buffers and solutions for the practice of the invention methods as described herein.

As employed herein, the phrase "packaging material" refers to one or more physical structures used to house the contents of the kit, such as invention nucleic acid probes or primers, and the like. The packaging material is constructed by well known methods, preferably to provide a sterile, contaminant-free environment. The packaging material has a label which indicates that the invention nucleic acids can be used for detecting a particular sequence encoding DD, DED or NB-ARC domain polypeptides including the nucleotide sequences set forth in SEQ ID NOS:1, 3, 5, 7, 9, 11 or 52 or mutations or deletions therein, thereby diagnosing the presence of, or a predisposition for, cancer. In addition, the packaging material contains instructions indicating how the materials within the kit are employed both to detect a particular sequence and diagnose the presence of, or a predisposition for, cancer.

The packaging materials employed herein in relation to diagnostic systems are those customarily utilized in nucleic acid-based diagnostic systems. As used herein, the term "package" refers to a solid matrix or material such as glass, plastic, paper, foil, and the like, capable of holding within fixed limits an isolated nucleic acid, oligonucleotide, or primer of the present invention. Thus, for example, a package can be a glass vial used to contain milligram quantities of a contemplated nucleic acid, oligonucleotide or primer, or it can be a microtiter plate well to which microgram quantities of a contemplated nucleic acid probe have been operatively affixed.

"Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

All U.S. patents and all publications mentioned herein are incorporated in their entirety by reference thereto. The invention will now be described in greater detail by reference to the following non-limiting examples.

EXAMPLES

I. Binding Activity of DAP3

FADD is an apoptosis-inducing adapter protein that uses its DD to bind the intracellular domain of Fas and its Death Effector Domain (DED) to bind corresponding DEDs in the N-terminal prodomain of pro-Caspase-8 (pro-Casp8) (Boldin et al., Cell 85:803–815 (1996); Muzio et al., Cell 85:817–827 (1996)). During two-hybrid screens of cDNA libraries using FADD as a bait, interactions were detected with DAP3, a protein previously implicated in death receptor-mediated apoptosis through unknown mechanisms (Kissil et al., EMBO J. 18:353–362 (1999)). The DAP3 protein contains a putative nucleotide-binding motif (P-loop) but has not been previously reported to contain other recognizable domains. The DAP3 nucleotide sequence is found at GenBank accession No. X83544 and is referenced herein as SEQ ID NO:13, the amino acid sequence (GI 4758118) is referenced as SEQ ID NO:14.

To test DAP3 binding, various DNA constructs were made. Wild-type and mutant cDNAs encoding full-length or fragments of human DAP3, FADD, or pro-Casp8 were engineered using PCR from the plasmids pcDNA3-hDAP3, pcDNA3-DAP3K134A, pcDNA3-Flag-FADD, pcDNA3-Flag-Mch5, pcDNA3-Flag-Mch5 (cys/ala) (Kissil et al., J. Biol. Chem. 270:27932–27936 (1995); Kissil et al., EMBO J. 18:353–362 (1999); Boldin et al., Cell 85:803–815 (1996); Muzio et al., Cell 85:817–827 (1996); Torii et al., EMBO J. 18:6037–6049 (1999)) and cloned into the EcoRI and XhoI sites of: (a) yeast two-hybrid vectors, pGilda and pJG4-5, which produce fusion proteins with a LexA DNA-binding domain or a B42 transactivation domain, respectively, at the N-terminus under the control of a GALL promoter (Estojak et al., Mol. Cell Biol. 15:5820 (1995)); (b) pcDNA3-Flag or pcDNA3-HA for mammalian expression (Takayama et al., EMBO J. 16:4887 (1997)); (c) pET21d-N-His$_6$ for bacterial expression; or (d) p426 for expression in yeast. The cDNAs encoding DR4, DR4(DDD), and wild-type DR5 were generated by PCR from pCR3.V64-Met-Flag-Trail-R1 and pCR3.V64-Met-Flag-Trail-R2 (Schneider, et al., FEBS Lett. 416:329 (1997)) and cloned into EcoRI and XhoI sites of pcDNA3 (Invitrogen; Carslbad Calif.).

Two-hybrid comparisons of DAP3 interactions with numerous other proteins was used to confirm the specificity of binding results with DAP3 (Table 1). For two-hybrid cDNA library screening and protein interaction assays, library screening by the yeast two-hybrid method was performed as described (Sato et al., Science 268:411 (1995); Matsuzawa et al., EMBO J. 17:2736 (1998)) using the pGilda plasmid encoding human FADD as a bait, a human Jurkat T-cell cDNA library (gift from Brian Seed (Massachusetts General Hospital, Harvard University) and the EGY48 strain Saccharomyces cerevisiae (MAT, trp1, ura3, his, leu2::plexApo6-leu2) (Estojak et al., Mol. Cell Biol. 15:5820 (1995)). Cells were grown in either YPD medium with 1% yeast extract, 2% polypeptone and 2% glucose, or in Burkholder's minimal medium (BMM) fortified with appropriate amino acids. Transformations were performed by a LiCl method using 0.1 mg of pJG4-5 cDNA library DNA and 5 mg denatured salmon sperm DNA. Clones that formed on Leu-deficient BMM plates containing 2% galactose or 1% raffinose were transferred to BMM plates containing leucine and 2% glucose, and filter assays were performed for β-galactosidase measurements as described (Sato et al., Proc Natl. Acad. Sci. USA 91:9238 (1994)). From an initial screen of ~2×10$^7$ transformants, 380 clones were identified which transactivated the LEU2 reporter gene based on ability to grow on leucine-deficient media after 4 days. Of those, 20 colonies were also positive for β-galactosidase, as tested by filter assays where color was scored after 1 hr. Two of these clones encoded DAP3 and two encoded FADD.

For most 2-hybrid assays, yeast strain EGY48 was transformed with yeast expression plasmids encoding various proteins expressed as fusions with either a N-terminal LexA DNA-binding domain encoded by pGilda plasmid or B42 transactivation domain encoded by pJG4-5 plasmid. Transformants were scored for activation of LEU2 and lacZ reporter genes under the control of LexA operators (Estojak et al., Mol. Cell Biol. 15:5820 (1995)). Plasmid combinations that resulted in growth on leucine-deficient media within 4 days were considered positive. β-galactosidase activity of each colony was also tested by filter assay, scoring color (blue/white) after 1 hr. For three-hybrid assays, in addition to pGilda and pJG4-5 plasmids, p426 plasmid was used for the expression of DAP3. Plasmid combinations that resulted in growth on leucine-deficient media within 10 days were considered positive.

Table 1 shows DAP3 interacts with FADD, caspase-8, DR4, and DR5 in yeast two-hybrid assays. Yeast strain EGY48 was transformed with yeast expression plasmids encoding various proteins expressed as fusions with either an N-terminal LexA DNA-binding domain or B42 transactivation domain. Transformants were scored for activation of LEU2 and lacZ reporter genes under the control of LexA operators. Plasmid combinations that resulted in growth on leucine-deficient media within 4 days were scored as positive (+). β-galactosidase activity of each colony was also tested by filter assay and scored as blue (+) or white (−) after 60 min. Agreement between both methods of assay was obtained in all cases.

TABLE 1

DAP3 Interactions in Yeast Two-hybrid Assays

| DBD | TA | Leu | β-Gal |
| --- | --- | --- | --- |
| FADD | DAP3 | + | + |
| FADD | Empty | − | − |
| Empty | DAP3 | − | − |
| Casp 8 | FADD | + | + |
| Casp 8 | Fas | − | − |
| Casp 8 | DAP3 | + | + |
| Casp8 PRO | DAP3 | + | + |
| Casp8 CAT | DAP3 | − | − |
| Casp9 CARD | DAP3 | − | − |
| Empty | Casp 8 | − | − |
| FADD | Casp 8 | + | + |
| DAP3 | Casp 8 | + | + |

TABLE 1-continued

DAP3 Interactions in Yeast Two-hybrid Assays

| DBD | TA | Leu | β-Gal |
|---|---|---|---|
| DAP3 | Empty | − | − |
| Fas | FADD | + | + |
| Fas | DAP3 | − | − |
| DR4 | FADD | − | − |
| DR4 | DAP3 | + | + |
| DR5 | FADD | − | − |
| DR5 | DAP3 | + | + |

DAP3 binding activity, association with FADD, and regulation of FADD-induced apoptosis was tested (FIG. 1). For co-immunoprecipitation assays, HEK293T or HEK293-EBNA cells ($2\times10^6$) in 10 cm plates were transiently transfected with 10 μg of each protein-encoding plasmids (20 μg total DNA) using 50 μl of Superfect™ (QIAGEN; Valencia Calif.) and harvested 1 day later. Alternatively, $2-5\times10^8$ untransfected Jurkat or HTIO80 cells were used without transfection. Cells were suspended in 0.5 ml lysis buffer containing 0.1% NP-40, 20 mM Tris-HCl, pH 7.5, 2 mM $MgCl_2$, 1 mM EGTA, 130 mM NaCl (500 mM in the case of caspase-8) and protein inhibitors (Boehringer Mannheim/Roche Molecular Biochemicals; Indianapolis Ind.). In some cases, 0.1 mM ATP, ATPγS, GTP, or GTPγS was added to lysates. After pre-clearing with normal mouse or rabbit IgG and 25 μl Protein A- or protein G-agarose, immunoprecipitations (IPs) were performed using 25 μl of anti-FLAG antibody M2-conjugated agarose (Sigma; St. Louis Mo.), or using anti-HA antibody 12CA5 (Boehringer Mannheim), anti-DAP3 (BD Biosciences—Transduction Labs; Lexington Ky.), anti-DR4 (Santa Cruz Biotechnology; Santa Cruz Calif.), or anti-Fas (ALEXIS Biochemicals; San Diego Calif.) in combination with Protein A- or G-SEPHAROSE (25 μl) at 4° C. for 4 hrs. Controls included IPs performed with an equivalent amount of normal mouse or rabbit IgG or unconjugated agarose. After extensive washing with lysis buffer, immune-complexes were fractionated by SDS-PAGE and transferred to nitrocellulose for immunoblotting using various antibodies, followed by incubation with HRPase-conjugated antibodies and detection using an enhanced chemiluminescence (ECL) system (Amersham Pharmacia Biotech Inc.; Piscataway N.J.).

FIG. 1A shows that endogenous DAP3 associates with endogenous FADD. Lysates from untransfected Jurkat and HT1080 cells were subjected to immunoprecipitation (IP) using either anti-DAP3 or control mouse IgG. Immune-complexes were analyzed by SDS-PAGE and immunoblotting using anti-FADD (FIG. 1A, top panel) and anti-DAP3 (FIG. 1A, lower panel) antibodies. FIG. 1B shows that DAP3 association with FADD is Fas-inducible. HEK293T cells were transfected with plasmids encoding DAP3-Flag, FADD-HA, or both. After 1 day, cells were cultured without (−) or with (+) 100 ng/ml anti-Fas antibody CHll and then lysed after 15 minutes. IPs were performed on cell lystates using anti-Flag, followed by immunoblotting using anti-HA (FIG. 1B, top panel). The lysates (30 μp) were also analyzed directly without IP by SDS-PAGE and immunoblotting using anti-Flag and anti-HA antibodies (FIG. 1B, lower panels).

Figure 1C:
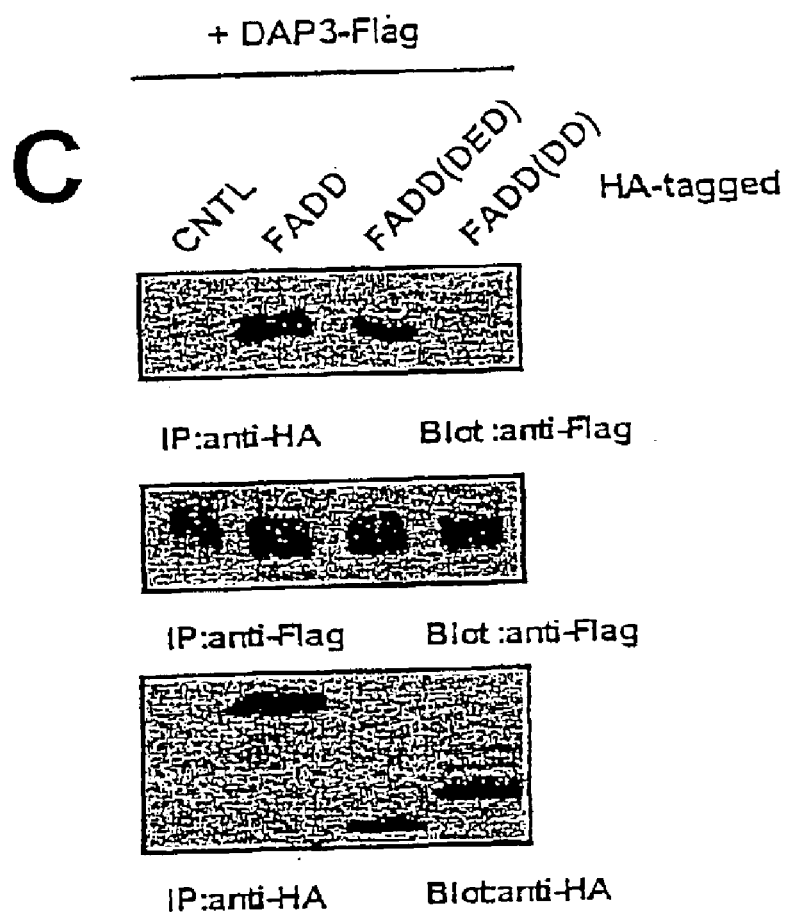
FIG. 1C DAP3 binding to the DED of FADD in transfected 293T cells.

FIG. 1C shows DAP3 binds the DED of FADD. 293T cells were transfected with plasmids encoding DAP3-Flag together with empty plasmid (CNTL), or plasmids encoding HA-tagged full-length FADD, FADD(DD) (residues 81–208), or FADD(DED) (residues 1–80). Lysates were prepared 1 day later and equivalent aliquots were subjected to IP using either anti-HA or anti-Flag antibody, followed by immunoblot analysis using anti-Flag or anti-HA as indicated. FIG. 1D shows mapping of FADD-binding region in DAP3. 293T cells were transfected with plasmids encoding FADD-HA and either empty plasmid (CNTL) or plasmids encoding Flag-tagged full-length DAP3, DAP3 (ΔC) (residues 1–230) or DAP3 (ΔN) (residues 231–398) (FIG. 1D, lower panel). IPs and subsequent immunoblot analysis of immune-complexes were then performed using anti-HA and anti-Flag antibodies, as described above.

Figure 1E:
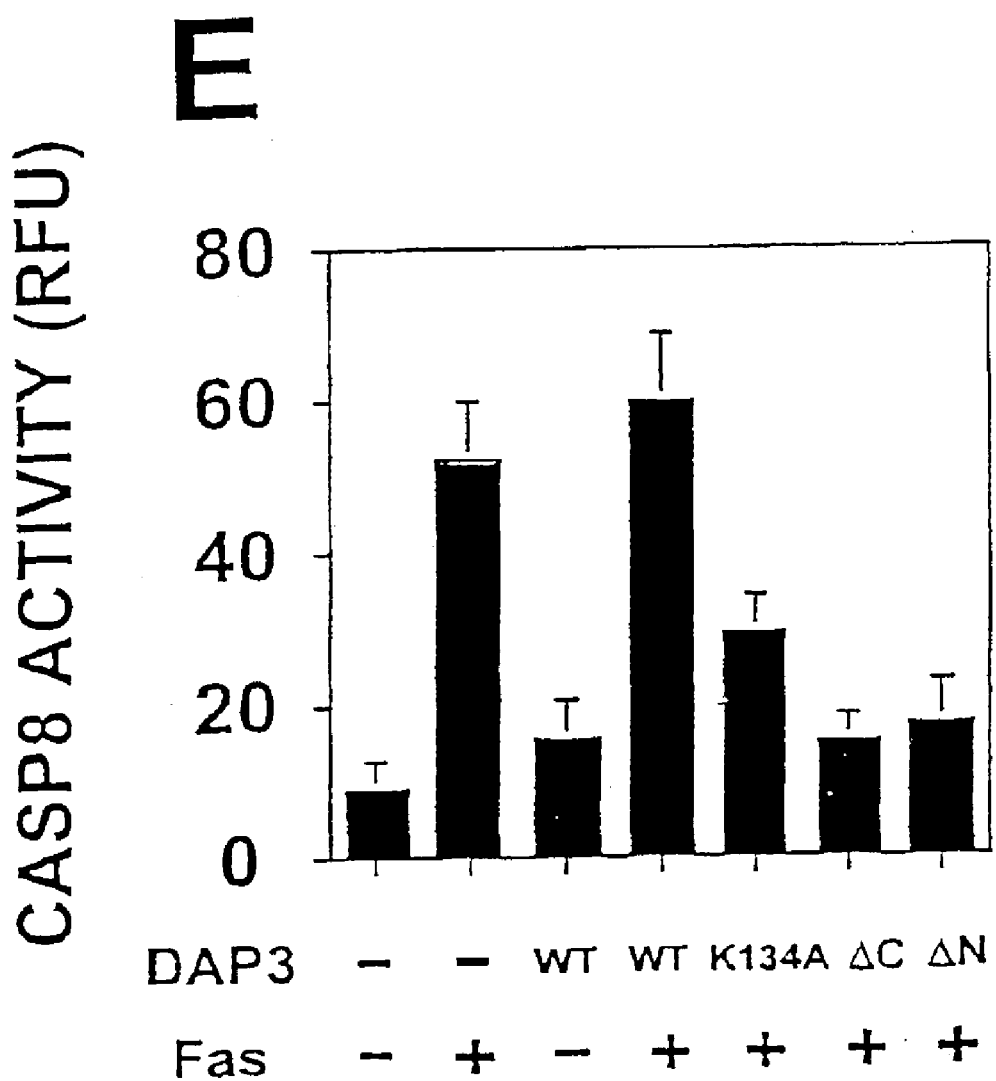
FIG. 1E shows that DAP3 modulates Fas-mediated generation of caspase-8-like protease activity in transfected 293T cells. Lysates were assayed for caspase-8 protease activity.
Figure 1F:
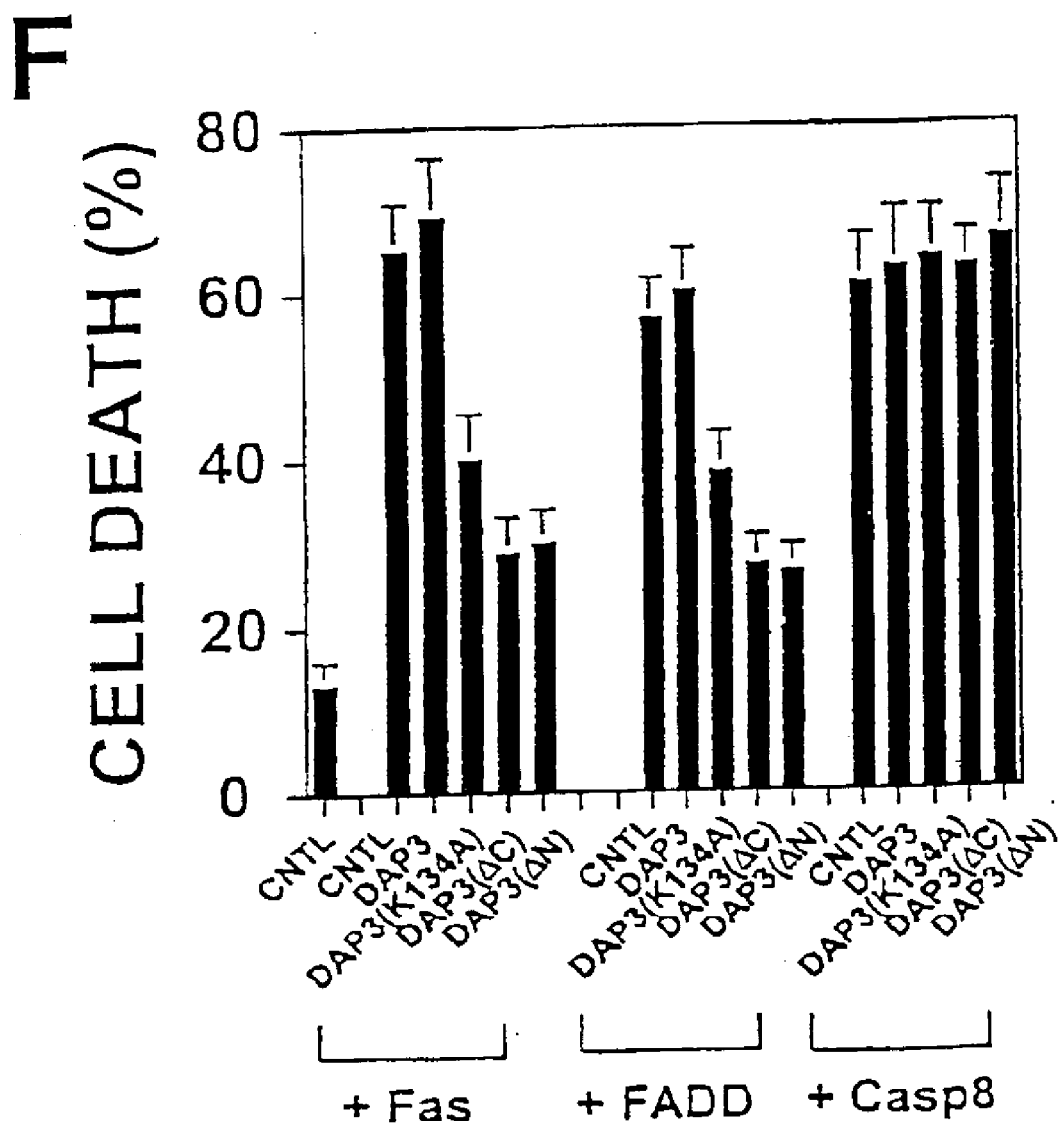
FIG. 1F shows regulation of Fas- and FADD-induced apoptosis by DAP3 in transfected 293-EBNA cells.

FIG. 1E shows that DAP3 modulates Fas-mediated generation of caspase-8-like protease activity. 293T cells were transfected with empty (−) or Fas-encoding (+) plasmids, together with empty plasmid (−) or plasmids encoding full-length wild-type (WT) DAP3, DAP3 (K134A), DAP3 (ΔN), or DAP3 (ΔC). After 1 day, lysates were assayed for protease activity using the caspase-8 substrate Ac-IETD-AFC, expressing data as relative fluorescence units (RFU) after normalization for total protein concentration. FIG. 1F shows that DAP3 regulates Fas- and FADD-induced apoptosis. 293-EBNA cells were transfected with empty plasmid (CNTL) or plasmids encoding Fas, FADD, or pro-Casp8, in combination with empty plasmid (CNTL) or plasmids encoding full-length DAP3, DAP3 (K134A), DAP3 (ΔN), or DAP3 (ΔC). The percentage (±S.D.) of dead cells was determined 1 day later by trypan blue dye exclusion. Apoptosis was also confirmed by UV-microscopic examination of DAPI-stained fixed cells.

The endogenous FADD protein could be readily co-immunoprecipitated with endogenous DAP3 from cell lysates (FIG. 1A) and, vice versa, endogenous DAP3 could be co-immunoprecipitated with endogenous FADD but not with several other proteins tested. The association of FADD with DAP3 was also markedly increased by stimulation of cells with agonistic anti-Fas antibody CH11 (FIG. 1B) but not by other types of unrelated apoptotic stimuli.

To map the domain in FADD responsible for binding DAP3, truncation mutants of FADD were engineered containing either the DD or DED with HA-epitope tags and co-expressed with Flag-tagged DAP3 by transient transfection in HEK293T cells. Based on co-immunoprecipitation assays, the DED of FADD was determined to interact with DAP3 (FIG. 1C). The regions of DAP3 that interact with FADD were also tested using co-immunoprecipitation assays in experiments where full-length DAP3 was compared with N-terminal or C-terminal truncation mutants of DAP3, expressed as Flag-tagged proteins. Full-length DAP3 and DAP3 lacking the N-terminal residues 1–230 (DAP3ΔN) associated with FADD, whereas DAP3 lacking C-terminal residues 231–398 (DAP3ΔC) did not (FIG. 1D). Thus, FADD binds the C-terminal domain of DAP3.

Since FADD is required for Fas-induced processing and activation of pro-Casp8 (Boldin et al., *Cell* 85:803–815 (1996)), the effects of expressing wild-type (WT) and mutant versions of DAP3 were tested on Fas-induced activation of caspases using the fluorigenic caspase-8 substrate Acetyl-Isoleucine-Glutamate-Threonine-Aspartyl-7-Amino-4-Trifluroromethyl-Coumarin Ac-IETD-AFC) (Thornberry et al., *J. Biol. Chem.* 272:17907–17911 (1997)). Over-expression of DAP3 did not significantly increase the amount caspase-8-like protease activity generated in cells in response to agonistic anti-Fas antibody (FIG. 1E). In contrast, caspase-8-like activity was substantially reduced by over-expression of the DAP3ΔN and DAP3ΔC truncation mutants or by DAP3 (K134A), in which the P-loop motif was mutated. These protease activity results correlated with processing of pro-Casp8, as determined by immunoblotting. Furthermore, expression of these DAP3 mutants by transient transfection suppressed cell death induced by over-expression of Fas or FADD but not by over-expression of pro-Casp8 (FIG. 1F), suggesting that DAP3 functions downstream of Fas and FADD but upstream of caspase-8. The DAP3 mutants however had no effect on cell death and apoptosis induced by unrelated cell death stimuli, such as staurosporine or anticancer drugs. Thus, consistent with its ability to bind FADD, DAP3 modulates apoptosis signaling through the Fas/FADD pathway at a proximal step, affecting activation of caspase-8.

II. DAP3 Binds Prodomain of Pro-Casp8 and Regulates Caspase-8 Activation

During two-hybrid assays, evidence was obtained that DAP3 can bind pro-Casp8 as well as FADD (Table 1). Therefore, the effect of DAP3 on caspase-8 activation was further tested. For recombinant DAP3 production and bioactivity assay, pET21d-N-DAP3-His$_6$ was expressed in BL-21 cells (Stratagene Inc.; San Diego Calif.). Cells were grown in LB/ampicillin at 37° C. to an O.D.$_{600\ nm}$ of 0.5, then induced using 1 mM IPTG for 4 hrs before lysing by sonication in (50 mM NaH$_2$ PO$_4$, pH8.0, 300 mM NaCl, 10 mM imidazole, 1 mg/ml lysozyme). DAP3-His$_6$ protein was affinity-purified using Ni-NTA spin-columns (QIAGEN Inc.; Valencia Calif.). pGEX4T-1 encoding GST, GST-Fas (residues 191–335), GST-TNFR2 (residues 266–439), GST-DR4 (residues 269–468) were expressed in XL-1-Blue cells (Stratagene) and affinity-purified using glutathione-SEPHAROSE 4B as described (Sato et al., *FEBS Lett.* 358:113 (1995)).

In vitro translated (IVT) pro-Casp8 and FADD proteins were produced using TNT-coupled reticulocyte lysates (Promega, Inc.; Madison Wis.) and pcDNA3-Flag-FADD or pcDNA3Flag-pro-Casp8. Negative controls were generated by IVT of empty pcDNA3. A total of 4 μl IVT mix was incubated with 200 ng of purified DAP3-His$_6$ protein or TRAF3-His$_6$ (Leo, et al., *J. Biol. Chem.* 274:22414 (1999)) as a negative control in caspase buffer (50 mM HEPES, 100 mM NaCl, 1 mM EDTA, 0.1% CHAPS, 10% sucrose and 5 mM dithiothreitol (DTT)) in a total volume of 20 μl at 37° C. for 30 min. In some cases, 0.1 mM ATP, ATPγS, GTP, or GTPγS was included. Caspase-8 activity was then measured by adding 10 μl of these reaction mixes to 89 μl of caspase buffer, followed by 1 μl of Ac-IETD-AFC (100 μM final concentration)(PharMingen Inc.; San Diego Calif.). Caspase activity was measured in cell lysates using Ac-IETD-AFC as a substrate, normalizing lysates for total protein concentration (Deveraux et al., *Nature* 388:300 (1997); Haraguchi et al., *J. Exp. Med.* 191:1709 (2000)). Caspase activity was measured at 37° C. using a fluorometric plate reader (Perkin-Elmer, LS50B; Norwalk Conn.) in the kinetic mode with excitation and emission wave lengths of 405 and 510 nm, respectively, monitoring release of 7-amino-4-trifluoromethyl-coumarin (AFC) (RFU) from the substrate peptide after 30 min incubation.

Figure 2A:
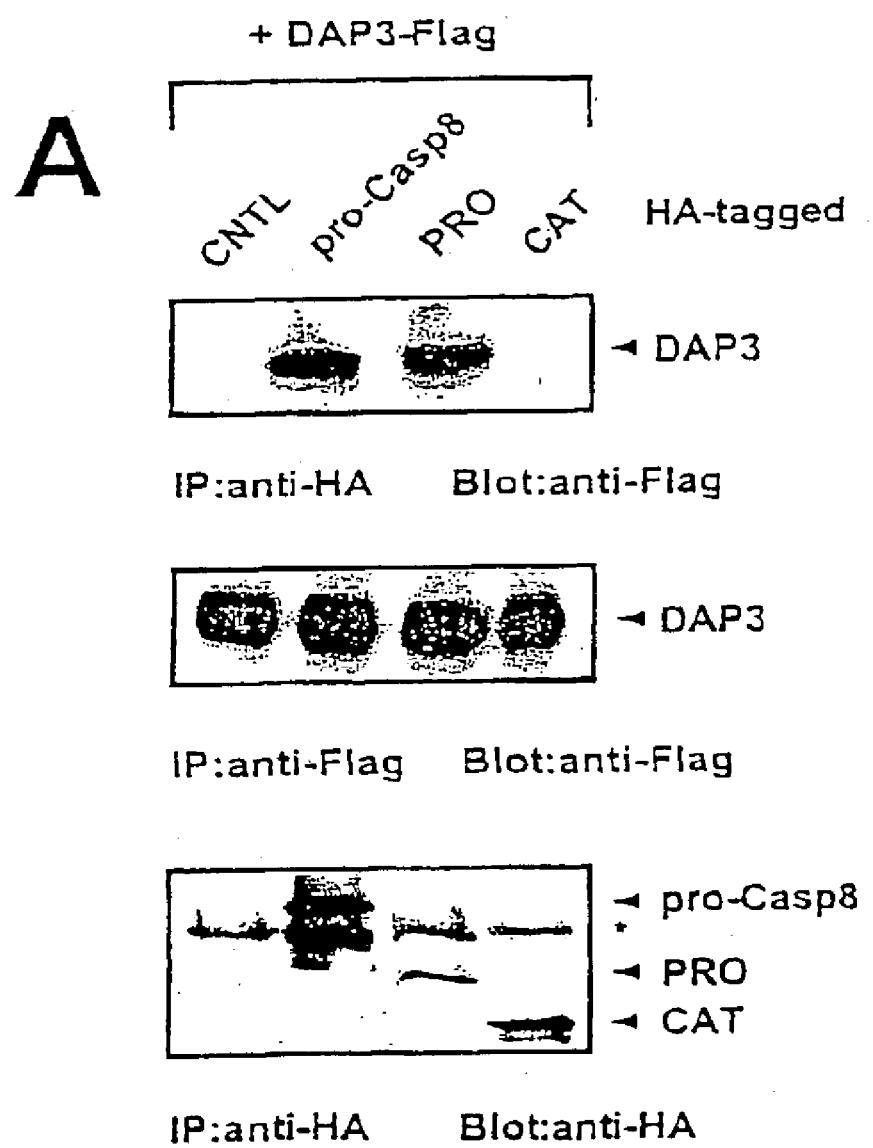
FIG. 2A shows immunoblots of co-immunoprecipitates of transfected 293T cells.
Figure 2B:
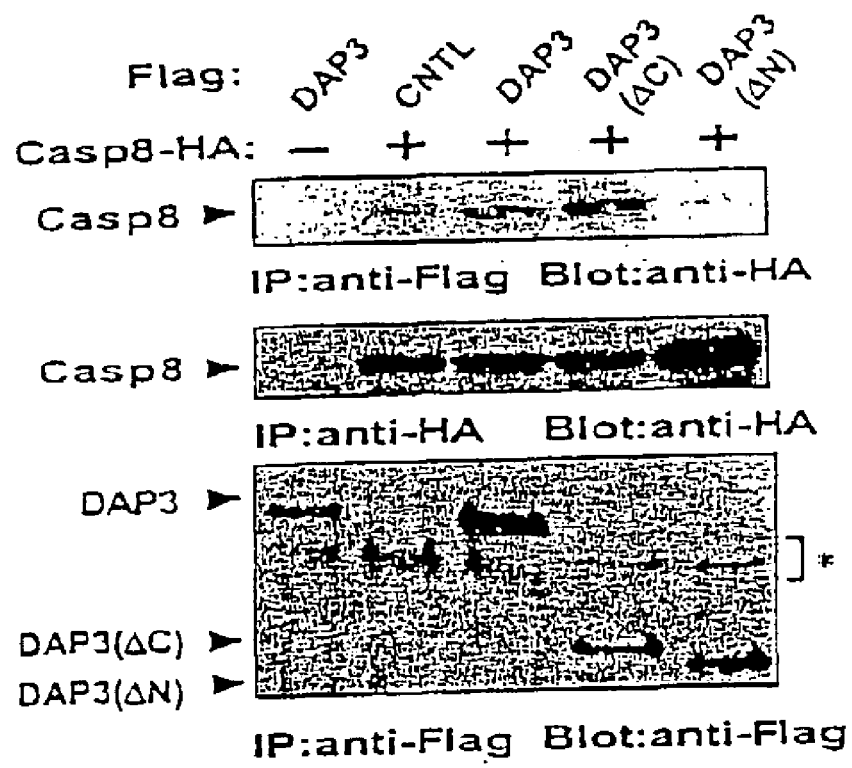
FIG. 2B shows association of the proximal region of DAP3 with pro-Caspase8 in co-immunoprecipitates of transfected 293T cells.

FIG. 2 shows DAP3 binding of prodomain of pro-Casp8 and regulates caspase-8 activation. 293T cells were transfected with plasmids encoding DAP3-Flag in combination with either empty plasmid (CNTL) or plasmids encoding HA-tagged full-length pro-Casp8, prodomain (PRO) (residues 1–215), or catalytic domain (CAT) (residues 212–496)(FIG. 2A). Lysates were prepared 1 day later and equivalent aliquots subjected to IP and immunoblot analysis using anti-Flag and anti-HA antibodies, as indicated in FIG. 2A. Asterisk denotes a non-specific band. FIG. 2B shows that the proximal region of DAP3 associates with pro-Casp8. Co-IP experiments were preformed, as described above, using 293T cells expressing HA-tagged pro-Casp8 in combination with Flag-tagged full-length DAP3, DAP3 (ΔN), or DAP3 (ΔC). Non-specific bands are denoted by asterisks.

Figure 2C:
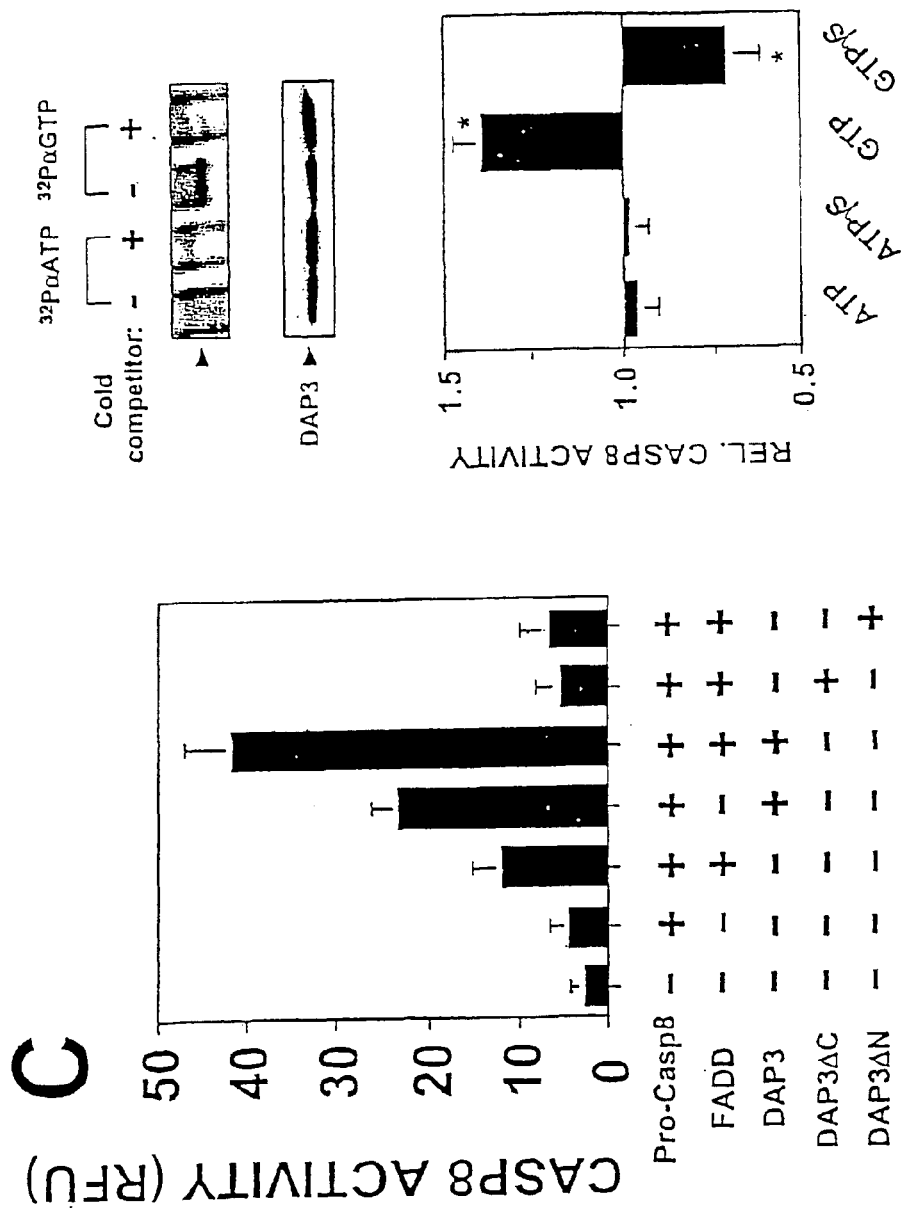
FIG. 2C shows that DAP3 binds GTP and stimulates activation of pro-Caspase8 in vitro in a GTP-dependent manner.

FIG. 2C shows that DAP3 binds GTP and stimulates activation of pro-Casp8 in vitro in a GTP-dependent manner. For nucleotide-binding assays, purified DAP3-His$_6$ protein (2 μg) was preincubated in 50 μl of 10 mM Tris-HCl, pH7.8, 100 mM NaCl, 1 mM DTT, 2 mM MnCl$_2$ and 5 mM (α-$^{32}$P)ATP or 5 mM (α-$^{32}$P) GTP with or without cold competitor (1 mM ATP or 1 mM GTP) at 4° C. for 10 min and irradiated on ice using a UV-lamp (30W) at a distance of 5 cm for 10 min. The samples were passed through SEPHADEX G25 columns and analyzed by SDS-PAGE, autoradiography and immunoblotting using anti-DAP3 antibody.

In vitro translated pro-Casp8, FADD and bacteria-produced purified DAP3-His$_6$ were mixed in various combinations as indicated, and activity of caspase-8 was analyzed based on cleavage of Ac-IETD-AFC (RFU) (mean ±S.D; n=3) (FIG. 2C, left panel). TRAF3-His$_6$ served as a negative control (−) for DAP3-His$_6$. DAP3-His$_6$ protein was incubated with $^{32}$P-labeled ATP or GTP in the presence(+) or absence (−) of excess unlabeled nucleotides (FIG. 2C, right top panel). Nucleotides were UV-crosslinked to DAP3 protein followed by analysis by SDS-PAGE and immunoblotting, where $^{32}$P-bound nucleotides were detected by autoradiography and loading of equivalent amount of DAP3 was confirmed by incubation with anti-DAP3 antibody followed by ECL-detection.

Caspase-8 activation assays were performed using DAP3-His$_6$, FADD, and pro-Casp8, as described above, in the presence of 0.1 mM ATP, ATPγS, GTP, or GTPγS (FIG. 2C, right bottom panel). Data are expressed relative to caspase-8 activity generated in the absence of added nucleotides (mean ±SD; n=3).

Interaction of DAP3 with pro-Casp8 was confirmed by co-immunoprecipitation assays using transiently transfected HEK293T cells (FIG. 2A). Furthermore, DAP3 was determined to bind the N-terminal DED-containing prodomain of pro-Casp8 but not the catalytic domain of this protease (Table 1, FIG. 2A). In contrast to the results obtained for FADD interactions with DAP3, analysis of DAP3 mutants indicated that the N-terminal domain (residues 1–230) of DAP3 associates with pro-Casp8 (FIG. 2B). Thus, while the C-terminal domain of DAP3 binds FADD, the N-terminal portion of DAP3 binds pro-Casp8.

To test the possibility that DAP3 enhances FADD-mediated activation of pro-Casp8, the effects of recombinant purified DAP3 protein was tested on activation of in vitro translated pro-Casp8, measuring caspase-8 protease activity by cleavage of the fluorigenic peptide substrate Ac-IETD-AFC. Mixing FADD with pro-Casp8 resulted in a ~3-fold increase in caspase-8 activity (FIG. 2C). Addition of DAP3 to pro-Casp8 also increased protease activity by ~5-fold, indicating that DAP3 can trigger caspase-8 activation in vitro. Moreover, the co-addition of DAP3 and FADD resulted in a ~10-fold increase in caspase-8 activity, suggesting that the effects of FADD and DAP3 are at least additive and possiblty synergistic. Importantly, addition of recombinant-purified DAP3 dominant-negative mutant proteins, DAP3ΔN or DAP3ΔC, inhibited FADD-induced activation of pro-Casp8 in vitro (FIG. 2C). These data from an in vitro reconstitution system thus provide direct evidence that DAP3 can regulate FADD-mediated activation of pro-Casp8.

DAP3 contains a P-loop motif but has never been directly demonstrated to bind nucleotides. Using recombinant purified DAP3-His$_6$, DAP3 protein was tested for binding in vitro to GTP or ATP, using a UV-crosslinking technique. DAP3-His$_6$ bound specifically to GTP but not ATP (FIG. 2C). Moreover, GTP enhanced whereas GTPγS inhibited DAP3-mediated caspase-8 activation in vitro (FIG. 2C). Thus, GTP binds and regulates the activity of DAP3.

III. DAP3 Directly Binds Cytosolic Domain of DR4 and Modulates Trail Receptor-Induced Apoptosis The Trail receptors, DR4 and DR5, are known to recruit FADD and pro-Casp8 when bound by ligand, but FADD does not directly bind to the intracellular domains of these receptors (Schneider et al., *Immunity* 7:831–836 (1997); Walczak et al., *EMBO J.* 16:5386–5397 (1997); Kischkel et al., *Immunity* 12:611–620 (2000); Sprick et al., *Immunity* 12:599–609 (2000)), suggesting that another protein bridges FADD to DR4 and DR5. During two-hybrid analysis of DAP3 interactions, evidence was obtained that DAP3 binds the cytosolic domains of DR4 and DR5 (Table 1).

FIG. 3 shows that DAP3 directly binds cytosolic domain of DR4 and modulates Trail Receptor-induced apoptosis. FIG. 3A, left panel, shows that the death domain of DR4 is required for association with DAP3. 293T cells were transfected with plasmids encoding DAP3-Flag in combination with either empty plasmid (−) or plasmid encoding full-length DR4 or DR4 lacking the DD (residues 379–468). Co-IP and immunoblot experiments were performed as described above using anti-DR4 and anti-Flag antibodies. FIG. 3A, right panel, shows that endogenous DAP3 associates with DR4 in a ligand-dependent manner. Untransfected HT1080 cells were stimulated with 0.1 µg/ml TRAIL for various times, and lysates were prepared for immunoprecipitation using anti-DR4 or control (CNTL) antibody, followed by SDS-PAGE and immunoblot analysis using anti-DAP3 or anti-DR4 antibodies.

Figure 3A:
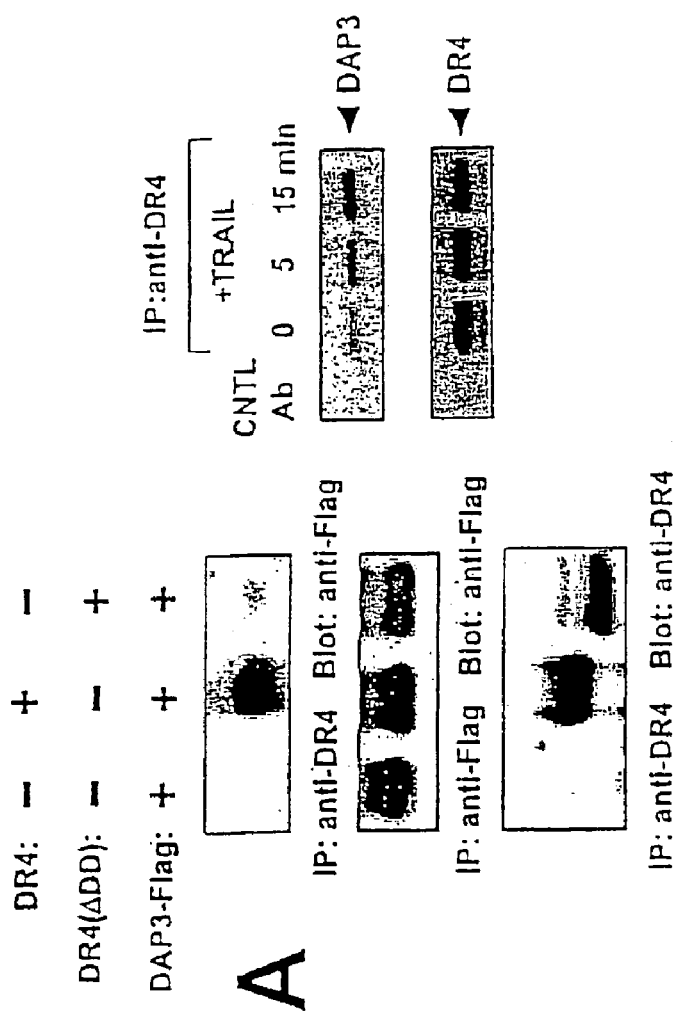
FIG. 3A shows that the Death domain of DR4 is required for association with DAP3 in transfected 293T cells.
Figure 3B:
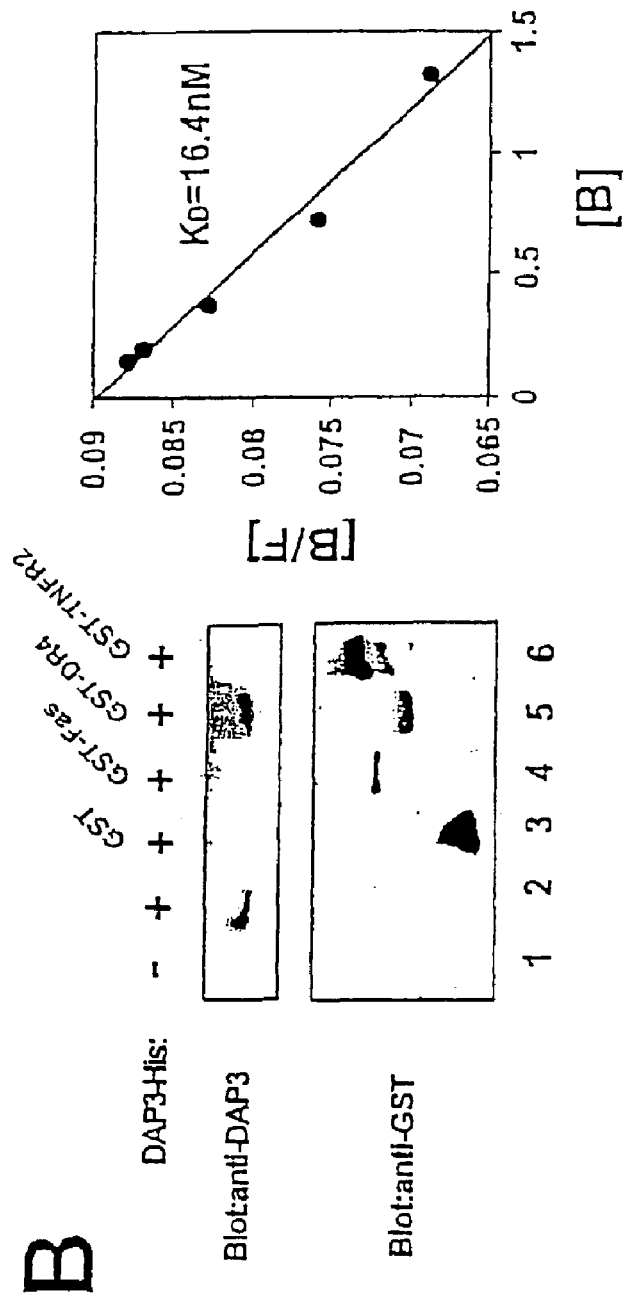
FIG. 3B shows that purified recombinant DAP3 binds purified DR4 cytosolic domain.

FIG. 3B shows that purified recombinant DAP3 binds purified DR4 cytosolic domain. For in vitro protein interaction assays, purified DAP3-His$_6$ protein (+) or TRAF3-His$_6$ (−) (200 ng) were incubated with 1.0 µg of GST, GST-Fas (191–335), GST-DR4 (269–468), or GST-TNFR2 (266–439) immobilized on 10–20 µl of glutathione-beads in 0.1 ml of binding buffer (50 mM Tris-HCl, pH 7.5, 5mM MgCl$_2$, 10% glycerol, 0.5 mg/ml BSA and 5 mM 2-mercaptoethanol) at 4° C. for 60 min. The beads were washed 3-times with 1 ml binding buffer followed by boiling in 25 µl of SDS sample buffer. Eluted proteins were analyzed by SDS-PAGE (12% gel) followed by immunoblotting with anti-DAP3 and anti-GST antibodies. For Scatchard analysis, purified DAP3-His$_6$ protein at 0.1, 0.15, 0.25, 0.5 and 1 µM was incubated with 1.0 µg of GST-DR4 immobilized on 20 µl of glutathione-SEPHAROSE in 0.1 ml of binding buffer at 4° C. for 60 min. Free and DR4-bound DAP3 were separated by centrifugation of beads, and relative amounts of DAP3 in the supernatant and pellet fractions were determined by SDS-PAGE and immunoblotting using anti-DAP3 antibody (with ECL detection; Amersham). Analysis was performed using a scanning laser densitometry analysis of x-ray films (LKB densitometer; Amersham Pharmacia Biotech).

Figure 3C:
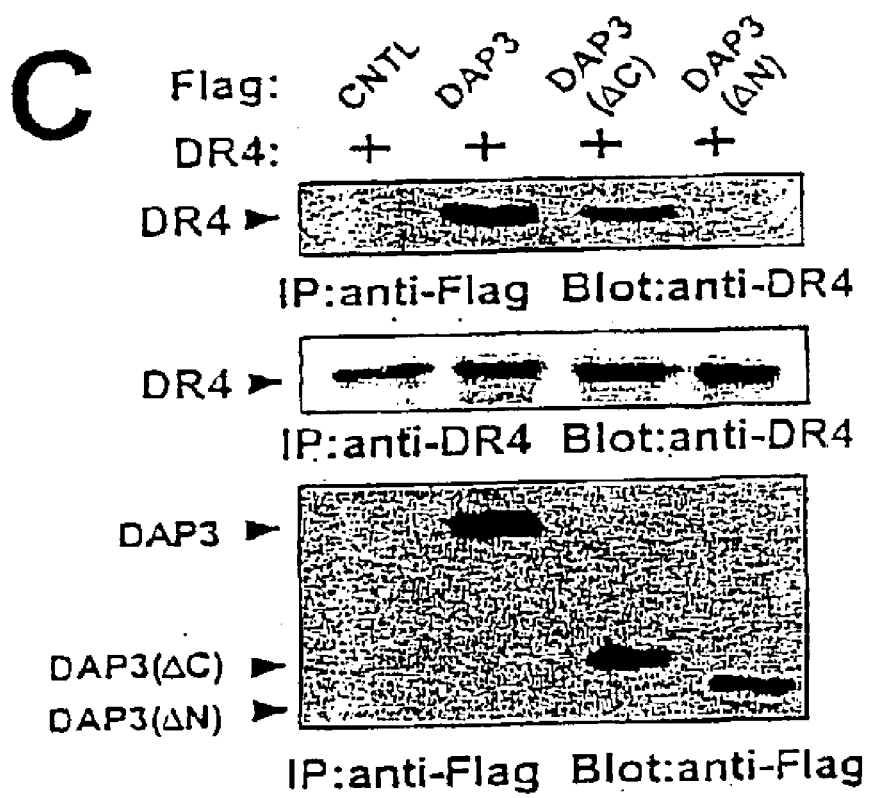
FIG. 3C shows mapping of a region in DAP3 required for binding DR4.

DAP3-His$_6$ protein was produced and purified from bacteria, then assayed for in vitro binding to purified cytosolic domains of Fas (lane 4), DR4 (lane 5) and TNFR2 (lane 6) expressed as GST-fusion proteins, or GST control protein (lane 3), immobilized on glutathione-SEPHAROSE (FIG. 3B, left panel). DAP3-His$_6$ was loaded directly in the gel (lane 2) for assessing the proportion of input DAP3-His$_6$ recovered with immobilized GST-fusion proteins. Note that ~10–20% of input DAP3-His$_6$ bound GST-DR4. Lane 1 shows an equivalent amount of control His$_6$-protein (TRAF3). His$_6$-TRAF3 did not bind to GST-DR4, confirming the specificity of the results. Scatchard analysis of DAP3-His$_6$ binding to GST-DR4 cytosolic domain is shown in FIG. 3B, right panel. For mapping of the region in DAP3 required for binding DR4, 293T cells were transfected and co-IP/immunoblot assays were preformed (FIG. 3C).

Figure 3D:
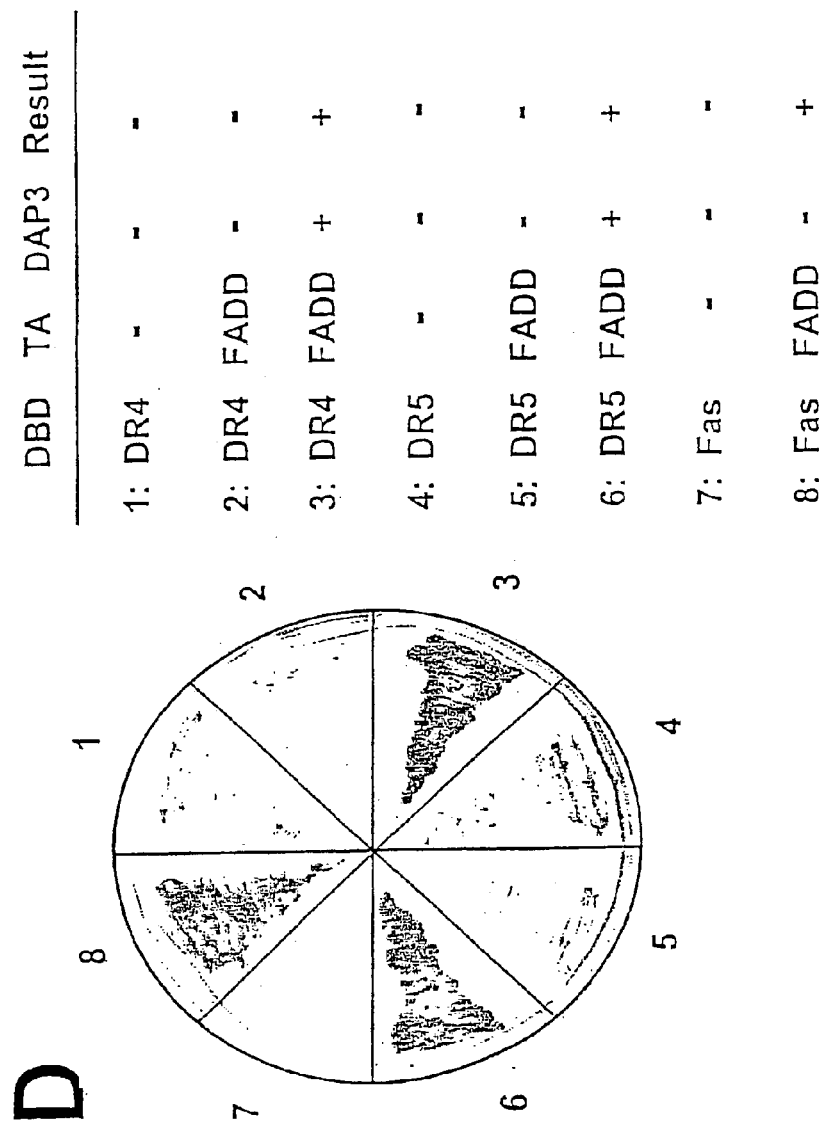
FIG. 3D shows that DAP3 mediates binding of DR4 and DR5 to FADD in a yeast 3-hybrid assay.

FIG. 3D shows that DAP3 mediates binding of DR4 and DR5 to FADD, as demonstrated by yeast 3-hybrid assay. Yeast cells were transformed with expression plasmids encoding various proteins expressed as fusions with either a N-terminal LexA DNA-binding domain (DBD) or B42 transactivation domain (TA), with (+) or without (−) p426-DAP3 expression plasmid. Transformants were scored for activation of LEU2 reporter gene, based on ability to grow when streaked on leucine-deficient medium.

Figure 3E:
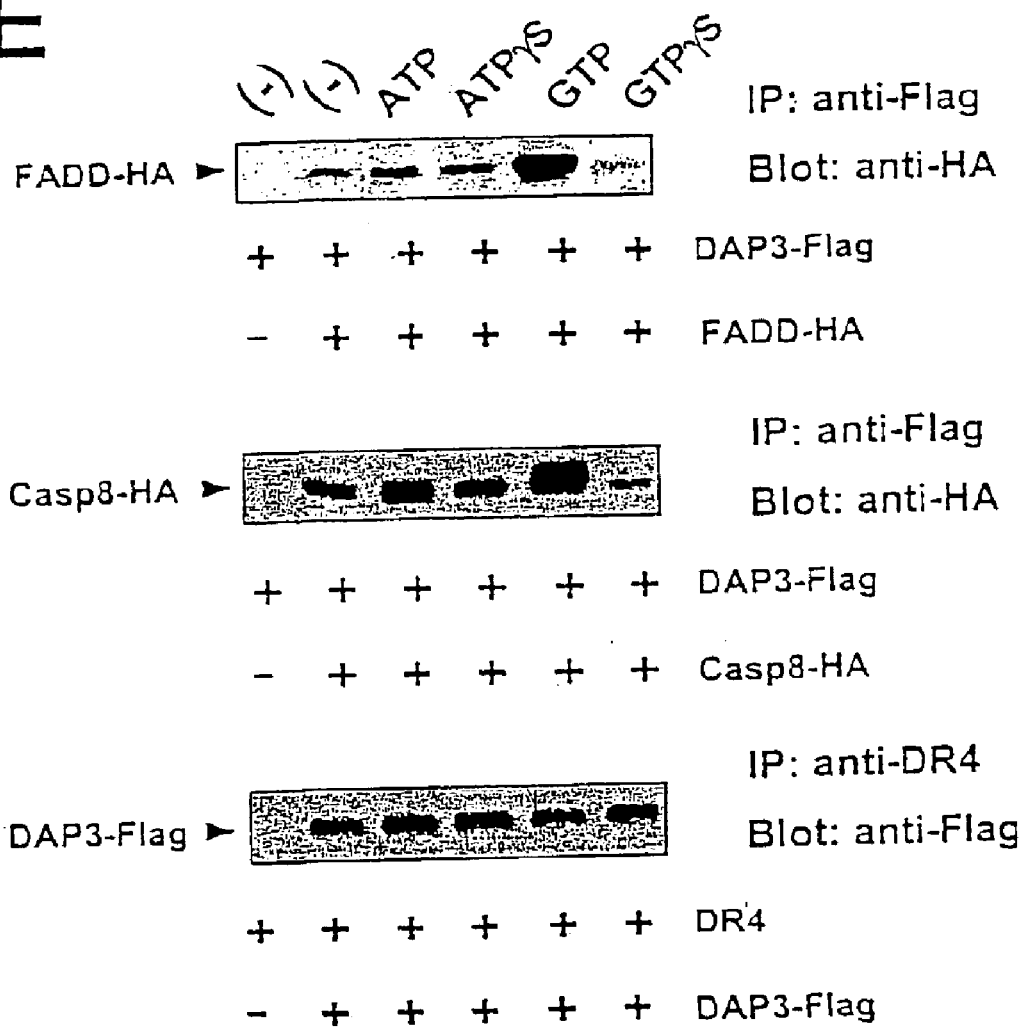
FIG. 3E shows that DAP3 association with FADD and pro-Caspase8 is GTP-dependent.
Figure 3F:
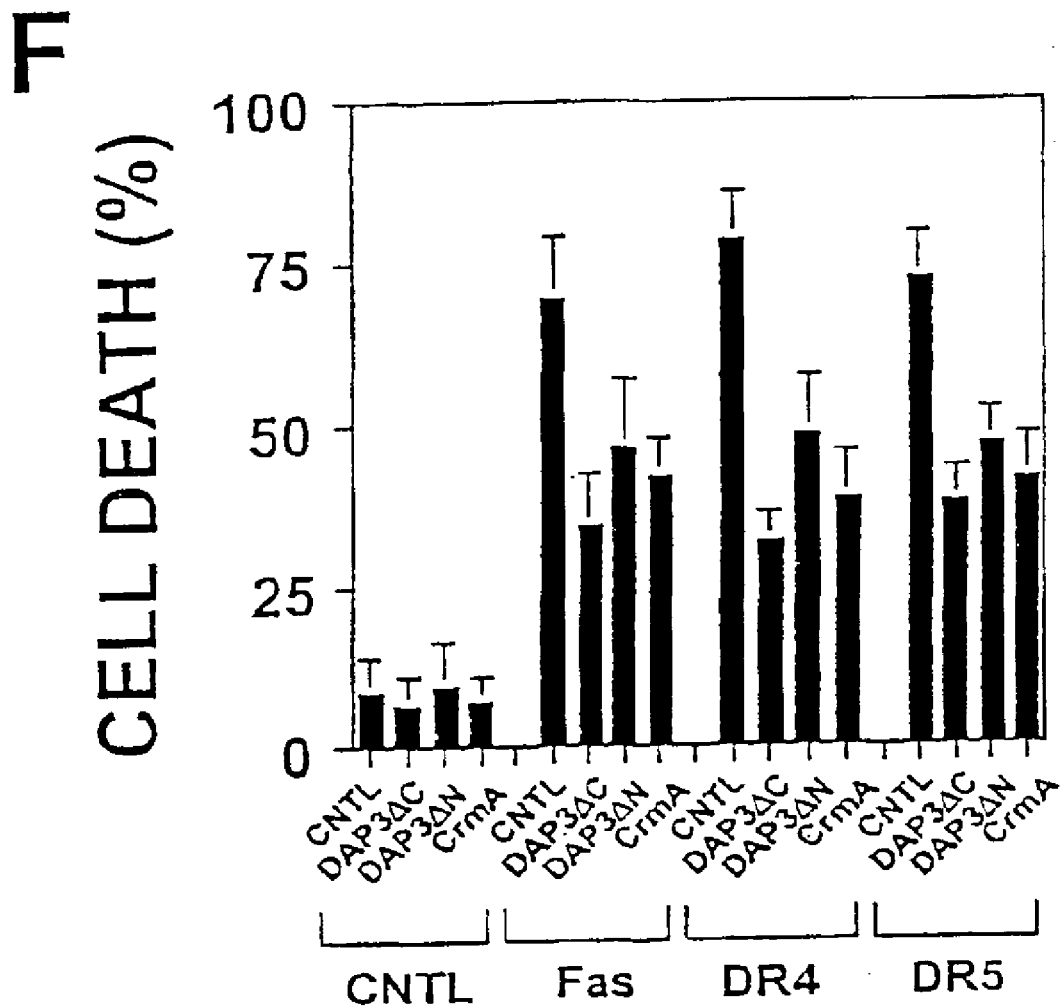
FIG. 3F shows that DAP3 modulates apoptosis induction by Trail Receptors in transfected 293-EBNA cells.

FIG. 3E shows that DAP3 association with FADD and pro-Casp8 is GTP-dependent. Nucleotide-dependence of interactions of DAP3 with FADD (top), pro-Casp8 (middle), and DR4 (bottom) were analyzed by adding 0.1 mM ATP, ATPγS, GTP, or GTPγS to lysates prior to performing co-immunoprecipitation assays. FIG. 3F shows that DAP3 modulates apoptosis induction by Trail Receptors. 293-EBNA cells were transfected with either empty plasmid (CNTL) or plasmids encoding Fas, DR4 or DR5, in combination with either empty plasmid or plasmids encoding DAP3 (ΔN), DAP3 (ΔC), or the caspase-8 inhibitor, cowpox CrmA. Transfected cells were stimulated 1 day later with 0.1 µg/ml agonistic anti-Fas antibody or 0.1 µg/ml TRAIL. The percentage of dead cells was determined 16 hrs later by trypan blue dye exclusion (mean±S.D.; n=3) (Varfolomeev et al., *Immunity* 9:267–276 (1998)).

Figure 3G:
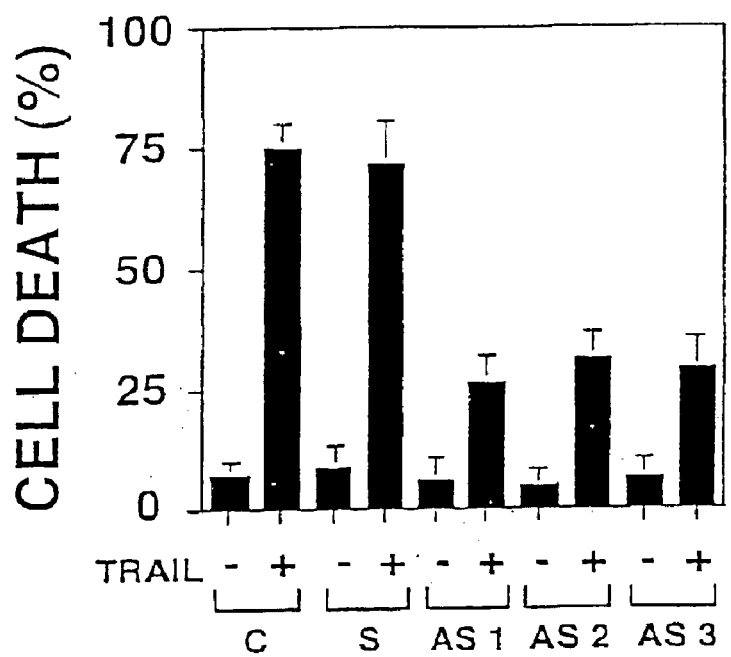
FIG. 3G shows that endogenous DAP3 is required for TRAIL-induced apoptosis using antisense oligonucleotides.

FIG. 3G shows that endogenous DAP3 is required for TRAIL-induced apoptosis. For antisense experiments, phosphodiester sense (5'-ATGATGCTGAAAGGAATA-3'; SEQ ID NO:40) and antisense oligonucleotides 1, 2 or 3 (see FIG. 3G; SEQ ID NO:41) targeting DAP3 were synthesized and purified (Integrated DNA Technologies Inc.; Coralville Iowa). Oligonucleotides at 1.33 µg/ml in TE buffer were mixed with 50 µl LIPOFECTAMINE (Life Technolgies/Gibco; Rockville Md.) in 2.5 ml OPTI-MEM medium, incubated at room temperature for 45 minutes, then added to cultures of Jurkat cells (10$^7$) in 2.5 ml OPTI-MEM and cultured at 37° C. in 5% CO$_2$ for 4 hrs before adding 15 ml RPMI-1640, 10% FBS complete medium (40 µM final oligonucleotide concentration) and returning cells to culture. The oligonucleotide delivery procedure was repeated on days 1 and 2. At 3 days after initiating cultures, the cells were stimulated or not stimulated with soluble Trail (100 µg/ml) and a crosslinking antibody (2 µg/ml) (ALEXIS Biochemicals) for 16 hrs before preparing cell lysates for immunoblot analysis or determining cell viability by trypan blue dye exclusion assay.

As shown in FIG. 3G, sense (S) or antisense (AS) oligonucleotides targeting DAP3 (FIG. 3G, top panel) were introduced into Jurkat cells by lipofection. After 1 day, cells were cultured with (+) or without (−) 0.1 µg/ml soluble TRAIL for 16 hrs. Half of these cells were used for cell viability assays (% dead cells; mean±S.D.; n=3) (FIG. 3G, middle panel) and half were lysed and used for assessment of DAP3 and DR4 protein levels by immunoblotting (samples normalized for total protein content) (FIG. 3G, lower panel).

Association of DAP3 with DR4 and DR5 was confirmed by co-immunoprecipitation experiments using transiently transfected HEK293T cells (FIG. 3A). In contrast, DAP3 did not co-immunoprecipitate with a DR4 mutant lacking the DD. Endogenous DAP3 protein could also be co-immunoprecipitated with endogenous DR4 after stimulation with TRAIL, indicating a ligand-inducible interaction (FIG. 3A).

To explore whether DAP3 directly binds the cytosolic domain of DR4, both proteins were expressed in bacteria, purified, and tested for interactions. As shown in FIG. 3B, DAP3-His$_6$ bound to GST-DR4 (cytosolic domain) but not to GST, GST-Fas or GST-TNFR2. Scatchard analysis indicated that DAP3 binds the cytosolic domain of DR4 with high-affinity ($K_D$~16 nM), supporting the notion that this interaction is physiologically relevant. The region within DAP3 required for binding DR4 was also mapped by expressing the DAP3 (ΔN) and DAP3 (ΔC) proteins. DR4 was determined to bind the proximal domain of DAP3 (FIG. 3C). Thus, the proximal region of DAP3 (residues 1–230) binds the DD of DR4, whereas the distal region (residues 231–398) binds the DED of FADD.

These results suggested that DAP3 potentially could serve as the missing link between the Trail receptors and FADD. To test this hypothesis, yeast 3-hybrid experiments were performed to determine whether DAP3 could mediate interactions between FADD and the cytosolic domains of DR4 and DR5 in a heterologous cellular background. Indeed, whereas FADD fused to a transactivation domain (TA) failed to bind the cytosolic domains of DR4 or DR5 fused to the DNA-binding domain of a transcription factor in the absence of DAP3, co-expression of DAP3 with these proteins induced reporter gene activation (FIG. 3D). In contrast, DAP3ΔN and DAP3ΔC did not reconstitute 3-hybrid interactions in these assays. Thus, DAP3 can bridge FADD to the cytosolic domains of DR4 and DR5.

The nucleotide-dependence of DAP3 interactions with TRAIL receptors was examined by addition of GTP or GTPγS (as well as ATP or ATPγS, used as controls) to lysates prior to co-immunoprecipitation (FIG. 3E). GTP enhanced while GTPγS inhibited association of DAP3 with FADD and with pro-Casp8. In contrast, binding of DR4 to DAP3 was unaffected by nucleotides. Therefore, GTP-binding is critical for DAP3 interactions with FADD and pro-Casp8 but not with TRAIL receptors.

The functional significance of DAP3 for apoptosis induction by DR4 and DR5 was interrogated by either over-expressing dominant-negative mutants of DAP3 in cells (FIG. 3F) or by ablating endogenous DAP3 expression using antisense oligonucleotides (FIG. 3G). Both approaches resulted in suppression of cell death caused either by over-expression of Trail-receptors or treatment of cells with soluble purified Trail protein. Thus, DAP3 is a critical component of the Trail receptor signal transduction apparatus.

IV. Sequence Analysis of DAP3 and Identification of DED and NB-ARC Domains

DAP3 was first discovered during a screen for suppressors of interferon-γ-induced apoptosis of HeLa cells using a functional cloning strategy in which cDNA are expressed in antisense orientation (Kissil et al., *J. Biol. Chem.* 270:27932–27936 (1995)). Based on BLAST searches, DAP3 lacks significant homology to other known apoptosis regulators. However, the functional evidence linking DAP3 to caspase activation and its ability to interact with the DEDs of FADD and pro-Casp8 prompted a more carefully analysis of the sequence of this protein using other methods. For sequence analysis, sequence alignments were performed using MEG-ALIGN (DNAStar, Inc.; Madison Wis.).

Molecular modeling was performed using MODELLER (Sali and Blundell, *J. Mol. Biol.* 234:779–815 (1993)) and FFAST (Jaroszewski et al., *Protein Science* 7:1431–1440 (1998)).

Figure 4A:
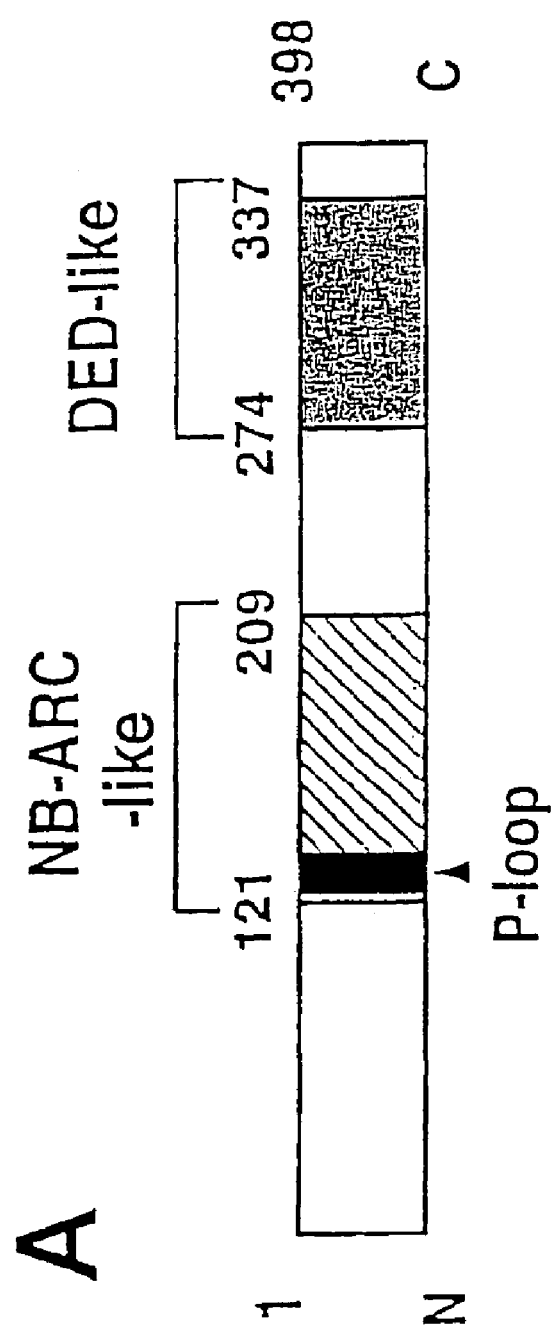
FIG. 4A shows a schematic representation of human DAP3 protein, indicating locations of NB-ARC-like and DED-like domain, as well as position of the P-loop motif.

FIG. 4 shows sequence analysis of DAP3, revealing similarities to DED and NB-ARC domains. FIG. 4A shows a schematic representation of human DAP3 protein, indicating locations of NB-ARC-like and DED-like domain, as well as the position of the P-loop motif. Amino acid positions are indicated by numbers. FIG. 4B shows an alignment of the amino acid sequence of NB-ARC domains of human Apaf-1 and *C. elegans* CED4 with residues 115–213 of DAP3. Asterisks indicate nucleotide-binding motifs. FIG. 4C shows a sequence alignment of DEDs of pro-Casp8, 10, and FADD with residues 268–337 of DAP3. Identical and similar residues are indicated in black and gray blocks, respectively.

Alignment of the N-terminal domain of DAP3 (residues 115–213) with the caspase-activating proteins Apaf-1 and CED4 reveals a region of amino-acid sequence similarity (29% and 21%, respectively), which includes the predicted nucleotide-binding motifs (G-K-S/T) of these proteins (FIG. 4A and B). In comparison, the NB-ARC of human Apaf-1 and *C. elegans* CED4 are 17% similar. The C-terminal domain of DAP3 (residues 268 to 337) shares amino acid sequence similarity with the DEDs of FADD, pro-Casp8 and 10 (FIG. 4C), ranging from 12–25% (mean 19.2%) amino acid similarity. In comparison, the DEDs of FADD, pro-Casp8 and pro-Casp10 are 18–39% similar (mean 29.5%).

Gene ablation studies in mice indicate that caspase-8 represents the essential apical caspase in TNF-family death receptor signaling (Varfolomeev et al., *Immunity* 9:267–276 (1998); Juo et al., *Curr. Biol.* 8:1001–1008 (1998)). The zymogen form of caspase-8 (p45) possesses roughly 1% of the protease activity of the processed fully-active enzyme, and thus bringing pro-Casp8 molecules into close apposition can allow them to trans-processes each other via the "induced-proximity" mechanism (Muzio et al., *J. Biol. Chem.* 273:2926–2930 (1998)). Caspase-8 activation can be achieved experimentally by over-expressing pro-Casp8, relying on self-association of its N-terminal DED-containing prodomain, or by fusing the unprocessed catalytic domain (p20/p10) to heterologous dimerization domains (Salvesen et al., *Proc. Natl. Acad. Sci. USA* 96:10964–10967 (1999)). In vivo, however, where levels of pro-Casp8 are probably limiting, caspase-8 activation requires assembly of a multiprotein death-induced signaling complex (DISC). DAP3 represents a previously unrecognized component of this complex. The ability of DAP3 to bind GTP raises the possibility that it can function as a GTP-dependent molecular-switch for mediating protein interactions analogous to Ras and G-proteins. Though ATP/dATP-dependent oligomerization of caspase-activating CED4/Apaf1-family proteins has been described (Yang et al., *Science* 281:1355–1357 (1998); Srinivasula et al., *Mol. Cell* 1:949–957 (1998)) self-association of DAP3 has not been observed, suggesting a different mechanism is involved. Since small-molecule drugs have been developed against the nucleotide-binding pockets of kinases, similar approaches can be employed to identify pharmacological antagonists of DAP3 for suppression of death receptor signaling in inflammatory, autoimmune, and ischemic diseases, where TNF-family death receptors play a role (Nagata, *Genes Cells* 1:873–879 (1996); Wang and Lenardo, *Curr. Opin. Immunol.* 9:818–825 (1997)).

V. IRAK Protein Containing Death Domain

This example describes a novel death domain-containing protein of the IRAK family.

Figure 5:
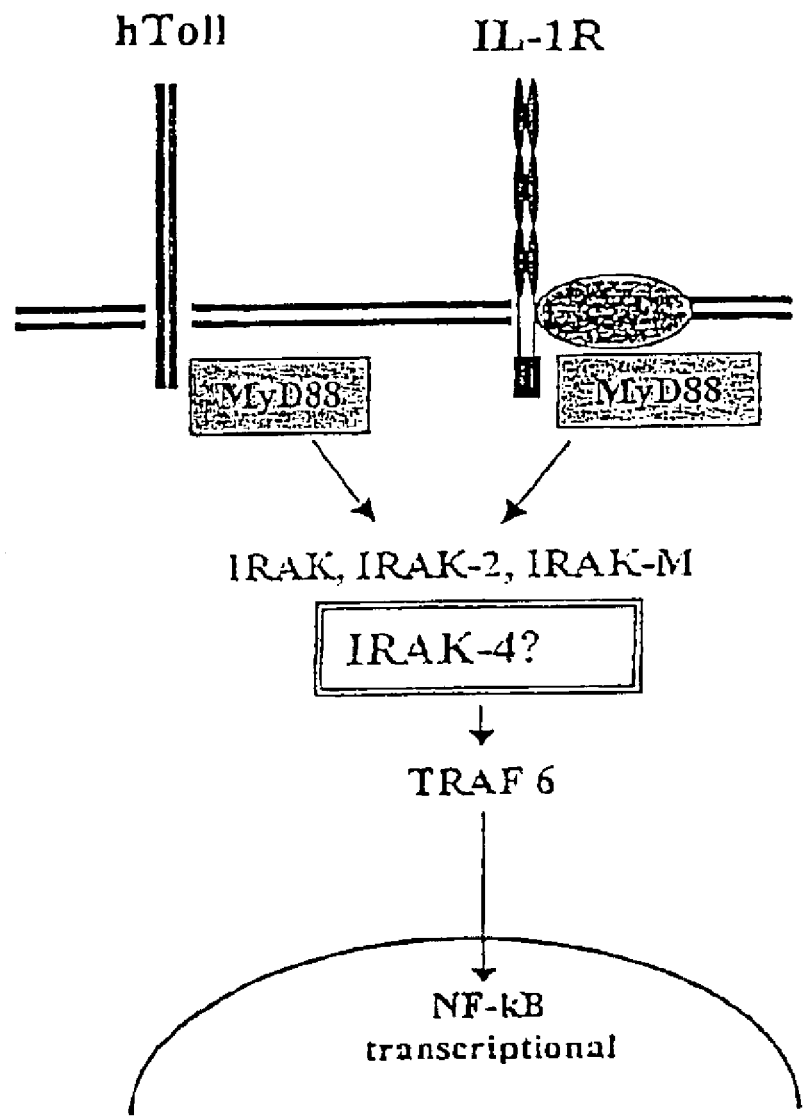
FIG. 5 shows a model of the IRAK signal transduction pathway for the Toll/interleukin-1 (IL-1) receptor family.

IRAK kinases are signal transducers for the Toll/IL-1 receptor family. All members of this family are involved in host defense. The first signaling event for these receptors is the ligand-induced recruitment of cytosolic MyD88 to the receptor complex (FIG. 5). MyD88 in turn acts as an adapter for recruiting IRAK family proteins. IRAK is phosphorylated, then leaves the receptor complex and interacts with TRAF6. This interaction triggers a kinase cascade that eventually leads to the activation of members of the rel and AP-1 family of transcription factors.

A previously known putative protein kinase was originally cloned by immunoscreening of cDNA expression libraries prepared from 4 different renal cell carcinomas. The closest homologues of this protein are members of the Interleukin-1 Receptor-Associated Kinase family, IRAK, IRAK-2 and IRAK-M, and Drosophila kinase PELLE. Sequence analysis of this protein was performed, and it was determined that it is another member of the IRAK family. It is therefore called IRAK-4. All these kinases have a death domain (DD) at their N-terminus and a kinase domain at their C-terminus.

On the basis of the published sequence of IRAK-4, different sets of primers were designed and used to amplify first-strand cDNAs from kidney and placenta. The primers used to clone IRAK-4 were: Forward primer (nucleotides 1–27 of IRAK-4), 5'-GCGAATTCATGAACAAACCC-ATA ACACCATCAACA-3'(SEQ ID NO:42); Reverse primer (nucleotides 1357–1383 of IRAK-4), 5'-GCCTCGAGTTAAGAAGCTGTCATCTCTTGCAGCA-G-3'(SEQ ID NO:43). The bold indicates restriction sites used for cloning. Two amplification products were always obtained that differed in size by about 150 bp. Both bands were cloned and sequenced. The longer form of IRAK-4 (SEQ ID NO:15) was found to correspond to the published sequence (SEQ ID NO:27)(GI 5360131, locus AF155118, accession No. AAD42884; GI 7705841; GI 7705840), except that the sequence differed from the previously known sequence near the 3' end of SEQ ID NO:15 at nucleotides 1295 (T), 1301 (T), 1310 (T), 1332 (A) and 1353 (A) (FIG. 10). The shorter form of IRAK-4 lacks 146 bp at the end of the DD. The short form of IRAK-4 deletes nucleotides 162 to 307 of the IRAK-4 long form. Moreover, an EST clone (GenBank accession No. AA114228) confirmed the existence of the short form, so therefore different isoforms of IRAK-4 appear to exist.

The death domain of IRAK-4 corresponds to nucleotides 25 to 318 (SEQ ID NO:5) of SEQ ID NO:15. The DD corresponds to amino acids 9 to 106 (SEQ ID NO:6) of SEQ ID NO:16.

Both the long and the short forms of IRAK-4 CDNA were in vitro translated, and the in vitro translated proteins obtained were of different size. The deletion in the short form affects the last 2 α-helices of the 5 α-helices in which the DD is organized. Therefore, the short form of IRAK-4 is expected to have altered binding or no longer be able to bind the binding partners that bind to the DD in the long form of IRAK-4.

Figure 6:
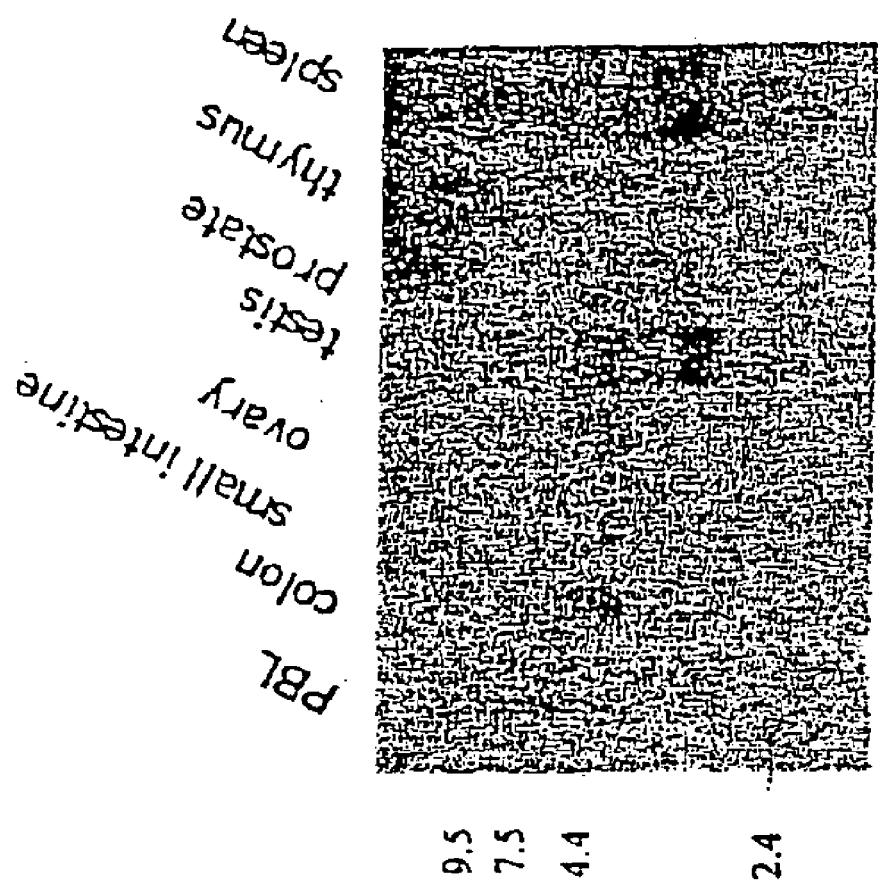
FIG. 6 shows the expression pattern of IRAK4 mRNA.

To characterize the expression of IRAK-4, Northern blot on poly (A)+ RNA from various tissues was performed using the IRAK-4 open reading frame (ORF) as a probe. Briefly, multiple tissue Northern blots were hybridized with a $^{32}$P-labeled cDNA fragment encoding full length IRAK-4. The tissues tested were: peripheral blood leukocytes (PBL), colon, small intestine, ovary, testis, prostate, thymus and spleen. IRAK-4 mRNAs were widely expressed in the adult human tissues examined, with different isoforms ranging from 2.4 to 5.0 kb (FIG. 6).

Figure 7:
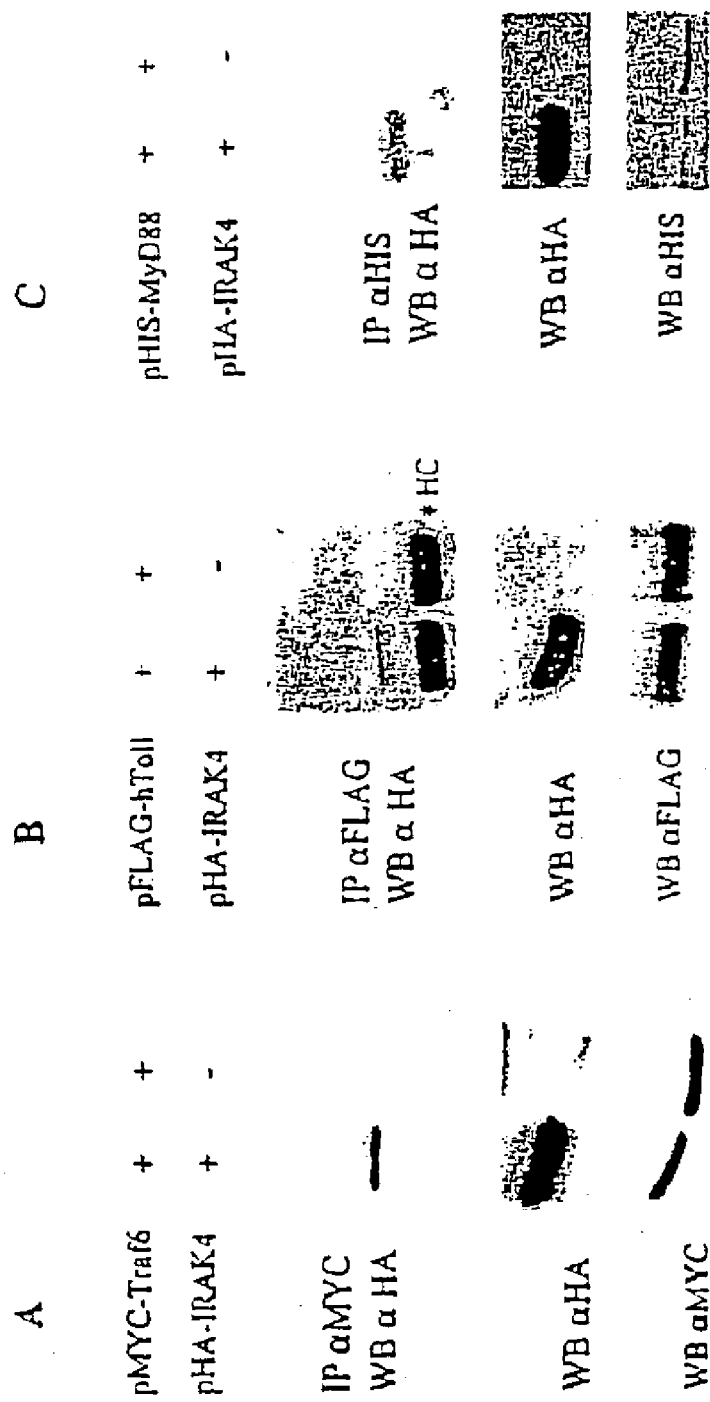
FIG. 7 shows the association of IRAK4 with members of the hToll/IL-1 receptor transduction pathway.

Since IRAKs are signal transducers for the Toll1,IL-1 receptor family, analysis of the interactions between IRAK-4 and proteins of the Toll1/IL-1 receptor transduction pathway was performed. Flag-tagged Toll was expressed in 293T cells, alone or together with HA-tagged IRAK-4. Briefly, 293T cells were transfected with 4 μg of Myc-tagged Traf6 (FIG. 7A), Flag-tagged hToll (FIG. 7B) or His-tagged MyD88 (FIG. 7C), alone or together with 4 μg of expression plasmid for HA-tagged IRAK-4. After 40 h, cell lysates were prepared and immunoprecipitated (IP) with the corresponding antibodies. Coprecipitating IRAK-4 was detected using anti-HA antibody. Immunoblotting analysis of the anti-Flag immunoprecipitates showed that IRAK-4 interacts in vivo with hToll (FIG. 7B). Similarly, immunoblotting analysis of the anti-Myc and anti-His immunoprecipitates similarly showed that IRAK-4 also interacts in vivo with the respectively tagged proteins, the adapter protein MyD88 (FIG. 7C) and Traf6 (FIG. 7A).

Figure 8:
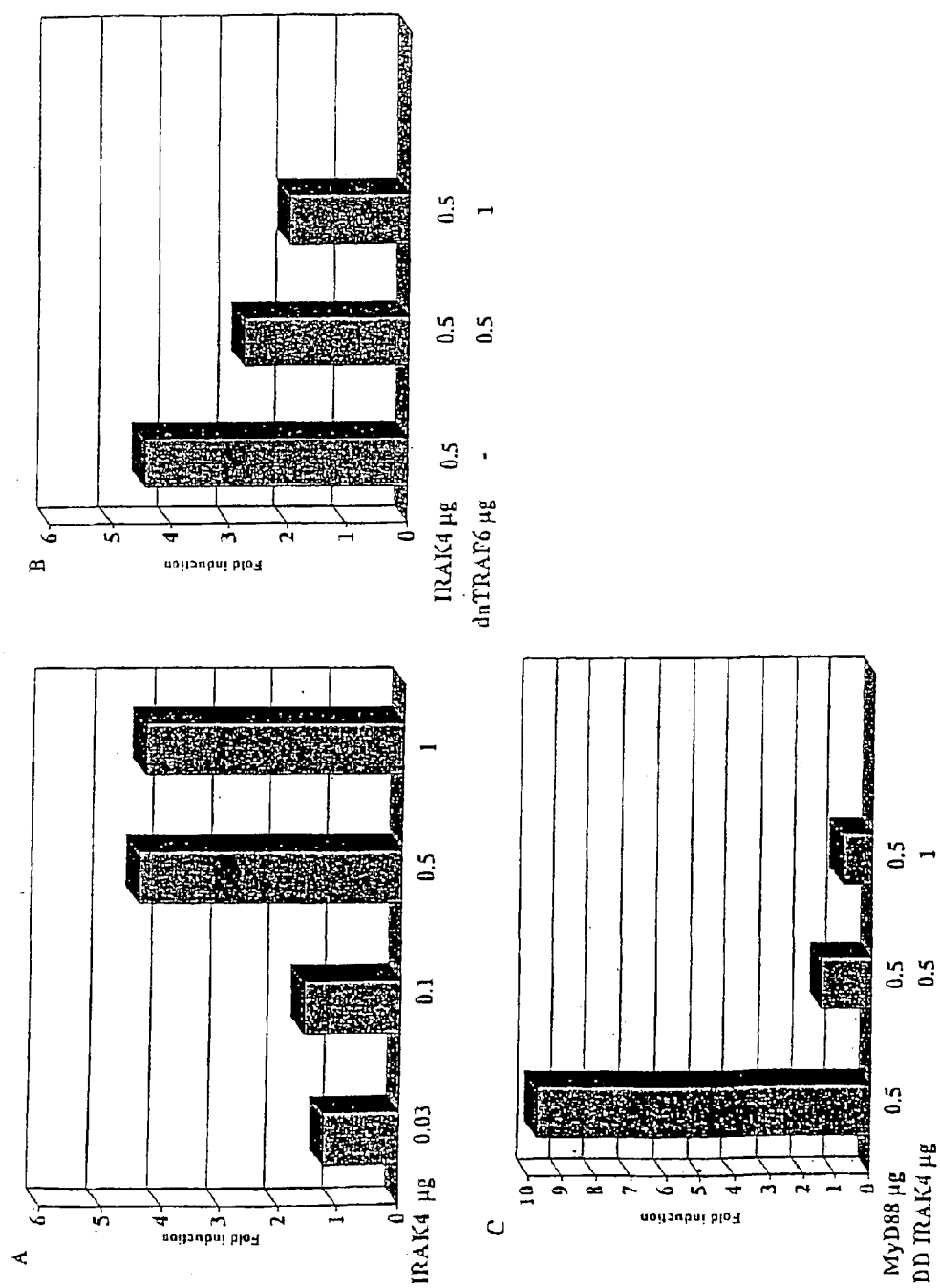
FIG. 8 shows regulation of NFKB activity by IRAK4.

The function of IRAK-4 in regulation of NFκB activity was also characterized. Briefly, 293 cells were transfected with 0.1 μg of pNFκB-luc reporter plasmid, 0.1 μg of pCMVβgal and different amounts of expression plasmid for IRAK4 (FIG. 8A), IRAK4 and different amount of expression plasmid for dominant negative-Traf6 (FIG. 8B), MyD88 and different amount of expression plasmid for the Death Domain of IRAK4 (FIG. 8C). Thirty hours after transfection, luciferase activities were determined and normalized on the basis of β-galactosidase activity (FIG. 8). The Y axis represents the fold of luciferase activity induction relative to cells transfected with empty vector.

The results of the effect of IRAK-4 on NFκB activation are shown in FIG. 8. The results show that overexpression of IRAK-4 can stimulate NFκB activation in a dose-dependent manner (FIG. 8A). Overexpression of a dominant negative form of Traf6 inhibits this IRAK4-mediated NFκB activation (FIG. 8B). Moreover, expression of IRAK-4 death domain alone has a dominant negative effect on MyD88-induced NFκB activation.

VI. *Chlamydia* Death Domain Proteins

This example describes novel death domain proteins of *Chlamydia* species.

Cloning of *Chlamydia* Death Domain Proteins

A computational biology approach was used to search for death domain proteins in *Chlamydia* species. For this approach, a representative set of death domains was used as queries and a cascade of TBLASTN and PSI-BLAST searches were performed on nucleotide databases at NCBI (htgs, gss, dbest) and the NR protein database. Using sequence comparison, a hypothetical protein of unknown function from *C. trachomatis*, designated CT610, was found to contain a putative death domain. The new candidate death domain was confirmed by running a FFAS sequence comparison against a database of proteins of known structure (PDB) enriched for apoptotic domains. The *C. trachomatis* hypothetical protein CT610 (GI:3329055) had 26% identity and a FFAS Z-score=9.3 (similarity measure) with human DR5, 29% identity with human DR4 and 25% identity with human Fas when using GAP alignment methods. This degree of sequence identity is comparable to the homology shared among the TNF-Receptor family members. Secondary structure prediction methods showed that the death domain of CT610 can be comprised of six α-helices, similar to mammalian death domains. Portions of the CT610 protein outside the death domain showed no similarity to known domains in public databases. In addition, homologues of this death domain containing protein were found in three other *Chlamydia* species (*Chlamydia muridarum, C. pneumoniae,* and *C. psitacci*)(FIG. 11).

The CT610 gene was found within the complementary strand of GenBank accession No. AE001331 (gi|3329046|gb|AE001331.1|; *Chlamydia trachomatis* section 58 of 87 of the complete genome) in close proximity to the *Chlamydia* rpoD gene encoding the major sigma factor ($\sigma^{66}$) which produces a transcription factor implicated in late-gene expression. The nucleotide sequence of CT610 is referenced as SEQ ID NO:23, and the encoded amino acid sequence is referenced as SEQ ID NO:24. Table 2 summarizes characteristics of the CT610 polypeptide.

TABLE 2

Characteristics of CT610 Polypeptide

Molecular Weight 26733.28 Daltons
231 Amino Acids
23 Strongly Basic (+) Amino Acids (K, R)
40 Strongly Acidic (−) Amino Acids (D, E)
81 Hydrophobic Amino Acids (A, I, L, F, W, V)
55 Polar Amino Acids (N, C, Q, S, T, Y)
4.802 Isoelectric Point
−15.702 Charge at PH 7.0
Total number of bases translated is 696

| | |
|---|---|
| % A = 30.17 | (210) |
| % G = 23.56 | (164) |
| % T = 31.47 | (219) |
| % C = 14.80 | (103) |
| % Ambiguous = 0.00 | (0) |
| % A + T = 61.64 | (429) |
| % C + G = 38.36 | (267) |
| Davis, Botstein, Roth Melting Temp C. | 79.91 |
| Wallace Temp C. | 2132.00 |

Using flanking primers, CT-610 was cloned from from genomic DNA of *Chlamydia trachomatis*, LGV-II, strain 434 (ABI/Maryland). The primers used were 5' primer ATGATGGAGGTGTTTATG (SEQ ID NO:44) and 3' primer ATAAGATTGATGACAACTAC (SEQ ID NO:45). The cloned product was designated CTDD. The nucleotide sequence of CTDD is referenced as SEQ ID NO:19, and the amino acid sequence is referenced as SEQ ID NO:20. Table 3 summarizes characteristics of the CTDD polypeptide.

TABLE 3

Characteristics of CTDD Polypeptide

Molecular Weight 26332.42 Daltons
231 Amino Acids
24 Strongly Basic (+) Amino Acids (K, R)
40 Strongly Acidic (−) Amino Acids (D, E)
81 Hydrophobic Amino Acids (A, I, L, F, W, V)
55 Polar Amino Acids (N, C, Q, S, T, Y)
4.872 Isoelectric Point
−14.702 Charge at PH 7.0
Total number of bases translated is 696

| | |
|---|---|
| % A = 29.89 | (208) |
| % G = 23.71 | (165) |
| % T = 31.47 | (219) |
| % C = 14.94 | (104) |
| % Ambiguous = 0.00 | (0) |
| % A + T = 61.35 | (427) |
| % C + G = 38.65 | (269) |
| Davis, Botstein, Roth Melting Temp C. | 80.03 |
| Wallace Temp C. | 2138.00 |

The cloned CTDD sequence was found to differ from the published CT-610 sequence at 3 bases. The differing bases are shown in Table 4. Two are silent mutations, but the G>C exchange at bp 664 encodes a different amino acid at position 222, changing G>R.

TABLE 4

Nucleotide Changes from CT-610 to CTDD

| | |
|---|---|
| bp 75 | A->G silent mutation |
| bp 615 | A->G silent mutation |
| bp 664 | G->C leads to amino acid exchange G->R |

The death domain of CTDD was identified as nucleotides 268 to 462 (SEQ ID NO:9) of SEQ ID NO:19 and amino acids 90 to 154 (SEQ ID NO:10; DLW . . . KIR) of SEQ ID NO:20.

The cloned sequence was confirmed from several independent clones and then sub-cloned into expression vectors. The ORF encoding CTDD was subcloned into the EcoRI-XhoI sites of pGEX4T1 (Pharmacia), pcDNA3-HA (Invitrogen), pcDNA3-myc, and the EcoRI-SalI sites of pEGFP N3. A cDNA encoding myc-CTDD fusion was subcloned into the Hind III and SalI sites of pEGFP-N1 and pERFP-N1 (Clontech). Confocal microscopy analysis of cells transfected with a plasmid encoding a RFP-CTDD fusion protein demonstrated a cytosolic location.

Table 5 shows a comparison of various amino acid positions in CTDD to TNFR1, DR4, DR5 and Fas, with corresponding loss of function (LoF) mutations indicated. The "*" indicates a Fas lpr mutation, which is a single amino acid exchange in murine Fas leading to loss of function of the receptor. Mice bearing this mutation exhibit autoimmune disease. This important amino acid (Val in Fas at position 242) is conserved in *Chlamydia* CTDD.

TABLE 5

Comparison of Amino Acids in CTDD and TNFR1, DR4, DR5 and Fas.

| aa-Position | TNF R1 | DR-4 | DR-5 | Fas | CT | LoF |
|---|---|---|---|---|---|---|
| 232 | F | L | L | F | F | |
| 234 | R | R | R | R | F | A |
| 238 | L | L | L | V* | V | N |
| 242 | D | K | D | K | P | A |
| 244 | D | D | K | D | E | A |

Interaction of CTDD with Other DD-Family Proteins

CTDD was tested for interactions in vitro with a variety of human DD-family proteins, including TNF-family death receptors (TNFR1, DR4, DR5, Fas [CD95]), adapter proteins (FADD, RIP, RAIDD), and c-FLIP. For these experiments CTDD was produced as a GST-fusion protein and incubated with various in vitro translated, $^{35}$S-labeled DD-family proteins. Briefly, the plasmid pGEX4T-CTDD was introduced into *E.coli* strain XL1-Blue. Glutathione S-transferase (GST) fusion proteins were obtained by induction with 0.1 mM Isopropyl β-thiogalactoside at 25° C. for 8 hours and then purified by using glutathione-Sepharose. Plasmids containing various DD-containing proteins were in vitro transcribed and translated in the presence of [$^{35}$S]L-methionine using the TNT kit from Promega. GST-CTDD and control GST-CD40 (cytosolic domain) fusion proteins (1 μg) were immobilized on gluthathione-Sepharose (Amersham, Pharmacia) and then mixed with 1 μl in vitro translated $^{35}$S-labeled target proteins for 1 hr at 4° C. Beads were then washed three times in 1 ml of 140 mM KCl, 20 mM Hepes pH 7.5, 5 mM MgCl$_2$, 2 mM EGTA, 0.5% NP40 and bound proteins were analyzed by SDS/PAGE and autoradiography. The results of the protein-protein interaction assay are shown in Table 6.

TABLE 6

In vitro Interactions with CTDD and Various Polypeptides

| In vitro translated protein | GST-CD40 | GST-CTDD |
|---|---|---|
| Luciferase | – | – |
| FADD | – | – |
| RAIDD | – | – |
| RIP | – | – |
| c-Flip | – | – |
| CTDD (self association) | – | +/– |
| Fas without DD | – | – |
| Dr-4 | – | +++ |
| Dr-5 | – | +++ |
| Fas | – | +++ |
| TNF-RI | – | + |

–: no interaction
+/–: less than 5% of input retrieved
+: less than 10% of input retrieved
++: approx. 10% input retrieved
+++: more than 10% input retrieved Based on the in vitro binding assay results shown in Table 6, GST-CTDD, but not GST-CD40 or a variety of other control proteins, bound TNF-family death receptors, Fas, DR4, DR5, and to some extent TNFR1. However, CTDD did not significantly interact in vitro with FADD, RAIDD, RIP, c-FLIP, itself (CTDD), or a Fas-mutant lacking its DD.

Further, co-immunoprecipitation experiments also demonstrated that CTDD is capable of specifically interacting with TNF-family death receptors such as DR5 in mammalian cells. Briefly, 293 cells ($5 \times 10^6$) were cultured in the presence of 50 μM benzoyl-Val-Ala-Asp-fluoromethylketone (zVAD-fmk) (Enzyme Systems Products), in order to perserve cell viability, and co-transfected with 1 μg pcDNA3-DR5, pERFP-myc-CTDD, pcDNA3-myc-XIAP, pcDNA3-Flag-Casp9, using a lipofection reagent (Bioporter, Gene Therapy Systems). At 24 hrs post-infection, cells were collected, washed with ice-cold PBS, and resuspended in lysis buffer (20 mM Tris-HCl, pH 7.4, 150 mM NaCl, 0.2% Nonidet P40, 10% glycerol and complete protease inhibitor cocktail (Roche)) for 15 min. on ice. The lysate was cleared twice by centrifugation at 16,000 g for 10 min. at 4° C. The soluble fraction was precleared with 20 μL protein-G-Sepharose 4B (Zymed) overnight at 4° C. and immunoprecipitated with 10 μL anti-myc (Santa Cruz Biotechnology) conjugated Sepharose beads for 4 hrs at 4° C. Beads recovered by centrifugation were then washed four times with 1 ml lysis buffer and boiled in Laemmli loading solution before performing SDS-PAGE and immunoblotting using anti-DR-4/DR5 (Alexis), monoclonal mouse anti-Flag (Sigma), or monoclonal mouse anti-myc (Zymed) followed by horse radish peroxidase-conjugated goat anti-mouse-IgG antibodies (Bio-Rad). Detection was accomplished using Enhanced Chemiluminescence (ECL)(Amersham).

Figure 12:
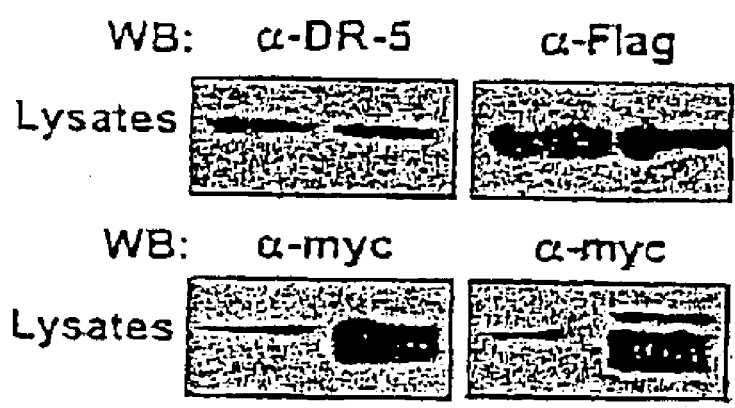
FIG. 12 shows that CTDD and DR-5 can be co-immunoprecipitated in vitro.

The co-immunoprecipitation experiment confirmed an interaction between CTDD and DR-5 (see FIG. 12). In the same experiment XIAP did not interact with DR-5 and CTDD did not interact with caspase 9. However, caspase 9 did interact with XIAP as expected, and serves as a positive control for the experiment.

Apoptosis Induction and Caspase Activation by CTDD

Figure 13:
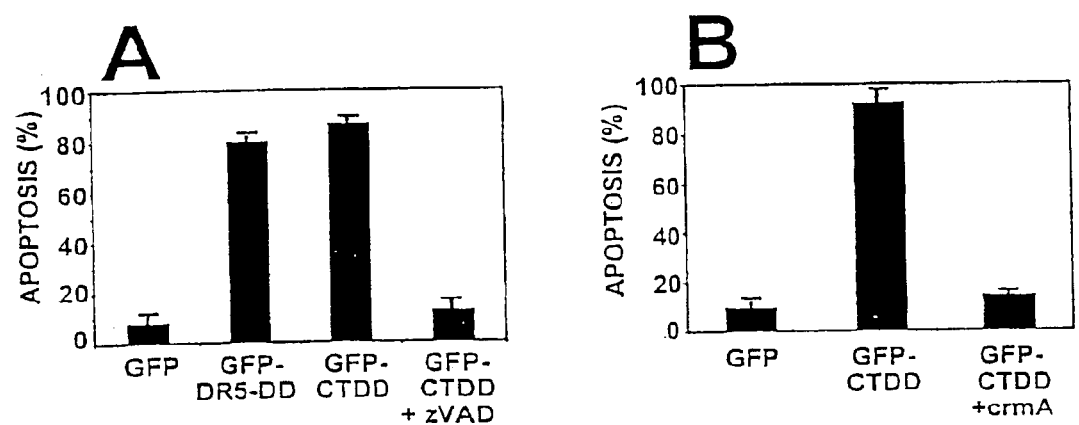
FIG. 13 shows the induction of apoptosis by CTDD.

Transfection experiments were performed to test the effects of CTDD on apoptosis in mammalian cells (see FIG. 13). Briefly, HeLa (panel A) and Hep3B (panel B) were maintained in DMEM (Irvine Scientific) and supplemented with 10% FBS, 1 mM L-glutamine, and antibiotics. Cells ($10^6$) were transfected with 1 μg of pEGFP control, pEGFP-CTDD, pEGFP-DR5-death domain, or CrmA, alone or in combination, normalizing total DNA content. In some cases 100 μM zVAD-fmk was added to cultures. Both floating and adherent cells were recovered 1 day later, pooled, and staining with 0.1 μg/ml 4'-6-diamidino-2-phenylindole (DAPI). The percentage of GFP-positive cells with apoptotic morphology was determined by UV-microscopic analysis of DAPI-stained cells (mean±SD; n=3) at 1 day after transfection.

When transiently transfected into HeLa cells, plasmids producing CTDD induced apoptosis to an extent comparable to a prototypical apoptotic stimuli such as DR-5 and this induction of apoptosis was blocked by addition of zVAD-fmk, an irreversible broad-spectrum caspase inhibitor, to the cultures (FIG. 13). In addition, co-expression of the cowpox protein CrmA, a selective inhibitor of caspases-1 and -8, also resulted in blockage of CTDD-induced apoptosis. Immunoblotting experiments confirmed that zVAD-fmk and CrmA did not interfere with CTDD protein production (data not shown). The morphology of the dying cells was typical of apoptosis, with markedly condensed chromatin, fragmentation of the nucleus, membrane blebbing, cell rounding and shrinkage (data not shown). Thus, CTDD induces apoptosis through a caspase-dependent mechanism.

Figure 14:
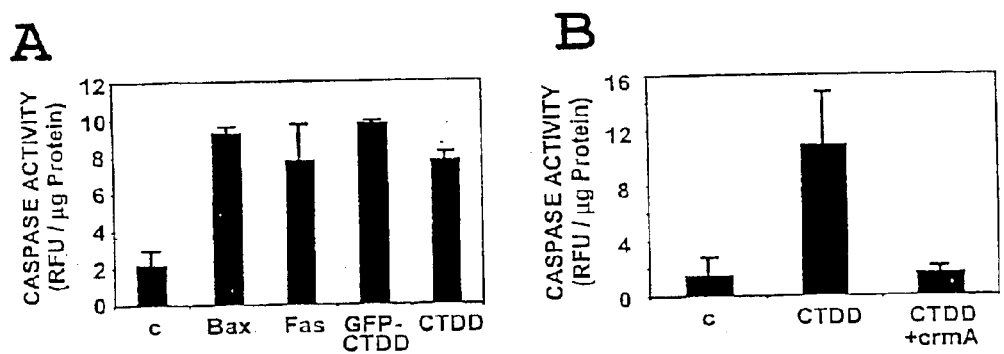
FIG. 14 shows the induction of caspase activity by CTDD.

CTDD induced activation of caspases as determined by enzyme assays measuring activity of proteases capable of cleaving a fluorigenic substrate, Ac-DEVD-AFC (see FIG. 14). Briefly, HeLa 229 (panel A) and Hep3B (panel B) cells were transfected with 1 μg of pEGFP control, pEGFP-CTDD, pERFP-CTDD, Bax, Fas, or CrmA. Cells were lysed in caspase lysis buffer (10 mM Hepes pH 7.4, 25 mM NaCl, 0.25% Triton X-100, 1 mM EDTA) after 18 hours of transfection. Caspase activity was assayed by release of 7-amino-4-trifluoromethyl-coumarin (AFC) from Ac-DEVD-AFC (Calbiochem-Novabiochem) using a spectrofluorimeter. Data are expressed as Relative Fluorescence Units (RFU) per μg total protein (mean±SD; n=3) after a 30 minute reaction.

When transiently transfected into HeLa cells, plasmids producing CTDD increased caspase activity to an extent comparable to prototypical apoptotic stimuli such as Bax and Fas (FIG. 14). In addition, this activation of caspases was reversed in Hep3B cells that were co-transfected with CrmA.

Time Course of CTDD Gene Expression and Correlation with Apoptosis

*Chlamydiae* are obligate intracellular bacteria. These pathogens engage in a unique relationship with their infected host. Upon entering host cells, the parasite undergoes a developmental cycle from the infectious form, called an elementary body (EB), to a non-infectious, vegetative growth form, called a reticulate body (RB), and then eventually back to the replication-incompetent infectious form. After the transition back to the infectious form, the host cell dies and releases its infectious load. Cytotoxicity due to *Chlamydia* infection is well-recognized (Campbell et al., *J. Gen. Micro.* 135: 1153–65 (1989)), but the mechanism by which host cells die remains poorly understood. Apoptosis induction at the end of the infectious cycle has been demonstrated, implicating cell death in the mechanism of release of infectious particles (Gibellini et al., *Zentralblatt fur Bakteriologie* 288:35–43 (1998)).

To determine whether and when CTDD is expressed, RT-PCR analysis was performed. For these experiments HeLa cervical epithelial cell cultures were inoculated with EBs from *C. trachomatis* L2/434/Bu (ATCC) at a multiplicity of infection (MOI) of 2 or 5 and analyzed for apoptosis or CTDD gene expression by RT-PCR analysis. Preparation of EBs and determination of infectivity were performed as described in Campbell et al., supra, and Ojcius et al., *J. Biol. Chem.* 273:7052–8 (1998). HeLa 229 cells were grown in 9 cm Petri dishes to 70% confluency, then infected at a MOI of 2 or 5. To ensure even infection of the cells, plates were gently agitated on a rocking platform for 2 hours at 37° C. To remove unabsorbed EBs, plates were washed three times with PBS, then supplied with fresh medium and incubated at 37° C. in a 5% $CO_2$ humified atmosphere. The percentage of apoptotic cells was determined at various times post-infection by DAPI staining as described above. In addition, at various times post-infection supernatants and adherent cells were harvested, washed once with PBS, snap-frozen in liquid nitrogen, and stored at −80° C.

RNA from infected HeLa cells was extracted using a modified chloroform/phenol procedure (TRIZOL; Life Technologies). RNA (3 μg) from each sample was treated with DNase I (Roche) and cDNA was generated using reverse transcriptase (RTase) (Superscript II; LIFE TECHNOLOGIES) following the manufacturer's protocol. To detect possible contaminating genomic DNA in the RNA preparations, control reactions containing no reverse transcriptase were performed. A 5% (vol:vol) aliquot of the cDNAs and no-RTase control samples were subsequently amplified by PCR using TAQ DNA polymerase (Qiagen) and the following primer sets: CTDD-forward and reverse (see above); groEL forward 5'-GCAGTCATTCGCGTTGGA-3' (SEQ ID NO:59); and reverse 5'-CGCAGAACGGGACATAACTTG-3' (SEQ ID NO:60); and human β-actin forward 5'-TGATATCGCCGCGCTCGTCGTC-3' (SEQ ID NO:61); and reverse 5'-GGATGGCATGGGGGAGGGCATA-3' (SEQ ID NO:62). After denaturing DNA at 95° C. for 5 min, thermocycling was performed for 45 cycles using 95° C./30 s, 55° C./30 s, 72° C./30 s with a final extension at 72° C. for 5 min. Amplified fragments were analysed by agarose gel-electrophoresis, stained with ethidium bromide, and their identity confirmed by DNA sequencing.

Figure 15:
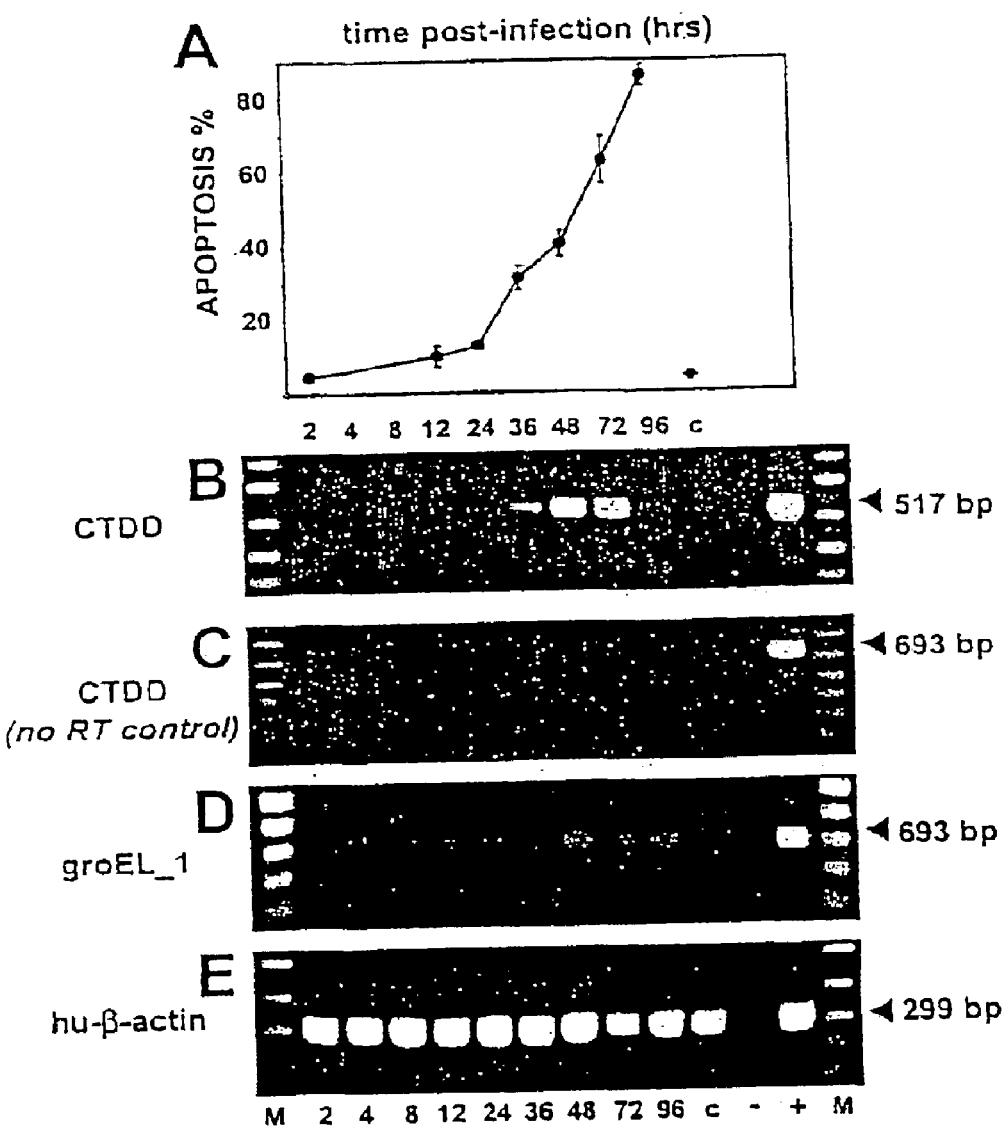
FIG. 15 shows the correlation between apoptosis and CTDD gene expression at various times post-infection with *Chlamydia*.

As shown in FIG. 15, mRNA corresponding to CTDD became detectable at about 36 hr after infection, reaching maximum levels at 48 to 72 hrs. Thus, CTDD is expressed late in the *Chlamydia* infectious cycle. Furthermore, the timing of CTDD expression is in accordance with the onset and progression of apoptosis in infected HeLa cells.

Roles for CTDD in *Chlamydia* Pathophysioloqy

As an intercelluar parasite, it would be advantageous if intracellular bacteria were able to regulate host cell apoptosis for a wide variety of reasons, including: (a) suppressing apoptosis so that intracellular pathogen replication can occur; (b) inducing apoptosis to facilitate pathogen release, pathogen invasion into tissues, or for creating a source of nutrients from cell corpses; and (c) killing inflammatory cells to avoid immune attack. Previous studies have established that infection of mammalian cells with *Chlamiydiae* species can either suppress or induce apoptosis, depending on whether examined early or late in the infectious cycle of these obligate intracellular bacteria (Fan et al, *J. Exp. Med.* 187:487–96 (1998) and Ojcius et al., *J. Immunol.* 161: 4220–6 (1998)). However, discovery of the responsible bacterial genes has been enigmatic. In the experiments described above, it was demonstrated that the *C. trachomatis* genome contains a gene encoding a bacterial DD protein, CTDD, which is capable of binding several DD-containing TNF-family receptors and inducing caspase activation and apoptosis of human cells. This apoptosis-inducing bacterial gene is located in the late-portion of the circular *C. trachomatis* genome, and is expressed late in the infection cycle, at a time when apoptosis is induced by these bacteria in vitro. Closely related genes were also found in the late-portions of the genomes other *Chlamiydia* species which create clinically significant infections in various species.

One possible role for CTDD in *Chlamydia* pathophysiology is in the induction of apoptosis to facilitate infectivity. In infected epithelial cells, CTDD is expressed late in the infectious cycle correlating with the onset of cell death seen in vitro. Since CTDD binds the cytosolic domains of DD-containing TNF-family death receptors, CTDD could trigger caspase activation and apoptosis by activating these receptors in a ligand-independent fashion. This is consistent with the ability of CrmA to suppress CTDD-induced apoptosis. CrmA is a selective inhibitor of caspase-8 (and caspase-1), which suppresses apoptosis induced by TNF-family death receptors, but not cell death triggered by stimuli that activate other apoptosis pathways. Alternatively, in vivo studies of *Chlamydia*-induced apoptosis in the endocervix of mice have shown that neutralizing antibodies against TNF-RI can reduce cytotoxicity caused by these bacteria. Thus, it is possible that CTDD sensitizes TNF-family death receptors to their ligands, allowing them to signal more efficiently or increasing the amounts of high-affinity receptors on the cell surface.

Another possible role for CTDD in *Chlamydia* pathophysiology is in the induction of apoptosis to avoid immune attack. It has been demonstrated that *Pseudomonas aeroginosa* can trigger apoptosis of macrophages through a Fas-dependent mechanism, demonstrating that these extracellular bacteria deliver signals to mammalian cells that engage death receptor pathways. Since macrophages represent one of the preferred host cells of *Chlamydia* (in addition to epithelial cells), a similar strategy can be employed by *Chlamydia* to evade immune attack.

Another possible role for CTDD in the pathophysiology of *Chlamydiae* is in interference of apoptosis. *Chlamydiae* have been implicated in interference with the eucaryotic death machinery, where an apoptosis-resistant state has been associated with the early replicative phase of the infectious cycle. By lack of a DED, it is possible that CTDD interferes with the DISC (death inducing signalling complex) resulting in disruption of the death signaling cascade.

Thus *Chlamiydiae* can possess mechanisms for both suppression (early) and induction (late) of host cell apoptosis. This disclosure provides the first demonstration that some types of bacteria harbor apoptosis-regulating genes which share significant sequence similarity with endogenous components of the host cell apoptosis machinery.

VII. Human Death Effector Domain Protein

This example describes the identification of a novel death effector domain from human.

Using bioinformatics tools, a sequence was identified that contains a death effector domain. Briefly, using the sequences of different death effector domains (DED), GenBank and other DNA/protein databases were searched by "Saturated BLAST" for the existence of new DED-containing proteins (Li et al., *Bioinformatics* 16:1105–1110 (2000)). This search identified two human EST clones (AW449244 and AA218681) that contained a DED most homologous to the DED of DEDD (DED containing DNA-binding protein) (Stegh et al., *EMBO J.* 17:5974–5986 (1998)). The newly identified gene was designated DED4 and was predicted from nucleotide sequences (chromosomal DNA and EST DNA) GI Nos. 4210498, 1832773, and 6990020. The nucleotide sequence of DED4 is referenced as SEQ ID NO:17, and the amino acid sequence is referenced as SEQ ID NO:18.

Using the deduced protein sequences of the EST clones AW449244 and AA218681 in tBLASTn searches, other EST sequences containing overlapping identical nucleotide sequences were identified (BE797255, BE242821, AW229739, and AW227145). Subsequently, these EST sequences were used to search for more overlapping sequences. The correct reading frame was identified by comparing the sequence of DED4 to the sequences of human DEDD and mouse DED4. DED4 was found to have approximately 50% identity in the nucleotide sequence with DEDD, and approximately 80% identity in the amino acid sequence. DED4 has its DED at approximately the same position as in DEDD, both proteins are predicted to be about the same size. Similar to DEDD, DED4 has a nuclear localization signal. The DED4 gene is located on chromosome 19, whereas DEDD is located on chromosome 1.

The death effector domain of DED-4 was identified as nucleotides 124 to 426 (SEQ ID NO:7) of SEQ ID NO:17 and amino acids 12 to 112 (SEQ ID NO:8) of SEQ ID NO:18. The nuclear localization sequence was identified as nucleotides 157–222 of SEQ ID NO:17 and amino acids 53 to 74 of SEQ ID NO:18.

DED4 cDNA was amplified from the cDNA of the neuronal precursor cell line NT2 and confirmed by sequencing. The primers used to amplify DED4 were: 5' CTC CGC CGC CGT CTG G 3' (SEQ ID NO:46) and 5' CGC CCA GGA GTC ATC GGA CGC 3'(SEQ ID NO:47). Northern Blot analysis was performed using a radioactive probe containing the death effector domain in its sequence. Northern analysis revealed a 2.2 kb transcript, which is similar in size to DEDD. Expression of DED4 was observed in most of the human tissues tested in a multiple tissue blot. Expression of DED4 in Northern blot analysis was high in brain, heart, skeletal muscle, kidney, lung and peripheral blood leukocytes. Expression was moderate in thymus and placenta. Expression was weak in colon and small intestine.

DED4 constructs are made, for example as tagged fusions using Myc, HA, His, and the like, and tested for interactions, as described above. DED4 is tested for interactions with itself and DEDD, as well as other molecules that function in apoptosis. Possible interaction partners with DED4 include FADD, caspase-8, caspase-10, FLASH, FLIP and DAP3 and other DED-containing proteins.

VIII. Nerve Growth Factor Receptor-Interacting Death Domain

A mouse EST in the Genbank database (accession No. AV149215) that has homology to mouse p75 nerve growth factor receptor. The EST has 295 base pairs. The NIDD protein was predicted from mouse nucleotide sequences (EST database at NCBI, GI 5353348), and rat and bovine homologues (GI 4607778 and GI 6960635, respectively) were also found.

Because this EST was not commercially available, the gene was cloned by RACE. The primers used for RACE were: 5'-RACE primer (5'-CCGAGGTGGC-CTGCCAGCTCCTG-3'; SEQ ID NO:48); 3'-RACE primer (5'-ACACCCGGACCTTGCCTGCCAGCTTTAC-3'; SEQ ID NO:49). 3'- and 5'-RACE PCR was performed using RNA from mouse brain. A band about 700 bp long was observed after 5'-RACE, and a band about 600 bp long was observed after 3'-RACE PCR. Sequencing confirmed that 5'-RACE product had a start codon (ATG) and that the 3'-RACE product had a stop codon (TGA). Because about 100 bps of these two products were overlapped, RCR was performed using the two RACE products as templates. The primers for this PCR were 5'-ATGCTTTATAACGTCAGC-3' (SEQ ID NO:50) and 5'-TCACACCACCGA-GGAGCTCTC-3' (SEQ ID NO:51). The sequencing of this PCR product showed that the gene has 687 nucleotides. The gene was designated NGFR-interacting Death Domain (NIDD) based on its binding with NGFR (see below).

The death domain of NIDD was identified as nucleotides 418 to 630 (SEQ ID NO:11) of SEQ ID NO:21 and amino acids 140–210 (SEQ ID NO:12) of SEQ ID NO:22. A putative transmembrane domain was also identified (nucleotides 157 to 222 of SEQ ID NO:21; amino acids 53 to 74 of SEQ ID NO:22, IIPVY . . . LLAYVAF).

NIDD cDNA was cloned into pcDNA3 vector with myc- and and HA-tags. After transfection of pcDNA3-myc-tagged NIDD and pcDNA3-HA-tagged NIDD into 293T cell line, cell lysates were immunoprecipitated with myc-beads and analyzed by Western blotting using anti-HA antibody. Co-immunoprecipitation showed that NIDD has self binding activity. Co-immunoprecipitation experiments were also performed with pcDNA3-HA -tagged NIDD and pcDNA3-FLAG-tagged rat NGF (nerve growth factor)-receptor. NIDD was found to bind to rat NGF-receptor and TRAF-3. The expression of NIDD was analyzed using 32P-labeled full-length NIDD cDNA. NIDD is expressed in several tissues, including heart, lung, liver, kidney and testis.

Although the invention has been described with reference to the examples above, it should be understood that various modifications can be made without departing from the spirit of the invention. Accordingly, the invention is limited only by the following claims.

SUMMARY OF SELECTED NNUCLEOTIDE AND AMINO ACID SEQUENCES ENCODING DD, DED, AND NB-ARC CONTAINING PROTEINS

Sequence ID No. 1 is a nucleotide sequence of a human DAP3 DED.

Sequence ID No. 2 is an amino acid sequence for a human DAP3 DED.

Sequence ID No. 3 is a nucleotide sequence of a human DAP3 NB-ARC domain.

Sequence ID No. 4 is an amino acid sequence for a human DAP3 NB-ARC domain.

Sequence ID No. 5 is a nucleotide sequence of a human IRAK4 DD.

Sequence ID No. 6 is an amino acid sequence for a human IRAK4 DD.

Sequence ID No. 7 is a nucleotide sequence of a human DED4 DED.

Sequence ID No. 8 is an amino acid sequence for a human DED4 DED.

Sequence ID No. 9 is a nucleotide sequence of a C. trachomatis CTDD DD.

Sequence ID No. 10 is an amino acid sequence for a C. trachomatis CTDD DD.

Sequence ID No. 11 is a nucleotide sequence of a mouse NIDD DD.

Sequence ID No. 12 is an amino acid sequence for a mouse NIDD DD.

Sequence ID No. 13 is a nucleotide sequence of a full length human DAP3 gene.

Sequence ID No. 14 is an amino acid sequence for a full length human DAP3 protein.

Sequence ID No. 15 is a nucleotide sequence of a full length human IRAK4 gene.

Sequence ID No. 16 is an amino acid sequence for a full length human IRAK4 protein.

Sequence ID No. 17 is a nucleotide sequence of a full length human DED4 gene.

Sequence ID No. 18 is an amino acid sequence for a full length human DED4 protein.

Sequence ID No. 19 is a nucleotide sequence of a full length *C. trachomatis* CTDD gene.

Sequence ID No. 20 is an amino acid sequence for a full length *C. trachomatis* CTDD protein.

Sequence ID No. 21 is a nucleotide sequence of a full length mouse NIDD gene.

Sequence ID No. 22 is an amino acid sequence for a full length mouse NIDD protein.

Sequence ID No. 23 is a nucleotide sequence of a full length *C. trachomatis* CT-610 gene.

Sequence ID No. 24 is an amino acid sequence for a full length *C. trachomatis* CT-610 protein.

Sequence ID No. 25 is a nucleotide sequence of a full length human IRAK4 short gene.

Sequence ID No. 26 is an amino acid sequence for a full length human IRAK4 short protein.

Sequence ID No. 27 is a nucleotide sequence of a full length human IRAK4 gene from Genbank sequence.

Sequence ID No. 28 is an amino acid sequence for a full length human IRAK4 protein from Genbank sequence.

Sequence ID No. 52 is a nucleotide sequence of a *C. muridarum* CTDD DD.

Sequence ID No. 53 is an amino acid sequence for a *C. muridarum* CTDD DD.

Sequence ID No. 54 is a nucleotide sequence of a full length *C. muridarum* CTDD gene.

Sequence ID No. 55 is an amino acid sequence for a full length *C. muridarum* CTDD protein.

Sequence ID No. 56 is an amino acid sequence for a *C. pneumoniae* CTDD DD.

Sequence ID No. 57 is an amino acid sequence for a full length *C. pneumoniae* CTDD protein.

Sequence ID No. 58 is an amino acid sequence for a *C. psittaci* CTDD DD.

That which is claimed is:

1. An isolated nucleic acid molecule consisting of DNA encoding a polypeptide consisting of the amino acid sequence set forth in SEQ ID NO:6.

2. A vector that expresses the nucleic acid molecule of claim 1.

3. Recombinant cells that express the nucleic acid molecule of claim 1.

4. The isolated nucleic acid molecule of claim 1, said nucleic acid consisting of the sequence of SEQ ID NO:5.

5. A method for expression of a polypeptide consisting of an amino acid of SEQ ID NO:6, said method comprising culturing cells of claim 3 under conditions suitable for expression of the polypeptide consisting of said amino acid of SEQ ID NO:6.

6. An isolated nucleic acid molecule consisting of a label linked to DNA consisting of DNA encoding a polypeptide consisting of the amino acid sequence set forth in SEQ ID NO:6.

7. The isolated nucleic acid of claim 6, said DNA consisting of a sequence set forth in SEQ ID NO:5.

8. The isolated nucleic acid of claim 6, said label being a fluorescent labeling agent.

9. The isolated nucleic acid of claim 6, wherein said label is a radioactive element.

10. The isolated nucleic acid of claim 6, wherein said label is an enzyme.

11. The isolated nucleic acid of claim 10, wherein said label is selected from the group consisting of horseradish peroxidase and glucose oxidase.

* * * * *